US011331335B2

(12) United States Patent
Mazmanian et al.

(10) Patent No.: US 11,331,335 B2
(45) Date of Patent: May 17, 2022

(54) SEPSIS TREATMENT AND RELATED COMPOSITIONS METHODS AND SYSTEMS

(71) Applicant: CALIFORNIA INSTITUTE OF TECHNOLOGY, Pasadena, CA (US)

(72) Inventors: Sarkis K. Mazmanian, Porter Ranch, CA (US); June L. Round, Salt Lake City, UT (US); Yue Shen, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 470 days.

(21) Appl. No.: 15/179,810

(22) Filed: Jun. 10, 2016

(65) Prior Publication Data

US 2016/0361343 A1    Dec. 15, 2016

Related U.S. Application Data

(60) Provisional application No. 62/173,497, filed on Jun. 10, 2015.

(51) Int. Cl.
A61K 31/715    (2006.01)
C12N 5/078     (2010.01)
A61K 45/06     (2006.01)
A61K 9/00      (2006.01)

(52) U.S. Cl.
CPC ........... A61K 31/715 (2013.01); A61K 45/06 (2013.01); C12N 5/0634 (2013.01); A61K 9/0019 (2013.01)

(58) Field of Classification Search
CPC ..................... A61K 31/715; C12N 5/0634
See application file for complete search history.

(56) References Cited

U.S. PATENT DOCUMENTS

| | | | |
|---|---|---|---|
| 4,775,626 A | 10/1988 | Armenta et al. | |
| 5,236,940 A | 8/1993 | Audiau et al. | |
| 5,571,900 A | 11/1996 | Wiegand et al. | |
| 5,679,654 A | 10/1997 | Tzianabos et al. | |
| 5,700,787 A * | 12/1997 | Tzianabos | A61K 39/02 514/54 |
| 6,358,939 B1 | 3/2002 | Hayes et al. | |
| 7,026,283 B2 | 4/2006 | Fleming et al. | |
| 7,026,285 B2 | 4/2006 | Tzianabos et al. | |
| 7,083,777 B1 | 8/2006 | Tzianabos et al. | |
| 7,384,645 B2 | 6/2008 | Foster et al. | |
| 7,629,330 B2 | 12/2009 | Wang et al. | |
| 8,206,726 B2 | 6/2012 | Kasper et al. | |
| 9,057,070 B2 | 6/2015 | Mazmanian et al. | |
| 9,265,790 B2 | 2/2016 | Tzianabos et al. | |
| 9,452,189 B2 | 9/2016 | Mazmanian et al. | |
| 9,539,281 B2 | 1/2017 | Kasper et al. | |
| 2002/0146396 A1 | 10/2002 | Albert et al. | |
| 2003/0044425 A1 | 3/2003 | Burt et al. | |
| 2003/0059462 A1 | 3/2003 | Barenholz et al. | |
| 2003/0147865 A1 | 8/2003 | Salomon et al. | |
| 2003/0147922 A1 | 8/2003 | Capiau et al. | |
| 2003/0219413 A1 | 11/2003 | Comstock et al. | |
| 2004/0063685 A1 | 4/2004 | Ilzawa et al. | |
| 2004/0092433 A1 | 5/2004 | Wang et al. | |
| 2004/0219160 A1 | 11/2004 | Tzianabos et al. | |
| 2005/0013831 A1 | 1/2005 | Foster et al. | |
| 2005/0020515 A1 | 1/2005 | Graff et al. | |
| 2005/0048587 A1 | 3/2005 | Rao et al. | |
| 2005/0063979 A1 | 3/2005 | Pickl et al. | |
| 2005/0119164 A1 | 6/2005 | Taylor et al. | |
| 2005/0147624 A1 | 7/2005 | Jennings et al. | |
| 2005/0181021 A1 | 8/2005 | Amb | |
| 2006/0029662 A1 | 2/2006 | Calias et al. | |
| 2006/0110412 A1 | 5/2006 | Desmons et al. | |
| 2006/0127387 A1 | 6/2006 | Zikria et al. | |
| 2006/0257852 A1 | 11/2006 | Rappuoli et al. | |
| 2006/0275752 A1 | 12/2006 | Sindhi | |
| 2006/0276378 A1 | 12/2006 | Wilson | |
| 2007/0041986 A1 | 2/2007 | Blaszczak et al. | |
| 2007/0154991 A1 | 7/2007 | Comstock et al. | |
| 2007/0207526 A1 | 9/2007 | Coit et al. | |
| 2008/0057565 A1 | 3/2008 | Comstock et al. | |
| 2008/0311140 A1 | 12/2008 | Lee et al. | |
| 2009/0017472 A1 | 1/2009 | Stuhlmuller et al. | |
| 2009/0124573 A1 | 5/2009 | Mazmanian et al. | |
| 2009/0252708 A1 | 10/2009 | Fitzpatrick et al. | |
| 2009/0317410 A1 | 12/2009 | Wang et al. | |
| 2009/0317427 A1 | 12/2009 | Kasper et al. | |

(Continued)

FOREIGN PATENT DOCUMENTS

| | | |
|---|---|---|
| CA | 2800174 | 11/2011 |
| CN | 1818061 | 8/2006 |

(Continued)

OTHER PUBLICATIONS

Taconic Farms, "Swiss Webster" mouse, available at https://www.taconic.com/mouse-model/swiss-webster; 9 total pages; obtained Jun. 26, 2019 (Year: 2019).*

Vázquez, M. et al., International Journal of Clinical Pharmacology and Therpaeutics, "Therapeutic drug monitoring of vancomycin in severe sepsis and septic shock", 2008, vol. 46, pp. 140-145. doi: 10.5414/CPP46140. (Year: 2008).*

Prucha, M. et al., Prague Medical Report, "Presence of Hypogammaglobulinemia—A risk factor of mortality in patients with severe sepsis, septic shock, and SIRS", 2013, vol. 114, No. 4, pp. 246-257 (Year: 2013).*

International Search Report for International Application PCT/US2016/037044 filed Jun. 10, 2016 on behalf of California Institute of Technology, dated Sep. 22, 2016. 4 pages.

(Continued)

Primary Examiner — Bahar Craigo
(74) Attorney, Agent, or Firm — Sheppard, Mullin, Richter & Hampton LLP

(57) ABSTRACT

Provided herein are methods and systems and related compositions comprising an effective amount of one or more zwitterionic polysaccharide possibly in combination with one or more antibiotics, for treatment and/or prevention of sepsis or a condition associated thereto in an individual.

20 Claims, 8 Drawing Sheets
Specification includes a Sequence Listing.

(56) References Cited

U.S. PATENT DOCUMENTS

| | | |
|---|---|---|
| 2010/0080760 A1 | 4/2010 | Hyde et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330166 A1 | 12/2010 | Ishida et al. |
| 2011/0002965 A1* | 1/2011 | Round .............. A61K 35/74 424/282.1 |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2013/0039949 A1 | 2/2013 | Mazmanian |
| 2013/0064859 A1 | 3/2013 | Mazmanian |
| 2013/0121966 A1 | 5/2013 | Mazmanian et al. |
| 2013/0195802 A1 | 8/2013 | Moore |
| 2014/0072534 A1 | 3/2014 | Mazmanian et al. |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |
| 2017/0003274 A1 | 1/2017 | Round et al. |
| 2018/0264026 A1 | 9/2018 | Round et al. |
| 2019/0022128 A1 | 1/2019 | Mazmanian et al. |
| 2020/0197436 A1 | 6/2020 | Round et al. |

FOREIGN PATENT DOCUMENTS

| | | |
|---|---|---|
| DE | 3704389 | 8/1988 |
| EP | 371414 | 6/1990 |
| EP | 382576 | 8/1991 |
| EP | 497524 | 8/1992 |
| EP | 1358885 | 11/2003 |
| EP | 1459757 | 9/2004 |
| EP | 2217250 | 8/2010 |
| EP | 2422200 | 8/2010 |
| EP | 2555753 | 10/2011 |
| EP | 2571982 | 11/2011 |
| EP | 2764090 | 8/2014 |
| EP | 2994161 | 3/2016 |
| GB | 2286193 | 8/1995 |
| HK | 1201291 | 8/2015 |
| JP | S56128721 | 10/1981 |
| JP | H10507746 | 7/1998 |
| JP | 2002540074 | 11/2002 |
| JP | 2002541113 | 12/2002 |
| JP | 2003204796 | 7/2003 |
| JP | 2004536028 | 12/2004 |
| JP | 2006522135 | 9/2006 |
| JP | 2010059201 | 3/2010 |
| JP | 2012524910 | 10/2012 |
| JP | 2016521284 | 7/2016 |
| JP | 6027961 | 11/2016 |
| JP | 6296367 | 3/2018 |
| JP | 6471888 | 2/2019 |
| WO | WO199531990 | 11/1995 |
| WO | WO199607427 | 3/1996 |
| WO | WO199632119 | 10/1996 |
| WO | WO199635433 | 11/1996 |
| WO | WO199842718 | 10/1998 |
| WO | WO199845335 | 10/1998 |
| WO | WO200001733 | 1/2000 |
| WO | WO2000059515 | 10/2000 |
| WO | WO200207741 | 1/2002 |
| WO | WO2002045708 | 6/2002 |
| WO | WO2003075953 | 9/2003 |
| WO | WO2003077863 | 9/2003 |
| WO | WO2003095606 | 11/2003 |
| WO | WO2004050909 | 6/2004 |
| WO | WO2004089407 | 10/2004 |
| WO | WO2005010215 | 2/2005 |
| WO | WO2005094571 | 10/2005 |
| WO | WO2007040446 | 4/2007 |
| WO | WO2007092451 | 8/2007 |
| WO | WO2008095141 | 8/2008 |
| WO | WO2009062132 | 5/2009 |
| WO | WO2009149149 | 12/2009 |
| WO | WO2010124256 | 10/2010 |
| WO | WO2011056703 | 5/2011 |
| WO | WO2011127302 | 10/2011 |
| WO | WO2011146910 | 11/2011 |
| WO | WO2011153226 | 12/2011 |
| WO | WO2012027032 | 3/2012 |
| WO | WO2012103532 | 8/2012 |
| WO | WO2013009945 | 1/2013 |
| WO | WO2013019896 | 2/2013 |
| WO | WO2013036290 | 3/2013 |
| WO | WO2013052099 | 4/2013 |
| WO | WO2014182966 | 11/2014 |

OTHER PUBLICATIONS

Written Opinion for International Application PCT/US2016/037044 filed Jun. 10, 2016 on behalf of California Institute of Technology, dated Sep. 22, 2016. 8 pages.

Kalka-Moll, W.M. et al., "Immunochemical and Biological Characterization of Three Capsular Polysaccharides from a Single Bacteroides Fragilis Strain", Infection and Immunity, vol. 69, No. 4, pp. 2339-2344, (2001).

Mazmanian, S.K., et al., "An Immunomodulatory Molecule of Symbiotic Bacteria Directs Maturation of the Host Immune System", Cell, vol. 122(1), pp. 107-118, (2005).

Tzianabos, A.O. et al., "Protection Against Experimental Intraabdominal Sepsis by Two Polysaccharide Immunomodulators", The Journal of Infectious Diseases, vol. 178, pp. 200-206, (1998).

Wang, Y. et al., "Structural Basis of the Abscess-Modulating Polysaccharide A2 From Bacteroides Fragilis", Proc. Natl. Acad. Sci. U.S.A., vol. 97, No. 5, pp. 13478-13483, (2000).

Zouali, M. et al., "Marginal Zone B-Cells, A Gatekeeper of Innate Immunity", Frontiers in Immunology, vol. 2, Article 63, 10 pages, (2011).

"Asthma" from the Centers for Disease Control and Prevention, [retrieved Nov. 13, 2012], Retrieved from the Internet www.cdc.gov/asth ma/aag/2010/overview.html.

"Ulcerative Colitis" from the National Institutes of Health [online], [retrieved Nov. 9, 2012], Retrieved from the Internet www.digestive.niddk.nih.gov/ddiseases/pubs/colitis/UlcerativeColitis508.pdf.

[No Author Listed] "MS the Disease". National Multiple Sclerosis Society. Downloaded from the internet at http://www.nationalmssociety.org/About-the-Society/Press-Room/MS-the-Disease on Dec. 19, 2016, 4 pages (website copyright 2014).

[No Author Listed] Drug Absorption, Bioavailability, and Routes of Administration. Goodman & Oilman's The Pharmacological Basis of Therapeutics, Tenth Edition, McGraw-Hill Medical Publishing Edition, New York, 2001, pp. 5-8.

[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.

Abreu, M.T. et al. "Measurement of vitamin D levels in inflammatory bowel disease patients reveals a subset of Crohn's disease patients with elevated 1,25-dihydroxyvitamin D and low bone mineral density" Gut, 2004, 53(8) pp. 1129-1136.

"Abscess" from Wikipedia, dated May 9, 2015 (6 pages) https://en.wikipedia.org/Wiki/Abscess.

Adams JS, et al. (2008) Unexpected actions of vitamin D: new perspectives on the regulation of innate and adaptive immunity. Nat Clin Pract Endocrinol Metab 4: 80-90.

Adams JS, et al. (2012) Extrarenal expression of the 25-hydroxyvitamin D-1-hydroxylase. Archives of biochemistry and biophysics 523: 95-102.

Adkins et al., "Exclusive Th2 Primary Effector Function in Spleens but Mixed Th1/Th2Function in Lymph Nodes of Murine Neonates" Journal Immunol, Mar. 1, 2000, pp. 2347-2353, 164(5).

Adkins et al.,"Early Block in Maturation Is Associated with Thymic Involution in Mammary Tumor-Bearing Mice", J Immunology, Jun. 1, 2000, pp. 5635-5640, vol. 164, Issue 11.

Adkins, "T-cell function in newborn mice and humans", Review Immunology Today, Jul. 1, 1999, pp. 330-335, vol. 20, Issue 7.

(56) References Cited

OTHER PUBLICATIONS

Adkins, "Development of neonatal Th1/Th2 function", Int Rev Immunol, 2000; pp. 157-171, 19 (2-3), Taylor and Francis Group, Abingdon, United Kingdom.
Advisory Action for U.S. Appl. No. 13/112,725, filed May 20, 2011 on behalf of June L. Round, dated Mar. 4, 2014. 3 pages.
Afzali, "The role of T helper 17 (Th17) and regulatory! cells (Treg) in human organ transplantation and autoimmune disease", Clinical and Experimental Immunology, Apr. 2007, pp. 32-46, vol. 148, Issue 1.
Aharoni et al., Bystander suppression of experimental autoimmune encephalomyelitis by T cell lines and clones ofthe type induced by copolymer 1. J Neuroimmunol. Nov. 2, 1998;91(1-2):135-46.
Aharoni et al., Copolymer 1 induces T cells ofthe T helpertype that crossreact with myelin basic protein and suppress experimental autoimmune encephalomyelitis. Proc Natl Acad Sci USA. Sep. 30, 1997;94(20):10821-6.
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Al-Bader et al. "Activation of Human Dendritic Cells Is Modulated by Components ofthe Outer Membranes of Neisseria meningitidis" Infection and Immunity. Oct. 2003; 71(10): 5590-5597).
Allen AC, et al. (2012) "A pilot study ofthe immunological effects of high-dose vitamin Din healthy volunteers". Multiple Sclerosis Journal; 2012; vol. 18; No. 12; pp. 1797-1800.
Amidon et al., "Proposed New USP General Information Chapter, Excipient Performance <1059>", Pharmacopeia forum, Nov.-Dec. 2007, pp. 1311-1323, vol. 33(6), The United States Pharmacopeia Convention, Rockville, MD.
Amsen et al., "Instruction of distinct CD4 T helper cell fates by different notch ligands on antigen-presenting cells", Cell, May 14, 2004, pp. 515-526, vol. 117, Issue 4.
Anderson AC, et al. (2012) A transgenic model of central nervous system autoimmunity mediated by CD4+ and CD8+ T and B cells. Journal of immunology 188: 2084-2092.
Arnon et al., New insights into the mechanism of action of copolymer 1 in experimental allergic encephalomyelitis and multiple sclerosis. J Neural. Apr. 1996;243(4 Suppl I):S8-13. Review.
Asadullah et al., Interleukin-10 therapy-review of a new approach. Pharmacol Rev. Jun. 2003;55(2):241-69.
Ascherio A, et al. "Vitamin D and multiple sclerosis". Lancet Neurology; Jun. 2010; vol. 9: pp. 599-612.
Asseman et al., "An essential role for interleukin 10 in the function of regulatory T cells that inhibit intestinal inflammation", J Exp Med., Oct. 4, 1999, pp. 995-1004, 190 (7).
Atarashi et al., "ATP drives lamina propria TH17 cell differentiation", Nature, Oct. 9, 2008, pp. 808-812, vol. 455, Issue 7214.
Awasthi, "Interplay between effector Th17 and regulatory T cells", J Clin Immunol, Nov. 2008, pp. 660-670, 28(6), Springer International Publishing AG, Cham, Switzerland.
Azzawi et al., Identification of activated T lymphocytes and eosinophils in bronchial biopsies instable a topic asthma. Am Rev Respir Dis. Dec. 1990; 142(6 Pt 1):1407-13.
Bach, The effect of infections on susceptibility to autoimmune and allergic diseases, N Engl J Med., Sep. 19, 2002, pp. 911-920, vol. 347, No. 12.
Baecher-Allan CM, et al. (2011) CD2 costimulation reveals defective activity by human CD4+CD25(hi) regulatory cells in patients with multiple sclerosis. Journal of immunology 186: 3317-3326.
Banerjee et al. "Expansion of FOXP3 high regulatory T cells by human dendritic cells (DCs) in vitro and after injection of cytokine-matured DCs in myeloma patients" Blood. 2006; 108: 2655-2661.
Baranzini SE, et al. (2010) Genome, epigenome and RNA sequences of monozygotic twins discordant for multiple sclerosis. Nature 464: 1351-1356.
Barnes, M.J., et al. (2009). "Regulatory T cells reinforce intestinal homeostasis". Immunity 31, 401-411.

Bar-On L, et al. (2010) Defining in vivo dendritic cell functions using CD11c-DTR transgenic mice. Methods in molecular biology 595: 429-442.
Barrat FJ, et al. (2002) In vitro generation of interleukin 10-producing regulatory CD4(+) T cells is induced by immunosuppressive drugs and inhibited by T helper type 1 (Th1)- and Th2-inducing cytokines. J Exp Med 195: 603-616.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.
Batta et al., Conformational stabilization of the altruronic acid residue in the O-specific polysaccharide of Shigella sonnei/Plesiomonas shigelloides. Carbohydr Res. Dec. 1998;305(1):93-9.
Bayley DP et al. Analysis of cepA and other Bacteroides fragilis genes reveals a unique promoter structure. (2000) FEMS Microbial Lett 193:149-54.
Bazan et al., Unraveling the structure of IL-2. Science. Jul. 17, 1992;257(5068):410-3.
Becker et al., "TGF-Suppresses Tumor Progression in Colon Cancer by Inhibition of IL-6 trans-Signaling," Immunity, vol. 21, 491-501 (2004).
Becker KG, et al. (1998) Clustering of non-major histocompatibility complex susceptibility candidate loci in human autoimmune diseases. Proc Natl Acad Sci U S A 95: 9979-9984.
Belkaid et al., "Regulatory T cells in the control of host-microorganism interactions", Annu. Rev. Immunol., 2009. pp. 551-589, vol. 27.
Bell, "Function of CD4 T cell subsets in vivo: expression of CD45R isoforms", Semin Immune, Feb. 1, 1992, pp. 43-50, 14(1).
Berer et al., Commensal gut flora and brain autoimmunity: a love or hate affair? Acta Neuropathol. May 2012;123(5):639-51. doi: 10.1007/s00401-012-0949-9. EpubFeb. 10, 2012.
Berer et al., Commensal microbiota and myelin autoantigen cooperate to trigger autoimmune demyelination. Nature. Oct. 26, 2011;479(7374):538-41. doi: 10.1038/nature10554.
Berggren et al., Decreasing serum concentrations of all-trans, 13-cis retinoic acids and retinal during fasting and caloric restriction. J Intern Med. Mar. 2003;253(3):375-80.
Bernatowska-Matuszkiewicz et al., IgG subclasses and antibody response to pneumococcal capsular polysaccharides in children with severe sinopulmonary infections and asthma. Immunol Investi. 1991;20(2):173-185.
Bettelli E, et al. (2003) Myelin oligodendrocyte glycoprotein-specific T cell receptor transgenic mice develop spontaneous autoimmune optic neuritis. The Journal of experimental medicine 197: 1073-1081.
Bettelli, E. et al. "Reciprocal developmental pathways for the generation of pathogenic effector TH17 and regulatory T cells" Nature vol. 441 pp. 235-238 (2006).
Bhaduri et al., Simple and rapid method for disruption of bacteria for protein studies. Appl Environ Microbial. Oct. 1983;46(4):941-3.
Bhat R, et al. (2009) Innate and adaptive autoimmunity directed to the central nervous system. Neuron 64: 123-132.
Bilo et al., "Diagnosis of Hymenoptera venom allergy", Allergy, Nov. 2005, pp. 1339-1349, vol. 60, Issue 11.
Blander et al., Toll-dependent selection of microbial antigens for presentation by dendritic cells. Nature. Apr. 6, 2006;440(7085):808-12. Epub Feb. 19, 2006.
Blomfield et al. Lrp stimulates phase variation of type 1 fimbriation in E. coli K12. J. Bacteriology 175, 27-36, 1993.
Blumberg & Powrie, "Microbiota, Disease, and Back to Health: A Metastable Journey," Sci. Transl. Med., vol. 4, 137rv7 (2012).
Boguniewicz, "The autoimmune nature of chronic urticarial", Allergy and Asthma Proceedings, Sep.-Oct. 2008, pp. 433-438, vol. 29, No. 5.
Bollrath et al., "gp130-Mediated Stat3 Activation in Enterocytes Regulates Cell Survival and Cell-Cycle Progression during Colitis-Associated Tumorigenesis," Cancer Cell, vol. 15, 91-102 (2009).

(56) References Cited

OTHER PUBLICATIONS

Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.

Bouma et al., "The immunological and genetic basis of inflammatory bowel disease", Nat. Rev. Immunol., 2003, pp. 521-533, 3.

Bouskra, D., et al. (2008). Lymphoid tissue genesis induced by commensals through NOD1 regulates intestinal homeostasis. Nature 456, 507-510.

Braat et al., "A Phase I Trial With Transgenic Bacteria Expressing interleukin-10 in Crohn's Disease" Clinical Gastroenterology and Hepatology, Jun. 2006, pp. 754-759, vol. 4, Issue 6.

Braun et al., "Body traffic: ecology, genetics, and immunity in inflammatory bowel disease", Annu Rev Pathol., Feb. 28, 2007, pp. 401-429, vol. 2.

Bregenholt, "S. Cells and cytokines in the pathogenesis of inflammatory bowel disease: new insights from mouse T Cell transfer models", Exp Clin Immunogenet, Jun. 2000, pp. 115-129, vol. 17, No. 3, S. Karger AG, Basel, Switzerland.

Brichford, Can You Prevent Multiple Sclerosis? Understanding factors that increase your risk of multiple sclerosis and what—if anything—you can do about them. EverydayHealth.com. Dec. 2008; 2 pages.

Brubaker et al., Mitogenic activity of purified capsular polysaccharide A from Bacteroides fragilis: differential stimulatory effect on mouse and rat lymphocytes in vitro. J Immunol. Feb. 15, 1999; 162(4):2235-42.

Bruce D, et al. (2011) Converging pathways lead to overproduction of IL-17 in the absence of vitamin D signaling. International immunology 23: 519-528.

Brunkow, M.E., et al., "Disruption of a new forkhead/winged-helix protein, scurfin, results in the fatal lymphoproliferative disorder of the scurfy mouse" Nat Genet 27, 68-73 (2001).

Budinger et al., Immunologic mechanisms in hypersensitivity reactions to metal ions: an overview. Allergy. Feb. 2000;55(2):108-15. Review.

Burgers et al., The challenges of HIV vaccine development and testing. Best Pract Res Clin Obstet Gynaecol. Apr. 2005;19(2):277-91.

Byers et al., "Mechanism of action of vitamin D and the vitamin D receptor in colorectal cancer prevention and treatment," Rev. Endocr. Metab. Disord. Mar. 2012, pp. 31-38, vol. 13, Issue 1, Springer, Berlin, Germany.

Cabrera R, et al. (2010) Influence of serum and soluble CD25 (sCD25) on regulatory and effector T-cell function in hepatocellular carcinoma. Scandinavian journal of immunology 72: 293-301.

Cahill et al., "Inflammatory bowel disease: an immunity-mediated condition triggered by bacterial infection with Helicobacter hepaticus", Infect Immun., Aug. 1997, pp. 3126-3131, vol. 65 No. 8.

Campbell et al. The vitamin D receptor as a therapeutic target in Expert Opinion Ther. Targets, 2006; vol. 10; pp. 735-748.

Cantorna et al. "Vitamin D status, 1,25-dihydroxyvitamin D3, and the immune system" (Am. J. Clin. Nutr. 80(suppl):1717S-20S, 2004).

Cantorna MT, et al. (1996) "1,25-Dihydroxyvitamin D3 reversibly blocks the progression of relapsing encephalomyelitis, a model of multiple sclerosis". Proceedings of the National Academy of Sciences of the United States of America 93: 7861-7864.

Catorna, M.T. et al. 1,25-Dihydroxycholecalciferol prevents and ameliorates symptoms of experimental murine inflammatory bowel disease. J. Nutr. 2000 130(11) oo.2648-52.

Cash, H.L., et al. (2006). Symbiotic bacteria direct expression of an intestinal bactericidal lectin. Science 313, 1126-1130.

Chambers E. et al. (2011) The impact of vitamin D on regulatory T cells. Curr. Allergy Asthma Rep 11: 29-36.

Chang JH, et al. (2010) "1,25-Dihydroxyvitamin D3 inhibits the differentiation and migration of T(H)17 cells to protect against experimental autoimmune encephalomyelitis." PLoS One 5: e12925. 12 pages.

Chatila et al., Role of regulatory T cells in human diseases. J Allergy Clin Immunol. Nov. 2005;116(5):949-59; quiz 960.

Chen et al., "Delivery of foreign antigens by engineered outer membrane vesicle vaccines", Proc Natl Acad Sci USA, Feb. 16, 2010, pp. 3099-3104, 107 (7), National Academy of Sciences.

Chen et al. "Pertussis Toxin by Inducing IL-6 Promotes the Generation of IL-17-Producing CD4 Cells". Journal of Immunology, May 15, 2007, pp. 6123-6129, vol. 178, No. 10.

Chen J et al., DNA inversion on conjugative plasmid pVT745. J Bacterial. Nov. 2002; 184(21):5926-34.

Cho et al., "Recent Insights Into the Genetics of Inflammatory Bowel Disease", Gastroenterology, May 2011, pp. 1704-1712, vol. 140.

Chow J, et al. (2009) Getting the bugs out of the immune system: do bacterial microbiota "fix" intestinal T cell responses? Cell Host Microbe 5: 8-12.

Clemente et al., "Infliximab modifies mesenteric adipose tissue alterations and intestinal inflammation in rats with TNBS-induced colitis," Scand. J. Gastroenterol., vol. 47, 943-50 (2012).

Cobb et al., Zwitterionic capsular polysaccharides: the new MHCII-dependent antigens. Cell Microbial. Oct. 2005;7(10): 1398-403. Review.

Collison et al., The inhibitory cytokine IL-35 contributes to regulatory T-cell function. Nature. Nov. 22, 2007;450(7169):566-9.

Communication pursuant to Article 94(3) EPC for European Application No. 08847489.5 filed in the name of California Institute of Technology, dated Aug. 7, 2013.

Comstock et al. Analysis of a capsular polysaccharide biosynthesis locus of Bacteroides fragilis. (1999) Infect Immun 67:3525-32.

Comstock et al., Bacterial glycans: key mediators of diverse host immune responses. Cell. Sep. 8, 2006;126(5):847-50.

Comstock et al., Interstrain variation of the polysaccharide B biosynthesis locus of Bacteroides fragilis: characterization of the region from strain 638R. J Bacterial. Oct. 1999 ;181(19):6192-6.

Conesa et al., Interleukin-2 induces peroxide production by primed normodense eosinophils of patients with asthma. Allergy Asthma Proc. Jan.-Feb. 2003;24(1):27-33.

Coombes et al., "Regulatory T cells and intestinal homeostasis", Immunol. Rev., Apr. 2005, pp. 184-194, vol. 204, Issue 1.

Coombes JL, et al. (2007) Control of intestinal homeostasis by regulatory T cells and dendritic cells. Semin Immunol 19: 116-126.

Coombes, JL, et al. (2007). A functionally specialized population of mucosal CD103+ DCs induces Foxp3+ regulatory T cells via a TGF-beta and retinoic acid-dependent mechanism. J Exp Med 204, 1757-1764.

Correale J, et al. (2011) Vitamin D-mediated immune regulation in multiple sclerosis. Journal of the neurological sciences 311: 23-31.

Couper et al. "IL-10: The Master Regulator of Immunity to Infection" Journal of Immunology. 2008; 180:5771-5777.

Coussens & Werb, "Inflammation and cancer," Nature, vol. 420, 860-867 (2002).

Coyne et al., "Mpi recombinase globally modulates the surface architecture of a human commensal bacterium", PNAS, Sep. 2, 2003, pp. 10446-10451, vol. 100 No. 18.

Coyne et al., "Polysaccharide biosynthesis locus required for virulence of Bacteroides fragilis", Infect. Immun., Jul. 2001, pp. 4342-4350, vol. 69, No. 7.

Coyne, M.J. et al., "Bacteroides fragilis NCTC9343 Produces at Least Three Distinct Capsular Polysaccharides: Cloning, Characterization, and Reassignment of Polysaccharide Band C Biosynthesis Loci", Infection and Immunity, Nov. 2000, p. 6176-6181.

Crabb et al., T cell regulation of Bacteroides fragilis-induced intraabdominal abscesses. Rev Infect Dis. Jan.-Feb. 1990;12 Suppl 2:S1 78-84. Review.

Craig, Autologous hematopoietic stem cell transplantation for Crohn's disease. Autoimmun Rev. Aug. 2002;1(4):244-9. Review.

Dadley-Moore, The sweet side of maturation. Nature Rev Immunol. Sep. 2005;5:674.

Dahiyat BI. et al., De nova protein design: fully automated sequence selection. Science (1997) 278:82-87.

Daniel et al. Immune Modulatory Treatment of Trinitrobenzene Sulfonic Acid Colitis with Calcitriol is Associated with a Change of

(56) References Cited

OTHER PUBLICATIONS a T Helper (Th) 1/1 Th17 to a Th2 and Regulatory T Cell Profile, in J. Pharmacology and Experimental Therapeutics, 2008, vol. 324, pp. 23-33.
Decision on Rejection for JP2010-533311 dated Oct. 29, 2013 in the name of California Institute of Technology. (English Translation+ Japanese Original).
Decision of Refusal dated Feb. 26, 2016 in Japanese Patent Application No. 2013-503958.
Decision of Refusal dated Nov. 27, 2018 in Japanese Patent Application No. 2016-513092.
Definition of "prevention" from the Institute for International Medical Education [online], [Retrieved on Mar. 24, 2011], Retrieved from the internet, www.iime.org/glossary.htm. Published Feb. 2002, p. 1, 2, 26, 27 and 39.
Deib, Treating multiple sclerosis with monoclonal antibodies: a 2013 update. Expert Rev Neurother. Mar. 2013;13(3):313-35. doi: 10.1586/ern.13.17.
Denning, T. et al. "Lamina propria macrophages and dendritic cells differentially induce regulatory and interleukin 17-producing T cell responses" Nature Immunology; vol. 8; No. 10; Oct. 1, 2007; pp. 1086-1094.
Deslongchamps et al., "Ozonolysis of Acetals. (1) Ester Synthesis, (2) THP Ether Cleavage, (3) Selective Oxidation of B-Glycoside, (4) Oxidative Removal of Benzylidene and Ethylidene Protecting Groups". Canadian J of Chem. 1971;49:2465-2467.
Deslongchamps et al., The Importance of Conformation in the Ozonolysis of Acetals. Canadian J Chem. 1972;50:3402-3404.
Deslongchamps et al., The Oxidation of Acetals by Ozone. Canadian J Chem. 1974;52:3651-3664.
Dethlefsen et al. "An ecological and evolutionary perspective on human-microbe mutualism and disease", Nature, Oct. 18, 2007, pp. 811-818, 449.
Dias et al., Antisense oligonucleotides: Basic concepts and mechanisms. Mol. Cancer Therap., 2002, vol. 1: 347-355.
Difabio et al., Structure of the Capsular Polysaccharide Antigen of Type IV Group B *Streptococcus*; Can. J. Chem. 67:877 (1989).
Dohi et al., "Type 1 and 2 T helper cell-mediated colitis", Current Opinion in Gastroenterology, Nov. 2006, pp. 651-657, vol. 22—Issue 6, Lippincott Williams & Wlkins, Philadelphia, PA.
Doig et al., The efficacy of the heat killing of *Mycobacterium tuberculosis*. J Clin Pathol. Oct. 2002;55(10):778-9.
Dong, "Diversification of T-helper-cell lineages: finding the family root of IL-17-producing cells", Nat Rev Immunol, Mar. 17, 2006, pp. 329-334, vol. 6, Issue 4.
Dooms et al., Revisiting the role of IL-2 in autoimmunity. Eur J Immunol. Jun. 2010;40(6):1538-40. doi: 10.1002/eji.201040617.
Duerr, R.H. et al. Science vol. 314; 2006; pp. 1461.
Eisenstein et al. Integration host factor is required for the DNA inversion that controls phase variation in *E.coli*. Proc Natl. Acad. Sci. 84, 6506-6510, 1987.
Elson et al., "Monoclonal anti-interleukin 23 reverses active colitis in a T cell-mediated model in mice", Jun. 2007, pp. 2359-2370, vol. 132, Issue 7.
Elson, "Commensal bacteria as targets in Crohn's disease" Gastroenterology Jul. 2000, pp. 254-257, vol. 119, Issue 1.
European Communication pursuant to Article 94(3) EPC dated Feb. 5, 2014 for European application 10767863.3 filed on Apr. 23, 2010 in the name of California Institute of Technology. 7 pages.
European Communication pursuant to Rules 70(2) and 70a(2) EPC dated Dec. 27, 2010 for European application 08847489.5 filed on Nov. 9, 2008 in the name of California Institute of Technology. 7 pages.
European Communication pursuant to Rules 70(2) and 70a(2) EPC dated Feb. 12, 2013 for European application 10767863.3 filed on Apr. 23, 2010 in the name of California Institute of Technology. 1 page.
Extended European Search Report for European Application No. 10767863.3 dated Jan. 24, 2013. 10 pages.
European Search Report dated Jan. 30, 2015 for European application 10767863.3 filed on Apr. 23, 2010 in the name of California Institute of Technology. 5 pages.
Extended European Search Report for the European Application No. 11784368.0, dated Dec. 2, 2013, 13 pages.
Examination Report dated May 5, 2017 in European Application No. 08847489.
Examination Report for European patent application No. 11784368.0, dated Jul. 8, 2016. 7 pages.
Examination Report dated Jan. 24, 2018 in European Patent Application No. 147952048.
Examination Report dated Jan. 18, 2019 in European Patent Application No. 147952048.
Examination Report dated Sep. 23, 2014 in European Patent Application No. 11766746.9.
Examination Report dated Nov. 10, 2015 in European Patent Application No. 11766746.9.
Extended European Search Report dated Sep. 13, 2013 in European Application No. 11766746.9.
Extended European Search Report dated Dec. 8, 2018 in European Application No. 08847489.
Extended European Search Report for Application No. 12811896.5, dated Jun. 1, 2015. 11 pages.
Extended European Search Report for European Application No. 12837738.9 dated Mar. 18, 2015 8 pages.
Extended European Search Report for European Application No. 14795204.8, dated Dec. 8, 2016, 9 pages.
Falk, P.G., et al. (1998). Creating and maintaining the gastrointestinal ecosystem: what we know and need to know from gnotobiology. Microbiol Mol Biol Rev 62, 1157-1170.
Feuerer et al., "Foxp3+ regulatory T cells: differentiation, specification, subphenotypes", Nat Immunol., Jun. 18, 2009, p. 689-695, vol. 10, Issue 7.
Final Office Action issued in U.S. Appl. No. 10/814,620, filed Mar. 31, 2004 in the name of Arthur O. Tzianabos, dated Oct. 7, 2009.
Final Office Action for U.S. Appl. No. 12/267,602, filed Nov. 9, 2008 on behalf of Sarkis K. Mazmanian et al, dated Feb. 6, 2012. 15 pages.
Final Office Action for U.S. Appl. No. 12/766,787, filed Apr. 23, 2010 on behalf of June L. Round et al, dated Aug. 4, 2015. 29 pages.
Final Office Action for U.S. Appl. No. 12/766,787, filed Apr. 23, 2010 on behalf of June L. Round et al, dated Nov. 26, 2012. 12 pages.
Final Office Action for U.S. Appl. No. 12/831,131, filed Jul. 6, 2010 on behalf of June L. Round et al, dated Jun. 10, 2013. 23 pages.
Final Office Action for U.S. Appl. No. 13/082,183, filed Apr. 7, 2011 on behalf of Yue Shen et al, dated Jan. 9, 2014. 9 pages.
Final Office Action for U.S. Appl. No. 13/112,725, filed May 20, 2011 on behalf of June L. Round, dated Jan. 7, 2015. 15 pages.
Final Office Action for U.S. Appl. No. 13/112,725, filed May 20, 2011 on behalf of June L. Round, dated Oct. 24, 2013. 8 pages.
Final Office Action for U.S. Appl. No. 13/112,725, filed May 20, 2011 on behalf of California Institute of Technology, dated Nov. 2, 2016. 29 Pages.
Final Office Action for U.S. Appl. No. 13/360,702, filed Jan. 28, 2012 on behalf of Sarkis K. Mazmanian et al, dated Dec. 3, 2013. 14 pages.
Final Office Action for U.S. Appl. No. 13/464,876, filed May 4, 2012 on behalf of Sarkis K. Mazmanian et al, dated Feb. 20, 2014. 20 pages.
Final Office Action for U.S. Appl. No. 13/573,695 filed Oct. 3, 2012 on behalf of Sarkis K. Mazmanian et al, dated Jan. 28, 2014. 12 pages.
Final Office Action dated Dec. 28, 2017 in U.S. Appl. No. 14/660,827.
Final Office Action dated Jun. 15, 2018 in U.S. Appl. No. 14/264,607.
Final Office Action dated Oct. 22, 2018 in U.S. Appl. No. 14/803,598.
Final Office Action dated Sep. 16, 2020 in U.S. Appl. No. 16/386,522.
Finberg et al., Decay-accelerating factor expression on either effector or target cells inhibits cytotoxicity by human natural killer cells. J Immunol. Sep. 15, 1992;149(6):2055-60.
Fink, et al. "Human antigen-presenting cells respond differently to gut-derived probiotic bacteria but mediate similar strain-dependent

(56) References Cited

OTHER PUBLICATIONS

NK and T cell activation" FEMS Immunology and Medical Microbiology, 2007, vol. 51, No. 3; pp. 535-546.
Fontenot et al., "Regulatory T cell lineage specification by the forkhead transcription factorfoxp3", Immunity, Mar. 2005, pp. 329-341, vol. 22, Issue 3.
Fontenot, J.D., et al. (2003). Foxp3 programs the development and function of CD4+CD251 + regulatory T cells. Nat Immunol 4, 330-336.
Fournier et al., Isolation of type 5 capsular polysaccharide from *Staphylococcus aureus*. Ann Inst Pasteur Microbial. Sep.-Oct. 1987;138(5):561-7.
Frank et al., "Molecular-phylogenetic characterization of microbial community imbalances in human inflammatory bowel diseases", Proc Natl Acad Sci USA, Aug. 21, 2007, pp. 13780-13785, vol. 104 No. 34.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class 11 MHC molecules. Int Immunol. May 1999;11(5):635-41.
Fridkis-Hareli et al., Direct binding of myelin basic protein and synthetic copolymer 1 to class 11 major histocompatibility complex molecules on living antigen-presenting cells—specificity and promiscuity. Proc Natl Acad Sci USA. May 24, 1994;91(11):4872-6.
Fridkis-Hareli et al., Synthetic copolymer 1 and myelin basic protein do not require processing prior to binding to class 11 major histocompatibility complex molecules on living antigen-presenting cells. Cell Immunol. Jul. 1995;163(2):229-36.
Froicu, M. et al. "A crucial role for the vitamin D receptor in experimental inflammatory bowel diseases" Mol. Endocrinol, 2003. 17(12) oo.2386-2392.
Froicu, M., et al. Vitamin D receptor is required to control gastrointestinal immunity in IL-10 knockout mice. Immunology, 2006. 117(3) p. 310-8.
Fujino et al., "Increased expression of interleukin 17 in inflammatory bowel disease", Gut, 2003; pp. 65-70, 52, BMJ Publishing Group, London, United Kingdom.
Gaboriau-Rauthiau et al., "The key role of segmented filamentous bacteria in the coordinated maturation of gut helper T cell responses", Immunity, Oct. 16, 2009, pp. 677-689,vol. 31, Issue 4.
Gallorini, et al., "Toll-like receptor 2 dependent immunogenicity of glycoconjugate vaccines containing chemically derived zwitterionic polysaccharides," PNAS vol. 106: 17481-17486.Oct. 13, 2009. 6 Pages.
Gally DL et al. Environmental regulation of the fim switch controlling type 1 fimbrial phase variation in *Escherichia coli* K-12: effects of temperature and media. (1993) J Bacteriol 175:6186-93.
Garrett et al., "Colitis-Associated Colorectal Cancer Driven by T-bet Deficiency in Dendritic Cells," Cancer Cell, vol. 16, 208-19 (2009).
Garrett et al., "Enterobacteriaceae Act in Concert with the Gut Microbiota to Induce Spontaneous and Maternally Transmitted Colitis," Cell Host Microbe, vol. 8, 292-300 (2010).
Gelu-Simeon, et al., Evaluation and predictive factors of thyroid disorder due to interferon alpha in the treatment of hepatitis C. World J Gastroenterol 2009; 15(3):328-333.
GenBank Accession No. AJ277832; Hutloff Jan. 19, 2001.
GenBank Accession No. CAC06612; Hutloff Jan. 19, 2001.
GenBank Accession No. NM012092; Dec. 20, 2003.
GenBank Accession No. NP036224; Dec. 20, 2003.
Gerard et al., "Interleukin 10 reduces the release of tumor necrosis factor and prevents lethality in experimental endotoxemia", J. Exp. Med., Feb. 1, 1993, pp. 547-550, 177 (2): 547.
Gibson 111 et al., The capsular polysaccharide complex of Bacteroides fragilis induces cytokine production from human and murine phagocytic cells. Infect Immun. Mar. 1996;64(3): pp. 1065-1069.

Gibson et al., "Chapter 5: trans-Galactooligosaccharides as Prebiotics". Handbook of Functional Dairy Products. Edited by Colette Shortt and John O'Brien. Published by CRC Press. 2004. 18 pages.
Gilbert et al., "Toward Effective Probiotics for Autism and other Neurodevelopmental Disorders", Cell, Dec. 19, 2013, pp. 1446-1448,vol. 155, Issue 7.
Gill et al., "Metagenomic analysis of the human distal gut microbiome", Science, Jun. 2, 2006, pp. 1355-1359, vol. 312, Issue 5778.
Glazebrook et al., A novel exopolysaccharide can function in place of the calcofluor-binding exopolysaccharide in nodulation of alfalfa by Rhizobium meliloti. Cell. Feb. 24, 1989;56(4):661-672.
Golgher et al., Galactofuranose-containing glycoconjugates of epimastigote and trypomastigote forms of Trypanosoma cruzi. Mol Biochem Parasitol. Aug. 1993;60(2):249-64.
Gondek, D.C., et al. (2005). Cutting edge: contact-mediated suppression by CD4+CD25+ regulatory cells involves a granzyme B-dependent, perforin-independent mechanism. J. Immunol.; vol. 174, 1783-1786.
Gonzalez-Hernandez et al., Peripheral blood CD161 + T cells from asthmatic patients are activated during asthma attack and predominantly produce IFN-gamma. Scand J Immunol. Apr. 2007;65(4):368-75.
Goverman J (2009) Autoimmune T cell responses in the central nervous system. Nat Rev Immunol 9: 393-407.
Goverman J, et al. (1993) Transgenic mice that express a myelin basic protein-specific T cell receptor develop spontaneous autoimmunity. Cell 72: 551-560.
Grabow, Bacteriophages: Update on application as models for viruses in water. Water SA 2001;27(2):251-268.
Greenberger, Drug allergy, J Allergy Clin Immunol, Feb. 2006, pp. S464-S470, vol. 117, Issue 2, Supplement 2.
Grivennikov et al., "IL-6 and Stat3 Are Required for Survival of Intestinal Epithelial Cells and Development of Colitis-Associated Cancer," Cancer Cell, vol. 15, 103-113 (2009).
Groux et al., "A CD4+ T-cell subset inhibits antigen-specific T-cell responses and prevents colitis", Nature, Oct. 16, 1997, pp. 737-742, 389.
Groux et al., Type I T-regulatory cells: their role in the control of immune responses. Transplantation. May 15, 2003;75(9 Suppl):8S-12S.
Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall, J.A., et al. (2008). Commensal DNA limits regulatory T cell conversion and is a natural adjuvant of intestinal immune responses. Immunity 29, 637-649.
Hamelmann et al., Noninvasive measurement of airway responsiveness in allergic mice using barometric plethysmography. Am J Respir Crit Care Med. Sep. 1997;156(3 Pt 1):766-75.
Hampe, J., et al. (2001 ). Association between insertion mutation in NOD2 gene and Crohn's disease in German and British populations. Lancet 357. 1925-1928.
Hampe, J., et al. (2007). A genome-wide association scan of nonsynonymous SNPs identifies a susceptibility variant for Crohn disease in Atg 16L 1. Nat Genet 39, 207-211.
Haregewoin et al., Human gamma delta+ T cells respond to mycobacterial heat-shock protein. Nature. Jul. 27, 1989;340(6231):309-12.
Harrington L. et al., "Interleukin 17-producing CD4+ effector T cells develop via a lineage distinct from the T helper type 1 and 2 lineages" *Nature Immunology*, Nov. 2005, vol. 6, No. 11, pp. 1123-1132, 10 pages.
Harth et al. Treatment of *Mycobacterium tuberculosis* with antisense oligonucleotides to glutamine synthetase mRNA inhibits glutamine synthetase activity, formation of poly-L glutamate/glutamine cell wall structure, and bacterial replication. Proc Natl. Acad. Sci. 97: 418-423, 2000.
He, B., et al. (2007). Intestinal bacteria trigger T cell-independent immunoglobulin A(2) class switching by inducing epithelial-cell secretion of the cytokine APRIL. Immunity 26, 812-826.
Hertl et al., T cell control in autoimmune bullous skin disorders. J Clin Investi. May 2006; 116( 5): 1159-66. Review.

(56) References Cited

OTHER PUBLICATIONS

Hewison M, et al. (2003) Differential regulation of vitamin D receptor and its ligand in human monocyte-derived dendritic cells. J Immunol 170: 5382-5390.
Hirata et al., Cytokine synthesis of human monocytes stimulated by triple or single helical conformer of an antitumour (1->3)-beta-D-glucan preparation, sonifilan. Zentralbl Bakteriol. Nov. 1998;288(3):403-13.
Hodge et al., *Allium sativum* (garlic) suppresses leukocyte inflammatory cytokine production in vitro: potential therapeutic use in the treatment of inflammatory bowel disease. Cytometry. Aug. 1, 2002;48(4):209-15.
Hofstetter et al., Th17 Cells in MS and Experimental Autoimmune Encephalomyelitis. Int MS J. Apr. 2009;16(1):12-8.
Hooper, L.V. (2009). Do symbiotic bacteria subvert host immunity? Nat Rev Microbiol 7, 367-374.
Hooper, L.V. et al. (2001) Commensal host-bacterial relationships in the gut. Science 292, 1115-1118.
Hori, S. et al. "Control of regulatory T cell development by the transcription factor Foxp3" Science vol. 299, No. 5609 pp. 1057-1061 (2003).
Horstman et al., "Enterotoxigenic *Escherichia coli* secretes active heat-labile enterotoxin via outer membrane vesicles", J Bio Chem., Apr. 28, 2000, pp. 12489-12496, 275.
Hu et al., "Inflammation-induced tumorigenesis in the colon is regulated by caspase-1 and NLRC4," Proc. Natl. Acad. Sci., vol. 107, 21635-21640 (2010).
Hue et al., Interleukin-23 drives innate and T cell-mediated intestinal inflammation:, J Exp Med., Oct. 9, 2006, pp. 2473-2483, 203 (11).
Huibregtse et al.., Immunopathogenesis of IBD: insufficient suppressor function in the gut? Gut. Apr. 2007;56(4):584-92. Epub Oct. 17, 2006
Hutloff et al., ICOS is an inducible T-cell co-stimulator structurally and functionally related to CD28. Nature. Jan. 21, 1999;397(6716):263-6.
International Preliminary Report on Patentability for Application No. PCT/US2008/082928, dated May 11, 2010, 6 pages.
International Preliminary Report on Patentability for Application No. PCT/US2010/032300, dated Oct. 25, 2011,6 pages.
International Preliminary Report on Patentability for Application No. PCT/US2012/023050, dated Jul. 30, 2013, 5 pages.
International Preliminary Report on Patentability for Application No. PCT/US2014/037392 dated Nov. 10, 2015.8 pages.
International Preliminary Report on Patentability for International Application No. PCT/US2016/037044 filed Jun. 10, 2016 on behalf of California Institute of Technology, dated Dec. 12, 2017. 9 pages (English Only).
International Search Report and Written Opinion for Application No. PCT/US2011/037476, dated Aug. 26, 2011, 9 pages.
Isaksson et al., Conditional DC depletion does not affect priming of encephalitogenicTh cells in EAE. Eur J Immunol. Oct. 2012;42(10):2555-63. doi: 10.1002/eji.201142239. Epub Aug. 8, 2012.
Ishikawa, H. et al., "Effect of intestinal microbiota on the induction of regulatory CD25 CD4+ T+ cells" Clin Exp Immunol 153, 127-135 (2008).
Itokazu et al., Abscess formation as a complication caused by postoperative osteomyelitis of the femur. Arch Orthop Trauma Surg. 1998;118(1-2):99-102. Review.
Itzkowitz & Harpaz, "Diagnosis and Management of Dysplasia in Patients With Inflammatory Bowel Diseases," Gastroenterology, vol. 126, 1634-1648 (2004).
Ivanov et al., "Induction of intestinal Th17 cells by segmented filamentous bacteria", Cell, Oct. 15, 2009, pp. 485-498, vol. 139, Issue 3, Elsevier Inc., Amsterdam, Netherlands.
Ivanov et al., "Specific microbiota direct the differentiation of IL-17-producing T-helper cells in the mucosa of the small intestine", Cell Host Microbe, Oct. 16, 2008, pp. 337-349, vol. 4, Issue 4.
Ivanov et al., "Transcriptional regulation of Th17 cell differentiation", Semin Immunol, Dec. 2007, pp. 409-417, vol. 19, Issue 6.
Ivanov, 11. Et al. "The Orphan Nuclear Receptor RORγt Directs the Differentiation Program of Proinflammatory IL-17+ T Helper Cells" Cell 126; 1121-1133 (2006).
Izcue et al., "Regulatory T cells suppress systemic and mucosal immune activation to control intestinal inflammation", Immunol Rev., Aug. 2006, pp. 256-271, vol. 212, Issue 1.
Izcue, A., et al. (2009). Regulatory lymphocytes and intestinal inflammation. Annu Rev Immunol 27, 313-338.
Japanese Decision of Rejection dated Oct. 29, 2013 for Japanese application 2010-533311 filed on Apr. 23, 2010 in the name of California Institute of Technology.
Japanese Notice for Reasons for Rejection dated Mar. 24, 2015 for Japanese application 2014-038746 filed on Nov. 9, 2008 in the name of California Institute of Technology.
Japanese Notification of Reasons for Refusal dated Feb. 12, 2014 for Japanese application 2012-507451 filed on Apr. 23, 2010 in the name of California Institute of Technology.
Japanese Official Decision of Refusal dated Feb. 10, 2015 for Japanese application 2012-507451 filed on Apr. 23, 2010 in the name of California Institute of Technology.
Jawad et al., "Inflammatory Bowel Disease and Colon Cancer," Recent Results Cancer Rec., vol. 185, 99-115 (2011).
Jeffery LE, et al. (2009) 1,25-Dihydroxyvitamin D3 and IL-2 combine to inhibit T cell production of inflammatory cytokines and promote development of regulatory T cells expressing CTLA-4 and FoxP3. J Immunol 183: 5458-5467.
Jennings et al., Immunochemistry of groups A, B, and C meningococcal polysaccharide-tetanus toxoid conjugates. J Immunol. Sep. 1981;127(3): 1011-8.
Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwul 17. Epub Oct. 27, 2014.
Jonuleit et al., Identification and functional characterization of human CD4(+)CD25(+) T cells with regulatory properties isolated from peripheral blood. J Exp Med. Jun. 4, 2001 ;193(11):1285-94.
Jonuleit et al., The regulatory T cell family: distinct subsets and their interrelations. J Immunol. Dec. 15, 2003;171(12):6323-7.
Joshi S, et al. (2011) 1,25-dihydroxyvitamin 0(3) ameliorates Th17 autoimmunity via transcriptional modulation of interleukin-17A. Molecular and cellular biology 31: 3653-3669.
Jotwani et al., Pathogenicity of Bacteroides fragilis group in rat intra-abdominal abscesses. Microbial Immunol. 1992;36(10):1041-9.
Jyonouchi, "Non-IgE Mediated Food Allergy", Inflammation & Allergy-Drug Targets, Sep. 2008, pp. 173-180. vol. 7, No. 3.
Kakalacheva K, et al. (2011) Environmental triggers of multiple sclerosis. FEBS letters 585: 3724-3729.
Kakalacheva K, et al. (2011) Viral triggers of multiple sclerosis. Biochimica et biophysica acta 1812: 132-140.
Kalka-Moll et al., "Effect of Molecular Size on the Ability of Zwitterionic Polysaccharides to Stimulate Cellular Immunity," J. Immunol., vol. 164, 719-24 (2000).
Kalka-Moll et al., "Zwitterionic Polysaccharides stimulate T cells by MHC class II-Dependent Interactions", The Journal of Immunology, Dec. 1, 2002, p. 6149-6153, vol. 169, Issue 11.
Kalka-Moll et al., Bacteroides Fragilis NCTC 9343 Capsular Polysaccharide PS A and the Effect of Chain Length of T cell Proliferation. Abstracts of the 98th Gen Mtg of the American Soc for Microbial. 1998;98:123. Abstract B-405.
Kasper et al., Capsular polysaccharides and lipopolysaccharides from two Bacteroides fragilis reference strains: chemical and immunochemical characterization. J Bacterial. Feb. 1983;153(2):991-7.

(56) References Cited

OTHER PUBLICATIONS

Kasper et al., Protective efficacy of immunization with capsular antigen against experimental infection with Bacteroides fragilis. J Infect Dis. Nov. 1979;140(5):724-3 I.

Kasper et al., Surface antigens as virulence factors in infection with Bacteroides fragilis. Rev Infect Dis. Mar.-Apr. 1979;1(2):278-90.

Kasper et al., The polysaccharide capsule of *Bacteroides fragilis* subspecies *fragilis*: immunochemical and morphologic definition. J Infect Dis. Jan. 1976;133(1):79-87.

Kato et al., Interleukin 10 reduces mortality from severe peritonitis in mice. Antimicrob Agents Chemother. Jun. 1995;39(6):1336-40.

Kayama H. et al., "Regulation of intestinal homeostasis by innate and adaptive immunity" *International Immunology*, vol. 24, No. 11, pp. 673-680,Sep. 2012, 8 pages.

Kennedy et al., Prevention of experimental postoperative peritoneal adhesions by N,0-carboxymethyl chitosan. Surgery. Nov. 1996;120(5):866-70.

Kernodle et al. Expression of an antisense hla fragment in *Staphylococcus aureus* reduces alpha-toxin production in vitro and attenuates lethal activity in a murine model. Infection and Immunity 179-184. 1997.

Kesty et al., "Incorporation of heterologous outer membrane and periplasmic proteins into *Escherichia coli* outer membrane vesicles", J Bio Chem., Jan. 16, 2004, pp. 2069-2076, 279.

Kidd, "Th1/Th2 Balance: The hypothesis, its limitations, and implications for health and disease", Alternative Medicine Review, 2003, pp. 223-246, vol. 8, No. 3, Thorne Research, Inc., Dover, ID.

Kim, J.M., et al. (2007). Regulatory T cells prevent catastrophic autoimmunity throughout the lifespan of mice. Nat Immunol 6, 191-197.

Kinoshita et al., Retinoic acid reduces autoimmune renal injury and increases survival in NZB/W FI mice. J Immunol. Jun. 1, 2003;170(11):5793-8.

Kirjavainen et al. "Healthy gut microflora and allergy: factors influencing development of the microbiota" Ann Med., 1999, pp. 288-292, vol. 31, Issue 4.

Knetsch et al., Polymers with tunable toxicity: a reference scale for cytotoxicity testing of biomaterial surfaces. J Biomed Mater Res A. Sep. 15, 2007;82(4):947-57.

Knirel et al., Somatic antigens of Pseudomonas aeruginosa. The structure of O-specific polysaccharide chains of lipopolysaccharides of P. aeruginosa 03 (Lanyi), 025 (Wokatsch) and Fisher immunotypes 3 and 7. Eur J Biochem. Sep. 15, 1987;167(3):549-61.

Knirel et al., The structure of O-specific polysaccharides and serological classification of Pseudomonas aeruginosa (a review). Acta Microbial Hung. 1988;35(1):3-24. Review.

Koch, M.A., et al. (2009). The transcription factor T-bet controls regulatory T cell homeostasis and function during type 1 inflammation. Nat Immunol 10, 595-602.

Kong, J., et al. Novel role of the vitamin D receptor in maintaining the integrity of the intestinal mucosal barrier. Am J Physiol Gastrointest Liver Physiol, 2008. 294(1): p. G208-16.

Kormelink et al., "Atopic and non-atopic allergic disorders: current insights into the possible involvement of free Immunoglobulin light chains", Clinical and Experimental Allergy, Jan. 2009, pp. 33-42, vol. 39, Issue 1.

Krause et al., An Inhibitor of Cell Proliferation Associated with Adhesion Formation Is Suppressed by N,0-Carboxymethyl Chitosan. J Investi Surg. 1988;11:105-113.

Krutzik SR, et al. (2008) "IL-15 links TLR2/1-induced macrophage differentiation to the vitamin D-dependent antimicrobial pathway". J Immunol 181: 7115-7120.

Kuehn, M.J. et al. "Bacterial outer membrane vesicles and the host-pathogen interaction" Genes and Development vol. 19, No. 22 pp. 2645-2655 (2005).

Kuhn et al., "Interleukin-10 deficient mice develop chronic enterocolitis", Cell, Oct. 22, 1993, pp. 263-274, vol. 75, Issue 2.

Kulicke et al., Correlation between immunological activity, molar mass, and molecular structure of different (1->3)-beta-D-glucans. Carbohydr Res. Jan. 2, 1997;297(2):135-43.

Kullberg et al., "IL-23 plays a key role in Helicobacter hepaticus-induced T cell-dependent colitis", J Exp Med., Oct. 9, 2006, pp. 2485-2494, 203 (11): 2485.

Kullberg et al., "Bacteria-triggered CD4(+) T regulatory cells suppress Helicobacter hepaticus-induced colitis", J Exp Med., Aug. 19, 2002, pp. 505-515, 196 (4): 505.

Kullberg et al., "Helicobacter hepaticus Triggers Colitis in Specific-Pathogen-Free Interleukin-10 (IL-10)-Deficient Mice through an IL-12- and Gamma Interferon-Dependent Mechanism", Infection and Immunity Nov. 1998, pp. 5157-5166, vol. 66 No. 11.

Kullberg et al., "Induction of colitis by a CD4+ T cell clone specific for a bacterial epitope", Proc Natl Acad Sci USA, Dec. 23, 2003, pp. 15830-15835, vol. 100 No. 26.

Kuper et al., "Infections as a major preventable cause of human cancer," J. Intern. Med., vol. 248, 171-183 (2000).

Kurup et al., Antibody response to low-molecular-weight antigens of Aspergillus fumigatus in allergic bronchopulmonary aspergillosis. J Clin Microbial. Jun. 1989;27(6):1312-6.

Lagishetty, V. et al. "Vitamin D deficiency in mice impairs colonic antibacterial activity and predisposes to colitis." Endocrinology.; Jun. 2010; vol. 151(6) pp. 2423-2432.

Lee et al., "Bacterial colonization factors control specificity and stability of the gut microbiota," Nature, vol. 501, 426-429 (2013).

Lee et al., "Plasma Interleukin-1 beta, -6, -8 and Tumor Necrosis Factor-alpha as Highly Informative Markers of Pelvic Inflammatory Disease," Clinical Chemistry and Laboratory Medicine, Jul. 1, 2008, pp. 997-1003, vol. 46, No. 7., Watlerde Gruyter GmbH, Berlin, Germany.

Lee et al., Effects of IN Vitro and In Vivo and Growth Conditions on Expression of Type 8 Capsular Polysaccharide by *Staphylococcus aureus*, Infection and Immunity, 61: 1853-1858, 1993.

Lee YK, et al. (2010) Has the microbiota played a critical role in the evolution of the adaptive immune system? Science 330: 1768-1773.

Lee YK, et al. (2011) Proinflammatory T-cell responses to gut microbiota promote experimental autoimmune encephalomyelitis. Proc Natl Acad Sci U S A 108 Suppl 1: 4615-4622.

Ley et al., "Ecological and evolutionary forces shaping microbial diversity in the human intestine", Cell, Feb. 24, 2006, pp. 837-848,vol. 124, Issue 4.

Ley et al., Evolution of mammals and theirgut microbes. Science. Jun. 20, 2008;320(5883): 1647-51. doi: 10.1 126/science.1155725. Epub May 22, 2008.

Lin et al., "Regulatory T cell development in the absence of functional Foxp3", Nat. Immunol., Mar. 2007, pp. 359-368, vol. 8, Issue 4, Nature Publishing, London, United Kingdom.

Lindberg et al., Virulence factors in infections with bacteroides fragilis: isolation and characterization of capsular polysaccharide and lipopolysaccharide. Scand J Infect Dis Suppl. 1982;35:45-52.

Liu et al., "Regulation of surface architecture by symbiotic bacteria mediates host colonization", Proc Natl Acad Sci USA, Mar. 11, 2008, pp. 3951-3956, vol. 105 No. 10.

Liu et al., "Toll-like receptor 2 signaling modulates the functions of CD4+ CD25+ regulatory T cells", Proc. Natl. Acad. Sci. USA, May 2, 2006, pp. 7048-7053, vol. 103 No. 18.

Liu P.T., et al., "Toll-like Receptor Triggering of a Vitamin D-mediated Human Antimicrobial Response," Science, Mar. 2006, vol. 311 (5768), 4 pages.

Liu, N. et al. "Altered endocrine and autocrine metabolism of vitamin D in a mouse model of gastrointestinal inflammation." Endocrinology, 2008; 149(10): pp. 4799-4808.

Liu et al., "Glucuronoxylomannan promotes the generation of antigen-specific T regulatory cell that suppresses the antigen-specific Th2 response upon activation,", J. Cell. Mol. Med. vol. 13: 1765-1774.Online Nov. 2008. 10 Pages.

Lysnyansky et al. Juxtaposition of an active promoter to via genes via site-specific DNA inversions generates antigenic variation in Mycoplasma bovis. (2001) J Bacteriol 183:5698-5708.

Macpherson et al., IgA responses in the intestinal mucosa against pathogenic and nonpathogenic microorganisms. Microbes Infect. Oct. 2001;3(12):1021-35.

Macpherson et al., Interactions between commensal intestinal bacteria and the immune system. Nat Rev Immunol. Jun. 2004;4(6):478-85.

(56) References Cited

OTHER PUBLICATIONS

Macpherson et al., Mucosal antibodies in inflammatory bowel disease are directed against intestinal bacteria. Gut. Mar. 1996;38(3):365-75.
Macpherson, A.J. et al. (2004). Induction of protective IgA by intestinal dendritic cells carrying commensal bacteria. Science 303, 1662-1665.
Maier, B.R., et al. (1972). Experimental Shigella infections in laboratory animals. I. Antagonism by human normal flora components in gnotobiotic mice. Infect Immun 6, 168-173.
Makela et al., IL-10 is necessary for the expression of airway hyperresponsiveness but not pulmonary inflammation after allergic sensitization. Proc Natl Acad Sci USA. May 23, 2000;97(11):6007-12.
Maloy et al., "CD4+CD25+ T(R) cells suppress innate immune pathology through cytokine-dependent mechanisms", J Exp Med., Jan. 6, 2003, pp. 111-119, 197.
Mamessier et al., "Cytokines in atopic diseases: revisiting the Th2 dogma" Eur J Dermatol. Mar.-Apr. 2006;16(2):pp. 103-113.
Mantovani et al., "Cancer-related inflammation," Nature, vol. 454, 436-444 (2008).
Maynard CL, et al. (2009) Contrasting roles for all-trans retinoic acid in TGF-beta-mediated induction of Foxp3 and IL10 genes in developing regulatory T cells. The Journal of experimental medicine 206: 343-357.
Maynard et al., "Diversity in the contribution of interleukin-10 to T-cell-mediated immune regulation", Immunol. Rev., Dec. 2008 , pp. 219-233, vol. 226, Issue 1.
Maynard, C.L., et al. (2007). Regulatory T cells expressing interleukin 10 develop from Foxp3+ and Foxp3-precursor cells in the absence of interleukin 10. Nat Immunol 8, 931941.
Mayne CG, et al. (2011) "1,25-Dihydroxyvitamin D3 acts directly on the T lymphocyte vitamin D receptor to inhibit experimental autoimmune encephalomyelitis". European journal of immunology 41: 822-832.
Mazmanian et al., "A microbial symbiosis factor prevents intestinal inflammatory disease," Nature, vol. 453, 620-625 (2008).
Mazmanian et al., "Bacterial Immunomodulatory Regulation during Mammalian Health and Disease", Harvard Medical School, Brigham and Women's Hospital. (Oct. 11, 2005).
Mazmanian et al., "The Evolution of Symbiosis: From Bacteria to Commensal to Beneficial Microbe", Nature, May 29, 2008, pp. 620-625, 453.
Mazmanian et al., "The love-hate relationship between bacterial polysaccharides and the host immune system", Nature Reviews Immunology, Nov. 2006, pp. 849-858, vol. 6, No. 11.
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01.mpg.0000313824.70971.a7.
Mazmanian, S.K. Host-bacterial symbiosis prevents intestinal inflammatory disease. California Institute of Technology. Amgen (Jul. 2008).
McClain et al. Inversion-Independent phase variation of type 1 fimbriae in *Escherichia coli*. (1993) J Bacteriol 175(14):4335-44.
McMurchy A.N., et al. (2012) Suppression assays with human T regulatory cells: a technical guide. European journal of immunology 42: 27-34.
Meisel-Mikolajczyk et al., Human T cell adhesion to endothelium stimulated by membrane components extracted from strains of *Bacteroides vulgatus* (member of *B. fragilis* group). Arch Immunol Ther Exp (Warsz). 1993;41 (2):129-31.
Meltzer, et al., "Pneumococcal Polysaccharides Interact with Human Dendritic Cell,". Infect. Immun. vol. 74: 1890-1895. Mar. 2006. 7 Pages.
Merriam-Webster. Hypothesize. 2013. Web http://www.merriam-webster.com/dictionary/hypothesize.
Merriam-Webster. Suggest. 2013. Web<http://www.merriam-websler.com/diclionary/suggesl>.

Mertens, J., et al., *Streptococcus pneumoniae* Serotype 1 Capsular Polysaccharide Induces CD8+CD28-Regulatory T Lymphocytes by TCR Crosslinking, PLOS Pathogens, (Sep. 2009) vol. 5, Issue 9, e1000596, p. 1-15.
Miller et al., Severe asthma and the omalizumab option. Clinical and Molecular Allergy 2008, 6:4.
Min, B., et al. (2007). Gut flora antigens are not important in the maintenance of regulatory T cell heterogeneity and homeostasis. Eur. J. Immunol. 37; pp. 1816-1923.
Mojtabavi et al., Long-lived Th2 memory in experimental allergic asthma. J Immunol. Nov. 1, 2002; 169(9):4 788-96.
Montz et al., Interleukin 10: ability to minimize postoperative intraperitoneal adhesion formation in a murine model. Fertil Steril. Jun. 1994;61(6):1136-40.
Moore, The List Goes On, New Additions to the Autoimmune Disease Raster. http://autoimmunedisease.suiteIOI.com/blog.cfm/the list goes on. pp. 1-3. Aug. 7, 2007.
Moorman et al., National Surveillance of Asthma: United States, 2001-2010. National Center for Health Statistics. Vital Health Stat. 2012;3(35) 67 pages.
Mor et al., Identification of aldolase as a target antigen in Alzheimer's disease. J Immunol. Sep. 1, 2005; 175(5):3439-45.
Mora et al., Generation of gut-homing IgA-secreting B cells by intestinal dendritic cells. Science. Nov. 17, 2006;314(5802):1157-60.
Mora et al., Selective imprinting of gut-homing T cells by Peyer's patch dendritic cells. Nature. Jul. 3, 2003;424(6944):88-93.
Morales-Tirado V, et al. (2011) 1 alpha,25-dihydroxyvitamin D3 (vitamin D3) catalyzes suppressive activity on human natural regulatory T cells, uniquely modulates cell cycle progression, and augments FOXP3. Clinical immunology 138: 212-221.
Motta, A.C. et al. (2006) T cells in asthma: Lessons from mouse models. Drug Discovery Today: Disease Models, vol. 3, No. 3; pp. 199-204.
Mulholland et al., Strategies for the control of pneumococcal diseases. Vaccine. Jul. 30, 1999;17 Suppl I:S79-84. Review.
Nagaraj S. et al., "Reciprocal Relationship between Myeloid-Derived Suppressor Cells and T Cells" *Journal of Immunology*, Dec. 2013, pp. 17-23 8 pages.
Nakayama-Imaohji, H. et al. "Identification of the site-specific DNA invertase responsible forthe phase variation of SusC/SusD family outer membrane proteins in Bacteroides fragilis" J. Bacterial.; 2009; vol. 191; No. 19; pp. 6003-6011.
Natori et al., Agelasphins, novel antitumor and immunostimulatory cerebrosides from the marine sponge *Agelas mauritianus*. Tetrahedron. 1994;50(9):2771-2784.
NCBI Sequence View "Toxin" [*Salmonella typhimurium* LT2], Retrieved Aug. 16, 2007 from http://www.ncbi.nim.nih.oov/entrez/viewer.fcoi?db=protein&id= 17233414, pp. 1-2.
Neurath et al., "TNBS-colilis", Int Rev Immunol., 2000, pp. 51-62, 19(1).
Nielsen et al., Applications of peptide nucleic acids. Curr Opin Biotechnol. Feb. 1999;10(1):71-5. Review.
Niess et al., "Commensal gut flora drives the expansion of proinflammatory CD4 T cells in the colonic lamina propria under normal and inflammatory conditions", J Immunol., Jan. 1, 2008, pp. 559-568, vol. 180, Issue 1.
No Author Listed, Acute Respiratory Disease Syndrome: What is acute respiratory disease syndrome? American Lung Association. 3 pages. http://www.lungusa.org/site/apps/nlnet/content3.aspz?c=dvLUK900E&b=2058817&content. Sep. 24, 2008.
No Author Listed, Excerpts from Immunobiology, in ed.. "Chapter 9. pp. 335-361; Chapter 1. pp. 2-9; Chapter 15. pp. 622-631" 2008.
No Author Listed, Lupus study. Meet A Lupus Researcher, www.lupusstudy.org/updates.php. Nov. 2005; 1-2.
No Author Listed, Polyethylene Glycols (PEGs). Accessed Mar. 7, 2005. 1 page. http://www.mindfully.org/Plastic/Polymers/Polyethylene-Glycols-PEGs.htm.
No Author Listed, The Merck Index. Eleventh Edition 1989:734-735.
No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.

(56) References Cited

OTHER PUBLICATIONS

Non-Final Office Action for U.S. Appl. No. 12/267,602, filed Nov. 9, 2008 on behalf of Sarkis K. Mazmanian et al, dated Jul. 15, 2011. 12 pages.
Non-Final Office Action for U.S. Appl. No. 12/766,787, filed Apr. 23, 2010 on behalf of June L. Round et al, dated Jan. 20, 2015. 18 pages.
Non-Final Office Action for U.S. Appl. No. 12/766,787, filed Apr. 23, 2010 on behalf of June L. Round et al, dated May 8, 2012. 9 pages.
Non-Final Office Action for U.S. Appl. No. 12/766,787, filed Apr. 23, 2010 on behalf of June L. Round et al, dated Sep. 30, 2013. 19 pages.
Non-Final Office Action for U.S. Appl. No. 12/831,131, filed Jul. 6, 2010 on behalf of June L. Round et al, dated Aug. 26, 2014. 20 pages.
Non-Final Office Action for U.S. Appl. No. 12/831,131, filed Jul. 6, 2010 on behalf of June L. Round et al, dated Nov. 15, 2012. 22 pages.
Non-Final Office Action for U.S. Appl. No. 13/082,183, filed Apr. 7, 2011 on behalf of Yue Shen et al, dated Aug. 13, 2013. 7 pages.
Non-Final Office Action for U.S. Appl. No. 13/082,183, filed Apr. 7, 2011 on behalf of Yue Shen et al, dated Jan. 20, 2015. 7 pages.
Non-Final Office Action for U.S. Appl. No. 13/112,725, filed May 20, 2011 on behalf of June L. Round, dated Mar. 18, 2016. 11 pages.
Non-Final Office Action for U.S. Appl. No. 13/112,725, filed May 20, 2011 on behalf of June L. Round, dated May 30, 2013. 7 pages.
Non-Final Office Action for U.S. Appl. No. 13/112,725, filed May 20, 2011 on behalf of June L. Round, dated May 8, 2014. 12 pages.
Non-Final Office Action for U.S. Appl. No. 13/360,702, filed Jan. 28, 2012 on behalf of Sarkis K. Mazmanian et al, dated Mar. 11, 2015. 13 pages.
Non-Final Office Action for U.S. Appl. No. 13/360,702, filed Jan. 28, 2012 on behalf of Sarkis K. Mazmanian et al, dated Mar. 18, 2013. 13 pages.
Non-Final Office Action for U.S. Appl. No. 13/464,876, filed May 4, 2012 on behalf of Sarkis K. Mazmanian et al, dated Jul. 9, 2013. 16 pages.
Non-Final Office Action for U.S. Appl. No. 13/573,695 filed Oct. 3, 2012 on behalf of Sarkis K. Mazmanian et al, dated Aug. 28, 2013. 11 pages.
Non-Final Office Action for U.S. Appl. No. 14/015,769, filed Aug. 30, 2013 on behalf of Sarkis K. Mazmanian et al, dated Dec. 31, 2014. 7 pages.
Non-Final Office Action dated Aug. 9, 2017 in U.S. Appl. No. 14/264,607.
Non-Final Office Action dated Jan. 18, 2019 in U.S. Appl. No. 14/264,607.
Non-Final Office Action dated Mar. 16, 2017 in U.S. Appl. No. 14/631,760.
Non-Final Office Action dated Mar. 22, 2017 in U.S. Appl. No. 14/660,827.
Non-Final Office Action dated Dec. 27, 2018 in U.S. Appl. No. 14/660,827.
Non-Final Office Action dated May 11, 2018 in U.S. Appl. No. 14/803,598.
Non-Final Office Action for U.S. Appl. No. 15/011,151, filed Jan. 29, 2016 on behalf of California Institute of Technology dated Aug. 30, 2017 20 pages.
Non-Final Office Action dated Mar. 5, 2019 in U.S. Appl. No. 15/706,604.
Non-Final Office Action dated Nov. 17, 2019 in U.S. Appl. No. 16/514,796.
Non-Final Office Action dated Jun. 8, 2020 in U.S. Appl. No. 16/386,522.
Non-Final Office Action dated Aug. 7, 2020 in U.S. Appl. No. 16/151,793.
Non-Final Office Action dated Sep. 1, 2020 in U.S. Appl. No. 16/562,358.
Norman; "Thyroiditis-Inflammation of the thyroid gland"; Endocrineweb 2009; www.endocrineweb.com/throiditis.html, 1-4. Downloaded Jul. 28, 2009.
Notice of Allowance for U.S. Appl. No. 13/573,695, filed Oct. 3, 2012 on behalf of Sarkis K. Mazmanian et al, dated Feb. 13, 2015. 9 pages.
Notice of Allowance for U.S. Appl. No. 13/573,695, dated May 15, 2015, 2 pages.
Notice of Allowance dated May 1, 2020 in U.S. Appl. No. 16/514,796.
Notice of Allowance dated Jul. 7, 2018 in European Patent Application No. 11766746.9.
Notice of Allowance dated Sep. 16, 2016 in Japanese Patent Application No. 2013-503958.
Notice of Allowance dated Jan. 9, 2018 in Japanese Patent Application No. 2016-126806.
Notice of Allowance dated Feb. 10, 2020 in Japanese Patent Application No. 2018-020819.
Notice of Reasons for Refusal dated Apr. 25, 2017 in Japanese Patent Application No. 2016-126806.
Notice of Reasons for Refusal dated Dec. 14, 2018 in Japanese Patent Application No. 2018-020819.
Notice of Reasons for Refusal dated Oct. 10, 2019 in Japanese Patent Application No. 2018-020819.
Notice of Reasons for Refusal dated Mar. 23, 2015 in Japanese Patent Application No. 2013-503958.
Notice of Reasons for Refusal dated Dec. 28, 2017 in Japanese Patent Application No. 2016-513092.
Notice of Reasons for Refusal dated Mar. 18, 2020 in Japanese Patent Application No. 2019-061261.
Notice Of Reasons For Rejection for JP 2010-533311 dated May 14, 2013 in the name of California Institute of Technology. (English Translation).
Notification of Reason for Refusal for Japanese Patent Application No. 2013-511406, dated Apr. 12, 2016. 7 pages (Japanese original + English translation).
Notification of Reasons for Refusal for Japanese Patent Application No. 2013-511406, dated May 12, 2015. 6 pages (Japanese original+ English translation).
Noverr MC, et al. (2004) Does the microbiota regulate immune responses outside the gut? Trends Microbiol 12: 562-568.
Nylander A, et al. (2012) "Multiple sclerosis". The Journal of Clinical Investigation; vol. 122; DO. 1180-1188.
Ochoa-Reparaz J, et al. (2009) Role of gut commensal microflora in the development of experimental autoimmune encephalomyelitis. J Immunol 183: 6041-6050.
Ochoa-Reparaz J, et al. (2010) A polysaccharide from the human commensal Bacteroides fragilis protects against CNS demyelinating disease. Mucosal Immunol 3: 487-495.
Ochoa-Reparaz J, et al. (2010) Central nervous system demyelinating disease protection by the human commensal Bacteroides fragilis depends on polysaccharide A expression. J Immunol 185: 4101-4108.
Ochoa-Reparaz, J. et al. "The role of subcellular fractions of commensal Bacteroides fragilis in the control of experimental autoimmune encephalomyelitis" Multiple Sclerosis; Sep. 2009; vol. 15; (Abstract Only).
O'Connor et al., Translational mini-review series on Th17 cells: CD4 T helper cells: functional plasticity and differential sensitivity to regulatory T cell-mediated regulation. Clin Exp Immunol. Feb. 2010;159(2):137-47. doi: 10.1111/j.1365-2249.2009.04040.x. Epub Nov. 11, 2009.
Oda et al., A comprehensive map of the toll-like receptor signaling network. Mol Syst Biol. 2006;2:2006.0015. Epub Apr. 18, 2006.
Office Action for Japanese patent application No. JP2015-116494, dated Jul. 12, 2016. 8 pages (Japanese original + English translation).
O'Garra et al., "IL-10-producing and naturally occurring CD4+ Tregs: limiting collateral damage", J Clin Invest, Nov. 15, 2004, pp. 1372-1378, 114(10), National Center for Biotechnology Information, Bethesda MD.
Oh et al., CD4 T-helper cells engineered to produce IL-10 prevent allergen-induced airway hyperreactivity and inflammation. J Allergy Clin Immunol. Sep. 2002;110(3):460-8.

(56) References Cited

OTHER PUBLICATIONS

O'Hara et al., "The gut flora as a forgotten organ", EMBO, Jul. 1, 2006, pp. 688-693,vol. 7, Issue 7, EMBO, Heidelberg, Germany.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1->3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk, A. et al., Evidence for T Cell-dependent Immunity to Bacteroides fragilis in an Intraabdominal Abscess Model; J. Clin Investi. 69:9-16 (1982).
Ostman et al., "Impaired regulatory T cell function in germ-free mice", European Journal of Immunology, Sep. 2006 , pp. 233-246, vol. 36, Issue 9.
Ozenci et al., Multiple sclerosis: levels of interleukin-10-secreting blood mononuclear cells are low in untreated patients but augmented during interferon-beta-1 b treatment. Scand J Immunol. May 1999;49(5):554-61.
Palmer et al., "Development of the Human Infant Intestinal Microbiola", PLoS Biol., Jun. 26, 2007, pp. 1556-1573. vol. 5, Issue 7, e177, PLOS, San Francisco, CA.
Palmer MT, et al. (2011) Lineage-specific effects of 1,25-dihydroxyvitamin D(3) on the development of effector CD4 T cells. The Journal of biological chemistry 286: 997-1004.
Pamer, "Immune responses to commensal and environmental microbes", Nat Immunol., Oct. 19, 2007, pp. 1173-1178, 8.
Pantosti et al., Bacteroides fragilis strains express multiple capsular polysaccharides. J Clin Microbial. Jul. 1993;31(7):1850-5.
Paoletti et al., Effects of chain length on the immunogenicity in rabbits of group B *Streptococcus* type 111 oligosaccharide-tetanus toxoid conjugates. J Clin Investi. Jan. 1992;89(1):203-9.
Paoletti et al., Neonatal Mouse Protection against Infection with Multiple Group B *Streptococcal* (GBS) Serotypes by Maternal Immunization with a Tetravalent GBS Polysaccharide-Tetanus Toxoid Conjugate Vaccine, Infection and Immunity, 62:3236-3243, 1994.
Park et al., Interleukin-2 and soluble interleukin-2 receptor in bronchoalveolar lavage fluid from patients with bronchial asthma. Chest. Aug. 1994;106(2):400-6.
Patrick et al. "Mutational analysis of genes implicated in LPS and capsular polysaccharide biosynthesis in the opportunistic pathogen Bacteroides fragilis" Microbiology. Apr. 2009;155(Pt 4):1039-49.
Patrick et al., "A comparison of the haemagglutinating and enzymic activities of Bacteroides fragilis whole cells and outer membrane vesicles", Apr. 1996, pp. 191-202, vol. 20, Issue 4, Elsevier, Amsterdam, Netherlands.
Patrick et al., "Separation of capsulate and non-capsulate Bacteriodes fragilis on a discontinuous density gradient", J Med Microbial. , 1983, pp. 239-241, 16(2), The Pathological Society of Great Britain and Ireland, London, United Kingdom.
Pavliak et al., Structural elucidation of the capsular polysaccharide of Bacteroides fragilis strain 23745MI. Carbohydr Res. Oct. 2, 1995;275(2):333-41.
PCT Application No. PCT/US2011/031606 Search Report and Written Opinion dated Dec. 15, 2011.
PCT International Search Report and Written Opinion for International Patent Application No. PCT/US2012/023050, dated May 21, 2012. 7 pages.
PCT International Search Report and Written Opinion for PCT Application No. PCT/US2014/037392 filed May 8, 2014 on behalf of California Institute of Technology, dated Sep. 19, 2014. 28 pages.
PCT Search Report for PCT/US2008/082928 in the name of California Institute of Technology filed on Nov. 9, 2008.
PCT Written Opinion dated Jun. 30, 2009 for PCT/US2008/082928 filed on Nov. 9, 2008 in the name of California Institute of Technology.
PCT International Search Report for PCT/US2010/032300 filed Apr. 23, 2010 on behalf of California Institute of Technology et al, dated Jan. 31, 2011. 5 pages.
PCT Written Opinion for PCT/US2010/032300 filed Apr. 23, 2010 on behalf of California Institute of Technology et al, dated Jan. 31, 2011. 5 pages.
Pedersen LB, et al. (2007) 1,25-dihydroxyvitamin D3 reverses experimental autoimmune encephalomyelitis by inhibiting chemokine synthesis and monocyte trafficking. J Neurosci Res 85: 2480-2490.
Perumal et al., Protective effect of interleukin-2 on experimental intra-abdominal abscess development due to Bacteriodes Fragilis. Clinical Research. 1990;38(2):550A.
Pierrot-Deseilligny C, et al. Is hypovitaminosis Done of the environmental risk factors for multiple sclerosis? Brain; 2010; 133: 1869-1888.
Pillay J. et al., "Immune suppression by neutrophils and granulocytic myeloid-derived suppressor cells: similarities and differences" Cellular and Molecular Life Sciences, Feb. 2013, pp. 3813-3827 15 pages.
Poonawalla et al., "Urticaria—A Review", Am J Clin Dermalol., 2009, pp. 9-21, vol. 10, No. 1, Springer, Berlin, Germany.
Popivanova et al., "Blocking TNF-a in mice reduces colorectal carcinogenesis associated with chronic colitis," J. Clin. Invest., vol. 118, 560-570 (2008).
Popovic et al., Inhibition of autoimmune encephalomyelitis by a tetracycline. Ann Neural. Feb. 2002;51(2):215-23.
Power C, et al. (2010) The human microbiome in multiple sclerosis: pathogenic or protective constituents? The Canadian journal of neurological sciences Le journal canadien des sciences neurologiques 37 Suppl 2: S24-33.
Powrie et al., "Immunology. Regulating the regulators", Science, Feb. 14, 2003, pp. 1030-1031, 299(5609), AAAS, Washington, DC.
Poxton et al., Mucosa-associated bacterial flora of the human colon. J Med Microbial. Jan. 1997; 46(1):85-91.
Pragani & Seeberger, "Total Synthesis of the *Bacteroides fragilis* Zwitterionic Polysaccharide A 1 Repeating Unit," JACS 2011, 133, 102-107.
Prieto et al., A new ganglioside in human meconium detected by antiserum against the human milk sialyloligosaccharide, LS-tetrasaccharide b, Archives of Biochemistry and Biophysics, 241:281-289, 1985.
Rabe et al., Pharmacological treatment of asthma today. Eur Respir J Suppl. 2001; 34:34s-40s.
Raetz et al., Lipopolysaccharide endotoxins. Annu Rev Biochem. 2002;71 :635-700. Epub Nov. 9, 2001.
Raghuwanshi, A. et al. "Vitamin D and Multiple Sclerosis" Journal of Cellular Biochemistry; 2008; vol. 105; pp. 338-343.
Rakoff-Nahoum et al., "Recognition of commensal microflora by loll-like receptors is required for Intestinal homeostasis", Cell, Jul. 23, 2004, pp. 229-241, vol. 118, Issue 2.
Raman et al. Vitamin D and gastrointestinal diseases: inflammatory bowel disease and colorectal cancer in Ther Adv. Gastroenterology, Jan. 10, 2011 (Jan. 10, 2011) vol. 4, pp. 49-62.
Ranua et al., Serum IgA, IgG, and IgM concentrations in patients with epilepsy and matched controls: a cohort-based cross-sectional study. Epilepsy Behav. Mar. 2005;6(2):191-5.
Reid, R.R., et al., "Endotoxin shock in antibody-deficient mice: unraveling the role of natural antibody and complement in the clearance of lipopolysaccharide," *Journal of immunology*, 1997. 159(2): p. 970-5. Abstract Only.
Rescigno, M. et al., "Dendritic cells express tight junction proteins and penetrate gut epithelial monolayers to sample bacteria" Nat Immunol 2, 361 (2001).
Restriction Requirement for U.S. Appl. No. 12/766,787, filed Apr. 23, 2010 on behalf of June L. Round et al, dated Mar. 15, 2012. 9 pages.
Restriction Requirement for U.S. Appl. No. 13/082,183, filed Apr. 7, 2011 on behalf of Yue Shen et al, dated May 31, 2013. 7 pages.
Restriction Requirement for U.S. Appl. No. 13/112,725, filed May 20, 2011 on behalf of June L. Round, dated Mar. 18, 2013. 7 pages.

(56) References Cited

OTHER PUBLICATIONS

Restriction Requirement for U.S. Appl. No. 13/360,702, filed Jan. 28, 2012 on behalf of Sarkis K. Mazmanian et al, dated Feb. 1, 2013. 6 pages.
Restriction Requirement for U.S. Appl. No. 13/573,695 filed Oct. 3, 2012 on behalf of Sarkis K. Mazmanian et al, dated May 23, 2013. 9 pages.
Restriction Requirement for U.S. Appl. No. 14/755,327, filed Jun. 30, 2015 on behalf of Sarkis K. Mazmanian et al, dated Aug. 11, 2016. 8 pages.
Restriction Requirement issued by the USPTO for U.S. Appl. No. 12/267,602 dated Mar. 17, 2011.
Restriction Requirement issued in U.S. Appl. No. 13/464,876, filed May 4, 2012 in the name of Sarkis Mazmanian, dated Feb. 20, 2013.
Restriction Requirement dated Jul. 11, 2012 for U.S. Appl. No. 12/831,131, filed Jul. 6, 2010 in the name of June L. Round.
Restriction Requirement dated Aug. 18, 2014 in U.S. Appl. No. 14/015,769.
Restriction Requirement dated Jan. 26, 2015 in U.S. Appl. No. 14/274,607.
Restriction Requirement for U.S. Appl. No. 14/803,598, filed Jul. 20, 2015 on behalf of California Institute of Technology dated Feb. 14, 2018. 7 pages.
Restriction Requirement for U.S. Appl. No. 15/499,805, filed Apr. 27, 2017 on behalf of California Institute of Technology dated May 3, 2019 7 pages.
Restriction Requirement dated May 4, 2018 in U.S. Appl. No. 15/178,810.
Restriction Requirement dated Jan. 14, 2021 in U.S. Appl. No. 16/386,522.
Riesenfeld et al., Biosynthesis of heparin. Assay and properties of the microsomal N- acetyl-D glucosaminyl N-deacetylase. J Biol Chem. Feb. 10, 1980;255(3):922-8.
Rodgers et al., "Prescribing an antibiotic? Pair it with probiotics", The Journal of Family Practice, Mar. 2013, pp. 148-150, vol. 62, No. 3.
Roncarolo et al., Type IT regulatory cells. Immunol Rev. Aug. 2001;182:68-79. Review.
Round et al., "Inducible Foxp3+ regulatory T cell development by a commensal bacterium of the intestinal microbiota", PNAS, Jul. 6, 2010, pp. 12204-12209, vol. 107 No. 27.
Round et al., "The gut microbiota shapes intestinal immune responses during health and disease", Nat Rev Immunol., May 1, 2009, pp. 313-323, 9.
Round JL, et al. (2009) Coordination of tolerogenic immune responses by the commensal microbiota. J Autoimmun.
Round JL, et al. (2011) The Toll-like receptor 2 pathway establishes colonization by a commensal of the human microbiota. Science 332: 974-977.
Rubtsov et al., "Regulatory T cell-derived interleukin-10 limits inflammation at environmental interfaces", Immunity, Apr. 11, 2008, pp. 546-558, vol. 28, Issue 4.
Ruiz-Perez et al., "Modulation of surgical fibrosis by microbial zwitterionic polysaccharides", PNAS, Nov. 15, 2005, pp. 16753-16758, vol. 102, No. 46.
Runia TF, et al. (2012) Lower serum vitamin D levels are associated with a higher relapse risk in multiple sclerosis. Neurology 79: 261-266.
Rutgeerts et al., "Infliximab for induction and maintenance therapy for ulcerative colitis", N Engl J Med., Dec. 8, 2005, pp. 2462-2476, 353.
Rypens et al., Percutaneous drainage of abdominal abscesses in pediatric Crohn's disease. AJR Am J Roentgenol. Feb. 2007;188(2):579-85.
Sakaguchi S, et al. (2008) Regulatory T cells and immune tolerance. Cell 133: 775-787.
Sakaguchi, S. et al. (2006) Foxp3+ CD25+ CD4+ natural regulatory T cells in dominant self-tolerance and autoimmune disease. Immunol. Rev. 212, pp. 8-27.
Salyers et al., Conjugative transposons: an unusual and diverse set of integrated gene transfer elements. Microbial Rev. Dec. 1995;59(4):579-90. Review.
Sartor., "Mechanisms of disease: pathogenesis of Crohn's disease and ulcerative colitis", Nat Clin Pract Gastroenterol Hepatol., Jul. 1, 2006, pp. 390-407, 3.
Sawada et al., "Leukocytapheresis in Ulcerative Colitis: Results of a Multicenter Double-Blind Prospective Case-Control Study with Sham Apheresis as Placebo Treatment", American Journal of Gastroenterology, Jun. 1, 2005, pp. 1362-1369, vol. 100.
Scheiffele and Fuss. (2001) Induction of TNBS colitis in mice. Current Protocols in Immunology.15.19.1-15.19.14.
Scheinin et al., "Validation of theinterleukin-10 knockout mouse model of colitis: antitumour necrosis factor antibodies suppress the progression of colitis", Clin Exp Immunol., Jul. 2003, pp. 38-43, vol. 133, Issue 1.
Schembri MA et al. Orientation-dependent enhancement by H-NS of the activity of the type 1 fimbrial phase switch promoter in *Escherichia coli*. (1998) Mol Gen Genet 259:336-44.
Schlegel et al., A synthetic random basic copolymer with promiscuous binding to class 11 major histocompatibility complex molecules inhibits T-cell proliferative responses to major and minor histocompatibility antigens in vitro and confers the capacity to prevent murine graft-versus-host disease in vivo. Proc Natl Acad Sci USA. May 14, 1996;93(10):5061-6. Erratum in: Proc Natl Acad Sci USA Aug. 6, 1996;93(16):8796.
Schneider et al., De nova design of molecular architectures by evolutionary assembly of drug derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from *Trimeresurus wagleri* which blocks the nicotinic acetylcholine receptor. Biophys J. Jan. 1996;70(1):3-13.
Sellon et al. "Resident enteric bacteria are necessary for development of spontaneous colitis and immune system activation in interleukin-10-deficient mice", Infect Immun., Nov. 1998, pp. 5224-5231, vol. 66 No. 11.
"Sepsis" from National Institute of General Medical Sciences, dated Jan. 2018 (3 pages).
Shaklee et al., Hydrazinolysis of heparin and other glycosaminoglycans. Biochem. J. (1984); 217: 187-197.
Shapiro et al., Cellular control of abscess formation: role of T cells in the regulation of abscesses formed in response to Bacteroides fragilis. J Immunol. Jul. 1, 1986;137(1):341-6.
Shapiro et al., Cellular immunity to Bacteroides fragilis capsular polysaccharide. J Exp Med. Apr. 1, 1982;155(4):1188-97.
Sharpe et al., The B7-CD28 superfamily. Nat Rev Immunol. Feb. 2002;2(2): 116-26. Review.
Shevach, CD4+ CD25+ suppressor T cells: more questions than answers. Nat Rev Immunol. Jun. 2002;2(6):389-400. Review.
Sigmundsdottir H, et al. (2007) DCs metabolize sunlight-induced vitamin D3 to 'program' T cell attraction to the epidermal chemokine CCL27. Nature immunology 8: 285-293.
Silvestro et al. "Effects of subinhibitory concentrations of clindamycin on the morphological, biochemical and genetic characteristics of Bacteroides fragilis" FEMS Microbiol. Lett. 2006; vol. 257; No. 2; pp. 189-194.
Simmons et al., Synthesis and membrane permeability of PNA-peptide conjugates. Bioorg Med Chem Lett. 1997;7(23):3001-6.
Slack, E., et al. (2009). Innate and adaptive immunity cooperate flexibly to maintain host-microbiota mutualism. Science 325, 617-620.
Smith et al. "Use of axenic animals in studying the adaptation of mammals to their commensal intestinal microbiota", Semin Immunol., Apr. 2007, pp. 59-69, vol. 19, Issue 2, Elsevier, Amsterdam, Netherlands.
Smith SG et al. Functional analysis of the FimE integrase of *Escherichia coli* K-12: isolation of mutant derivatives with altered DNA inversion preferences. (1999) Mol Microbiol 34:965-79.
Smits, H.H. et al. "Selective probiotic bacteria induce IL-10-producing regulatory T cells in vitro by modulating dendritic cell

(56) References Cited

OTHER PUBLICATIONS function through dendritic cell-specific intercellular adhesion molecule 3-grabbing nonintegrin" J Allergy Clin Immunol. (2005) pp. 1260-1267.
Solomon AJ, et al. "Multiple Sclerosis and Vitamin D: A Review and Recommendations" Curr. Neurol Neurosci Rep.; 2010; vol. 10; pp. 389-396.
Spach KM, et al. (2005) Vitamin D3 confers protection from autoimmune encephalomyelitis only in female mice. J Immunol 175: 4119-4126.
Spach KM, et al. (2004) Gene expression analysis suggests that 1,25-dihydroxyvitamin D3 reverses experimental autoimmune encephalomyelitis by stimulating inflammatory cell apoptosis. Physiol Genomics 18: 141-151.
Sprinz, H. et al. (1961) The response of the germfree guinea pig to oral bacterial challenge with *Escherichia coli* and Shigella flexneri. Am J. Pathol. 39, 681-695.
Stefanelli et al., "New insights into inflammatory bowel disease pathophysiology: paving the way for novel therapeutic targets", Current Drug Targets, May 2008, pp. 413-418, vol. 9, No. 5.
Stein et al., Thymus-independent and thymus-dependent responses to polysaccharide antigens. J Infect Dis. Jun. 1992;165 Suppl I:S49-52. Review.
Stenvinkel et al., "IL-10, IL-6, and TNF-a: central factors in the altered cytokine network of uremia—the good, the bad, and the ugly", Kidney International, Apr. 2005, pp. 1216-1233, vol. 67, Issue 4, Elsevier, New York City, NY.
Stephen et al. "Effect of 87-2 and CD40 Signals from Activated Antigen-Presenting Cells on the Ability of Zwitterionic Polysaccharides to Induce T-Cell Stimulation" 2005; Inf. Immun. vol. 73; pp. 2184-2189.
Stewart N, et al. (2012) Interferon-beta and serum 25-hydroxyvitamin D interact to modulate relapse risk in MS. Neurology 79: 254-260.
Stingele et al., "Zwitterionic Polysaccharides Stimulate T Cells with No Preferential Vbeta Usage and Promote anergy, Resulting in Protection against Experimental Abscess Formation", The Journal of Immunology, Feb. 1, 2004, pp. 1483-1490, vol. 172, Issue 3.
Stockinger et al., "Differentiation and function of Th17 T cells", Current Opinion in Immunology, Jun. 2007, pp. 281-286, vol. 19, Issue 3.
Strachan et al. "Hayfever, hygiene, and household size", BMJ, Nov. 18, 1989, pp. 1259-1260, 299 (6710).
Strauch et al., "Influence of intestinal bacteria on induction of regulatory T cells: lessons from a transfer model of colitis", Gut, Jun. 29, 2005, pp. 1546-1552, vol. 54, Issue 11.
Strober, "The multifaceted influence of the mucosal microflora on mucosal dendritic cell responses", Immunity, Sep. 18, 2009, pp. 377-388, vol. 31, Issue 3.
Stromnes IM, et al. (2006) Active induction of experimental allergic encephalomyelitis. Nat Protoc 1: 1810-1819.
Stromnes et al., Passive induction of experimental allergic encephalomyelitis. Nat Protoc. 2006; 1(4): 1952-60.
Stumhofer et al., "Interleukins 27 and 6 induce STAT3-mediated T cell production of interleukin 10", Nat Immunol, Nov. 11, 2007, pp. 1363—1371, 8.
Supplementary European Search Report for EP Application No. EP2217250, dated Dec. 8, 2010, 2 pages.
Suri-Payer et al., CD4+CD25+ T cells inhibit both the induction and effector function of autoreactive T cells and represent a unique lineage of immunoregulatory cells. J Immunol. Feb. 1, 1998; 160(3): 1212-8.
Sutmeuller et al., "Toll-like receptor 2 controls expansion and function of regulatory T cells", J. Clin. Invest., Feb. 1, 2006, pp. 485-494, vol. 116, Issue 2.
Szu et al., Relation between structure and immunologic properties of the Vi capsular polysaccharide. Infect Immun. Dec. 1991;59(12):4555-61.
Takatori, N. "Probiotics, beneficial bacteria, and inflammatory bowel disease; What do we actually know?" Nutritional Bytes, 2009, vol. 13, pp. 1-6.

Tanaka, H. et al. "Human monocyte-derived dendritic cells induce naive T cell differentiation into T helper cell type 2 (Th2) of Th1/Th2 effectors: role of stimulator/responder ratio" Journal of Experimental Medicine; vol. 192; No. 3; Aug. 7, 2000; pp. 405-411.
Tang et al., Th type 1-stimulating activity of lung macrophages inhibits Th2-mediated allergic airway inflammation by an IFN-gamma-dependent mechanism. J Immunol. Feb. 1, 2001; 166(3): 1471-81.
Tang, et al. "In-vitro-expanded Antigen-specific Regulatory T cells suppress autoimmune diabetes" J. Exp. Med. Vol. 199; No. 11; Jun. 7, 2004; pp. 1455-1465.
Taurog et al., "The germfree state prevents development of gut and joint inflammatory disease in HLA-B27 transgenic rats", J Exp Med., Dec. 1, 1994, pp. 2359-2364, 180 (6).
Taylor et al., Stoichiometric depolymerization of polyuronides and glycosaminoglycuronans to monosaccharides following reduction of their carbodiimide-activated carboxyl groups. Biochemistry. Apr. 11, 1972;11 (8): 1383-8.
Teitelbaum et al., Immunomodulation of experimental autoimmune encephalomyelitis by oral administration of copolymer 1. Proc Natl Acad Sci USA. Mar. 30, 1999;96(7):3842-7.
Teitelbaum et al., Specific inhibition of the T-cell response to myelin basic protein by the synthetic copolymer Cop 1. Proc Natl Acad Sci USA. Dec. 1988;85(24):9724-8.
Teitelbaum et al., Synthetic copolymer 1 inhibits human T-cell lines specific for myelin basic protein. Proc Natl Acad Sci USA. Jan. 1, 1992;89(1):137-41.
Teitelbaum et al., Unprimed spleen cell populations recognize macrophage-bound antigen with opposite net electric charge. Proc Natl Acad Sci USA. Apr. 1977;74(4):1693-6.
Telesford, et al., "A commensal symbiotic factor derived from Bacteroides fragilis promotes human CD39+Foxp3+ T cells and Treg function," Gut Microbes, vol. 6: 234-242. Published online Jul. 31, 2015. 10 Pages.
The Language of Prevention, National Public Health Partnership, 2006, 9 pages.
Thomas et al., Randomised controlled trial of short bursts of a potent topical corticosteroid versus prolonged use of a mild preparation for children with mild or moderate atopic eczema. BMJ. 2002;324(7640):1-7.
Tong et al., "Mouse Models of Colorectal Cancer," Chin. J. Cancer, vol. 30, 450-62 (2011).
Torisu M., et al., "Significant Prolongation of Disease-Free Period Gained by Oral Polysaccharide K (PSK) Administration after Curative Surgical Operation of Colorectal Cancer," Cancer Immunology, Immunotherapy, vol. 31(5), Sep. 1, 1990, 8 pages, XP055323922.
Tournoy et al., Endogenous interleukin-10 suppresses allergen-induced airway inflammation and nonspecific airway responsiveness. Clin Exp Allergy. Jun. 2000;30(6):775-83.
Toussirot, E., et al., Bacterial extract (OM-89) specific and non specific immunomodulation in rheumatoid arthritis patients, Autoimmunity 2006, 39: 299-306 Abstract Only.
Triantafillidis et al., "Colorectal Cancer and Inflammatory Bowel Disease: Epidemiology, Risk Factors, Mechanisms of Carcinogenesis and Prevention Strategies," Anticancer Res., vol. 29, 2727-37 (2009).
Troy, E. et al. "Beneficial effects of Bacteroides fragilis polysaccharides on the immune system." Front Biosci., Jan. 1, 2010, vol. 15; pp. 25-34.
Troy, E. et al., "Orientations of the Bacteroides fragilis capsular polysaccharide biosynthesis locus promoters during symbiosis and infection", Journal of Bacteriology, Nov. 2010, vol. 192, No. 21, pp. 5832-5836.
Turnbaugh et al., "An obesity-associated gut microbiome with increased capacity for energy harvest", Nature, Dec. 21, 2006, pp. 1027-1031, 444(7122).
Turnbaugh et al., "The human microbiome project: exploring the microbial part of ourselves in a changing world", Nature, Oct. 18, 2007, pp. 804-810. vol. 449, Issue 7164.
Tzianabos et al., "The Capsular Polysaccharide of Bacteroides fragilis Comprises Two Ionically Linked Polysaccharide," J. Biol. Chem., vol. 267, 18230-5 (1992).

(56) References Cited

OTHER PUBLICATIONS

Tzianabos et al. "Structural Characteristics of Polysaccharides that Induce Protection Against Intra-Abdominal Abscess Formation" Infection and Immunity, Nov. 1, 1994, pp. 4881-4886, vol. 62, No. 11.

Tzianabos et al. "T-Cells Activated by Zwitterionic Molecules prevent abscesses induced by pathogenic bacteria" J. Biol. Chem. 2000; vol. 275; No. 10; pp. 6733-6740.

Tzianabos et al., Bacterial structure and functional relation to abscess formation. Infect Agents Dis. Oct. 1994;3(5):256-65. Review.

Tzianabos et al., Characteristics of bacterial polysaccharides that activate T cells. The International Carbohydrate Symposium XVII. Jul. 21, 1994. 1 page.

Tzianabos et al., Effect of surgical adhesion reduction devices on the propagation of experimental intra-abdominal infection. Arch Surg. Nov. 1999;134(11):1254-9.

Tzianabos et al., IL-2 mediates protection against abscess formation in an experimental model of sepsis. J Immunol.Jul. 15, 1999;163(2):893-7.

Tzianabos et al., Structure-function relationships for polysaccharide-induced intra-abdominal abscesses. Infect Immun. Aug. 1994;62(8):3590-3.

Tzianabos et al., T Cell Activation by Zwitterionic polysaccharides and peptide mimetics prevents intrabdominal abscess formation. Abstracts of the 99th General Meeting of the American Society for Microbiology. Chicago, US: May 30-Jun. 3, 1999. Jun. 28, 1999; 1 page.

Tzianabos, A.O., Polysaccharide Immunomodulators as Therapeutic Agents: Structural Aspects and Biologic Function, Clin. Microbial. Rev. 13(4):523-533 (2000).

Tzianabos, AO et al., Polysaccharide-mediated protection against abscess formation in experimental intra-abdominal sepsis. J Clin. Investi. (1995) 96:2727-31.

Tzianabos, et al., Structural rationale for the modulation of abscess formation by *Staphylococcus aureus* capsular polysaccharides. Proc Natl Acad Sci USA. Jul. 31, 2001 ;98(16):9365-70. Epub Jul. 24, 2001.

Uronis et al., "Modulation of the Intestinal Microbiota Alters Colitis-Associated Colorectal Cancer Susceptibility," PLoS ONE, vol. 4, e6026 (2009).

Van Maren et al., "Toll-like receptor signalling on Tregs: to suppress or not to suppress?", Immunology, Aug. 2008, pp. 445-452, vol. 124, Issue 4.

Van Scott et al., IL-10 reduces Th2 cytokine production and eosinophilia but augments airway reactivity in allergic mice. Am J Physiol Lung Cell Mol Physiol. Apr. 2000;278(4):L667-74.

Vann et al., The structure of the capsular polysaccharide (K5 antigen) of urinary-tract-infective *Escherichia coli* 010:K5:H4. A polymer similar to desulfo-heparin. Eur J Biochem. May 15, 1981; 116(2):359-64.

Veldhoen, M. et al. "TGF beta in the context of an inflammatory cytokine milieu supports de novo differentiation of IL-17-producing T cells." Immunity; vol. 24; pp. 179-189.

Velez et al., Type I *Streptococcus pneumoniae* carbohydrate utilizes a nitric oxide and MGC 11-dependent pathway for antigen presentation. Immunol. 2008; 127:73-82.

Verdu et al., Oral administration of antigens from intestinal flora anaerobic bacteria reduces the severity of experimental acute colitis in BALB/c mice. Clin Exp Immunol. Apr. 2000;120(1):46-50.

Videla et al., "Role of intestinal microflora in chronic inflammation and ulceration of the rat colon", Gut, 1994, pp. 1090-1097, vol. 35, Issue 8.

Vignali, DA et al. "How regulatory T cells work." Nat. Rev. Immunol.; 2008; vol. 8; pp. 523-532.

Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.

Viret et al., Molecular cloning and characterization of the genetic determinants that express the complete Shigella serotype D (Shigella sonnei) lipopolysaccharide in heterologous live attenuated vaccine strains. Mol Microbial. Jan. 1993;7(2):239-52.

Wagner et al., Use of reporter cells to study endogenous retinoid sources in embryonic tissues. Methods Enzymol. 1997;282:98-107.

Wang et al., "A bacterial carbohydrate links innate and adaptive responses through Toll-like receptor 2," J. Exp. Med., vol. 203, 2853-63 (2006).

Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.

Wang et al., Ozonolysis for selectively depolymerizing polysaccharidescontaining β-d-aldosidic linkages. Proc Natl Acad Sci USA. Jun. 9, 1998; 95(12): 6584-6589.

Wang et al., Structure characterization of an abscessogenic capsular polysaccharide from Bacteriodes fragilis by NMR spectroscopy. XIX International Conference of NMR in Biological Systems. Florence, Italy Aug. 20-25, 2000. Abstract.

Ward et al., The nucleotide sequence of the tnpA gene ofTn21, Nucleic Acids Research, vol. 15(4), 1987, 1799-1806.

Wehr et al., Anti-low-density lipoprotein antibodies in alcoholics without and with liver disease and in social drinkers. Alcohol & Alcoholism Jan.-Feb. 1997;32(1):43-9.

Weinacht et al. Phase variation of the capsular polysaccharides of Bacteroides fragilis is dictated by site-specific recombinases. 2002 General Meeting of the American Society for Microbiology, May 19-23, 2002. Abstract.

Wen, L. et al. "Innate immunity and intestinal microbiota in the development of Type 1 diabetes" Nature; 2008; vol. 455; pp. 1109-1113.

Wessels et al., Structural Determination and Immunochemical Characterization of the Type V Group B *Streptococcus* Capsular Polysaccharide, The Journal of Biological Chemistry, 266:6714-6719, 1991.

Wessels et al., Structure and immunochemistry of an oligosaccharide repeating unit of the capsular polysaccharide of Type 111 group B *Streptococcus*. A revised structure for the type 111 group B streptococcal polysaccharide antigen. J Biol Chem. Jun. 15, 1987;262(17):8262-7.

Wexler, Bacteroides: the good, the bad, and the nitty-gritty. Clin Microbial Rev. Oct. 2007;20(4):593-621.

Whitfield, Biosynthesis and assembly of capsular polysaccharides in *Escherichia coli*. Annu Rev Biochem. 2006;75:39-68.

Wiegandt et al., Carbohydrate Components of Extraneuronal Gangliosides from Bovine and Human Spleen, and Bovine Kidney, European Journal of Biochemistry, 15:287-292, 1970.

Wilier CJ, et al. (2003) Twin concordance and sibling recurrence rates in multiple sclerosis. Proc Natl Acad Sci USA 100: 12877-12882.

Wingate K. et al., "25-Hydroxyvitamin D Concentrations in Children with Crohn's Disease Supplemented with Either 2000 or 400 IU Daily for 6 Months: A Randomized Controlled Study" The Journal of Pediatrics, vol. 164, No. 4,Apr. 2014, pp. 860-865 6 pages.

Wirtz et al., Mouse models of inflammatory bowel disease. Adv Drug Deliv Rev. Sep. 30, 2007;59(11):1073-83. Eoub Aug. 16, 2007.

Woessner et al., Long-term antibiotic treatment with roxithromycin in patients with multiple sclerosis. Infection. Dec. 2006;34(6):342-4.

Wong et al., "Activation of Peripheral Th17 Lymphocytes in Patients with Asthma", Immunological Investigations, Sep. 19, 2009, pp. 652-664, vol. 38, Issue 7.

Woodruff, et al., Sudden-onset severe acute asthma: Clinical features and response to therapy, Academic Emergency Med. 1998, 5: 695-701.

Wu HJ, et al. (2010) Gut-residing segmented filamentous bacteria drive autoimmune arthritis via T helper 17 cells. Immunity 32: 815-827.

Wujek et al., A carbohydrate polymer that effectively prevents epidural fibrosis at laminectomy sites in the rat. Exp Neural. Nov. 1991;114(2):237-45.

Xavier et al. "Unravelling the pathogenesis of inflammatory bowel disease", Nature, Jul. 26, 2007, pp. 427-434, 448.

(56) References Cited

OTHER PUBLICATIONS

Xavier, R. & Podolsky, D. K. Commensal flora: wolf in sheep's clothing. Gastroenterology 128, 1122-6 (2005).
Xie & Itzkowitz, "Cancer in inflammatory bowel disease," World J. Gastroenterol., vol. 14, 378-89 (2008).
Xu J et al., A genomic view of the human-Bacteroides thetaiotaomicron symbiosis. Science. Mar. 28, 2003;299(5615):2074-6.
Yamakazi et al. "Dendritic cells are specialized accessory cells along with TGF-beta for the differentiation of Foxp3+ CD4+ regulatory T cells from peripheral Foxp3-precursors" Blood. 2007; 110: 4293-4302.
Yamazaki, T. et al. "CCR6 regulates the migration of inflammatory and regulatory T cells" J. Immunology; 2008; vol. 181; pp. 8391-8401.
Yang J. et al., "Targeting Th17 cells in autoimmune diseases" Cell Press, vol. 35, No. 10,Oct. 2014, pp. 493-500 8 pages.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.
Young et al., "In vitro and in vivo characterization of Helicobacter hepaticus cytolethal distending toxin mutants", Infect Immun., May 2004, pp. 2521-2527, vol. 72 No. 5.
Zabad et al., The clinical response to minocycline in multiple sclerosis is accompanied by beneficial immune changes: a pilot study. Mult Scler. May 2007;13(4):517-26. Epub Feb. 9, 2007.
Zaleznik et al., A soluble suppressor T cell factor protects against experimental intraabdominal abscesses. J Clin Investi. Mar. 1985;75(3):1023-7.
Zaph, C., et al. (2008). Commensal-dependent expression of IL-25 regulates the IL-23-IL-17 axis in the intestine. J Exp Med 205, 2191-2198.
Zehnder D, et al. (1999) Expression of 25-hydroxyvitamin D3-1 alpha-hydroxylase in the human kidney. J Am Soc Nephrol 10: 2465-2473.
Zehnder D, et al. (2001) Extrarenal expression of 25-hydroxyvitamin d(3)-1 alpha-hydroxylase. J Clin Endocrinol Metab 86: 888-894.
Zhang et al., Degradation of Wood Polysaccharide Model Compounds During Ozone Treatment. Journal of Pulp and Paper Science. Jan. 1997;23(1):J23-J27.
Zhang X., et al., "Calcium, Vitamin D and Colorectal Cancer Chemoprevention," Bailliere's Best Practice and Research, Clinical Gastroenterology, vol. 25(4), Jan. 1, 2011, 10 pages.
Zhang et al., IL-10 is involved in the suppression of experimental autoimmune encephalomyelitis by CD25+CD4+ regulatory T cells. Int Immunol. Feb. 2004;16(2):249-56.
Zhao H et al. In vivo phase variation of MR/P fimbrial gene expression in Proteus mirabilis infecting the urinary tract. (1997) Mol Micro biol 23: 1009-19.
Zhou, L. et al. "TGF-beta-induced Foxp3 inhibits T(H)17 cell differentiation by antagonizing RORgammat function" Nature; 2008; vol. 453; pp. 236-240.
Zhu et al., Oral administration of type-11 collagen peptide 250-270 suppresses specific cellular and humoral immune response in collagen-induced arthritis. Clin Immunol. Jan. 2007; 122(1):75-84. Epub Oct. 11, 2006.
Davila et al., "Efficacy and Toxicity Management of 19-28z CAR T Cell Therapy in B Cell Acute Lymphoblastic Leukemia," Sci Transl Med 2014, 6(224), in 23 pages.
Examination Report dated Apr. 7, 2021 in Canadian Patent Application No. 2,911,826.
Final Office Action dated Jan. 25, 2021 in U.S. Appl. No. 16/151,793.
Final Office Action dated Feb. 9, 2021 in U.S. Appl. No. 16/562,358.
Fichtner-Feigl et al., "Treatment of murine Th1- and Th2-mediated inflammatory bowel disease with NF-κB decoy oligonucleotides," The Journal of Clinical Investigation 2005, 115(11), 3057-3071.
Head & Jurenka, "Inflammatory Bowel Disease Part I: Ulcerative Colitis—Pathophysiology and Conventional and Alternative Treatment Options," Alternative Medicine Review 2003, 8(3), 247-283.
Li & He, "I L-10 and its related cytokines for treatment of inflammatory bowel disease," World Journal of Gastroenterology 2004, 10(5), 620-625.
Non-Final Office Action dated Apr. 19, 2021 in U.S. Appl. No. 16/386,522.
Non-Final Office Action dated May 18, 2021 in U.S. Appl. No. 16/562,358.
Notification of Reasons for Refusal for Japanese Patent Application No. 2019-061261 dated Jan. 26, 2021, in 7 pages.
Notification of Reasons for Refusal dated Feb. 26, 2021 in Japanese Patent Application No. 2020-006703.
Notification of Reasons for Refusal dated Mar. 3, 2021 in Japanese Patent Application No. 2020-006706.
Final Office Action dated Oct. 4, 2021 in U.S. Appl. No. 16/562,358.
Final Office Action dated Oct. 21, 2021 in U.S. Appl. No. 16/388,522.
Non-Final Office Action dated Aug. 19, 2021 in U.S. Appl. No. 16/151,793.
Notice of Allowance dated Aug. 20, 2021 in Japanese Patent Application No. 2020-006703.
Notification of Reasons for Refusal dated Aug. 13, 2021 in Japanese Patent Application No. 2020-006706.

\* cited by examiner

SEQUENCE LISTING

<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 1
agctatgaat ctactaagag agggaca                      27

<210> SEQ ID NO 2
<211> LENGTH: 25
<212> TYPE: DNA
<213> ORGANISM: Artificial Sequence
<220> FEATURE:
<223> OTHER INFORMATION: synthetic polynucleotide

```
<400> SEQUENCE: 2
gtcctagtag ggaggtgtga agttg                                          25

<210> SEQ ID NO 3
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 3
ttaaggttct ctcctctgaa                                                20

<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4
tagggagcta aattatccaa                                                20

<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5
acggcatgga tctcaaagac                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
gtgggtgagg agcacgtagt                                                20

<210> SEQ ID NO 7
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 7
ctggacaaca tactgctaac cg                                             22

<210> SEQ ID NO 8
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 8
gggcatcact tctaccaggt aa                                             22

<210> SEQ ID NO 9
<211> LENGTH: 18
```

```
<212> TYPE: DNA
<213> ORGANISM: Artificial Sequence
<220> FEATURE:
<223> OTHER INFORMATION: synthetic polynucleotide

<400> SEQUENCE: 9
ccgctgagag ggcttcac                                                    18

<210> SEQ ID NO 10
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 10
tgcaggagta ggccacatta ca                                               22

<210> SEQ ID NO 11
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 11
atcctgaact tctatcagct ccac                                             24

<210> SEQ ID NO 12
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 12
gcatttagct atgtgcttct gtttc                                            25

<210> SEQ ID NO 13
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 13
ctgttgctgc taccttgct t                                                 21

<210> SEQ ID NO 14
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 14
cactcctggc aatcgagatt c                                                21
```

SEPSIS TREATMENT AND RELATED COMPOSITIONS METHODS AND SYSTEMS

CROSS REFERENCE TO RELATED APPLICATIONS

This application claims priority to U.S. Provisional Application entitled "A Microbiome based Therapy for Sepsis through Induction of Marginal Zone B Cell Activity" Ser. No. 62/173,497 filed on Jun. 10, 2015 Docket No. CIT 7209-P, the disclosure of which is incorporated herein by reference in its entirety.

FIELD

The present disclosure relates to the immune system, and, in particular, to sepsis treatment in an individual and related compositions methods and systems.

BACKGROUND

Sepsis is a life-threatening condition that arises when the body's response to infection injures its own tissues and organs.

Despite development of various approaches to treat sepsis, effective treatment of sepsis in individuals remains challenging with the risk of death from sepsis being as high as 30%, severe sepsis as high as 50%, and septic shock as high as 80% of the individuals affected.

SUMMARY

Provided herein, are compositions and related methods and systems that are suitable to treat or prevent sepsis or a condition associated to sepsis, in an individual.

According to a first aspect, a method to treat an individual with sepsis or a condition associated thereto is described. The method comprises systemically administering to the individual an amount of a zwitterionic polysaccharide effective to treat sepsis or the condition associated thereto in the individual.

According to a second aspect, a method to prevent sepsis or a condition associated thereto in an individual at risk of sepsis is described. The method comprises systemically administering to the individual at risk of sepsis or the condition associated thereto, an effective amount of a zwitterionic polysaccharide effective to prevent sepsis or the condition associated thereto in the individual.

According to a third aspect, a pharmaceutical composition for sepsis treatment and/or prevention is described. The composition comprises one or more zwitterionic polysaccharides in an amount effective to treat and/or prevent sepsis or a condition associated theretof and a pharmaceutically acceptable vehicle. In some embodiments, the pharmaceutical composition further comprises one or more antibiotics and/or one or more antiviral agent.

According to a fourth aspect, a system to treat and/or prevent sepsis or a condition associated thereto is described. The system comprises at least two of: one or more zwitterionic polysaccharides and with one or more antibiotics and/or antiviral agents for simultaneous combined or sequential administration according to methods to treat or prevent sepsis or a condition associated thereto herein described.

The compositions and methods herein disclosed can be used in several embodiments to suppress disseminated inflammation and treat sepsis or an associated condition in affected individuals.

The compositions and methods herein disclosed can be used in several embodiments to prevent sepsis or a condition associated thereto in individuals at risk of blood infection and in particular at risk of blood infection by bacteria.

The compositions and methods herein described can be used in connection with medical, pharmaceutical, veterinary applications as well as fundamental biological studies and various applications, identifiable by a skilled person upon reading of the present disclosure, wherein treating, preventing and/or investigating sepsis is desirable The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 1, Panel (C) is a diagram reporting percent survival of animals treated with PSA and PBS as reported in FIG. 1 Panels A and B. FIG. 1, Panel (D) shows a survival curve in a cecal-ligation puncture (CLP) model following treatment with PSA, PBS and surgery to repair the cecal-ligation puncture in the animal (sham) All experiments contained an n of at least four in each group and were repeated at least twice.

FIG. 2 Panels (A) and (B) show detection of TNF-α (Panel A) and IL-6 (Panel B) by ELISA in serum of Balb/c animals treated intraperitoneally with high doses of LPS (500 ug) and subsequently treated intravenously with PBS, PSA (PSA same) or PSA administered 30 minutes post-LPS (PSA post). Each experiment consists of at least 4 animals in each group and was repeated twice. * p<0.05 **p<0.005 as measured by a student's t-test. FIG. 2 Panel (C) show the percent survival of animals treated as in the experiments leading to the results of FIG. 2 Panels A and B. *p<0.05 **p<0.005 using a logrank and Gehan-Wilcoxon test.

FIG. 3 Panel (A) shows TNF-α detection by ELISA in serum of RAG$^{-/-}$ animals treated intravenously with either PBS or PSA 24 hours prior to receiving high dose LPS intraperitoneally. FIG. 3 Panel (B) shows the percent survival of the animals treated as the percent survival of animals treated as in the experiments leading to the results of FIG. 3 Panel A. Two experiments were combined. *p<0.05 **p<0.005 using a logrank and Gehan-Wilcoxon test. FIG. 3 Panels (C) show TNF-a detected in serum of RAG$^{-/-}$ recipients of either CD4+CD3+ or total T cells (CD3+) or CD4 depleted splenocytes (includes CD8+ T cells and CD19+ B cells) after LPS administration. FIG. 3 Panel (D) show the percent survival of animals treated as in the experiments leading to the results of FIG. 3 Panel (C) (CD4 depleted, CD3+transfer CD4+transfer). FIG. 3 Panel (E) shows TNF-A detected in RAG$^{-/-}$ recipients of sort purified CD19+ total B cells purified from the spleen of donor animals FIG. 3 Panel (F) show the percent survival of animals treated as in the experiments leading to the results of FIG. 3 Panel (E)* $p<0.05$ **$p<0.005$ by a student's t-test for all ELISA data and *$p<0.05$ **$p<0.005$ using a logrank and Gehan-Wilcoxon test for survival data. ELISA data is representative from one experiment repeated twice with an n of 4 in each group. Survival data combines multiple experiments.

FIG. 4 panel A shows TNF-α detected in serum of Marginal zone B cells (CD19+B220+IgM$^{hi}$CD21$^{hi}$CD23) were sort purified and transferred into RAG$^{-/-}$ recipients. Twenty-four hours later these animals were given high dose LPS and serum collected at 1 and 4 hours to assay for TNF-α (A) FIG. 4 Panel (B) show the percent survival of animals treated as in the experiments leading to the results of FIG. 4 Panel (A). FIG. 4 Panel (C) shows TNF-α detected in serum of RAG$^{-/-}$ recipients of $8\times10^5$ MZ B cells from WT C57Bl/6 animals were treated i.v. with either PBS or PSA (100 ug), the $10^5$ MZ B cells sort purified as in the experiments of FIG. 4 panel (A), following administration in the RAG$^{-/-}$ recipients of high dose LPS (500 ug). FIG. 4 Panel (D) show the percent survival of animals treated as in the experiments leading to the results of FIG. 4 Panel (C) * $p<0.05$ **$p<0.005$ by a student's t-test for all ELISA data and *$p<0.05$ **$p<0.005$ using a logrank and Gehan-Wilcoxon test for survival data. FIG. 4 Panel (E) shows a detected concentration of TNFA-a in animals either treated with PBS or treated with i.v. PSA and subsequently induced for sepsis. FIG. 4 Panel (F) shows a percent survival in animals that did or did not receive MZ B cells from sIgM$^{-/-}$ mice following either PBS treatment or treatment i.v. with PSA and subsequently induced for sepsis FIG. 5 panel shows that inflammation occurring at the intesting can also impact extra-intestinal sites. In particular, FIG. 5 Panel A shows detection of TNF-a, IL17, IL-6, IL10 expression in CD4+ T cells isolated from spleen of animals following colitis induction subsequent to administration of PSA or vehicle. FIG. 5 Panel C shows the disease score of the colons of Balb/c animals for crypt loss and inflammation from a blinded pathologist following intravenous treatment with PSA (sys) or PBS, 24 hours prior to induction of TNBS colitis in comparison with a control. FIG. 5 Panel D shows the percent survival of the animals treated as in FIG. 5 Panel C.

FIG. 6 Panels C and A show detection of TNF-a in TLR2$^{-/-}$ or IL-10$^{-/-}$ mice treated intravenously treated i.v. with PBS or PSA directly following induction of endotoxin shock by intraperitoneal administration of high doses of LPS (500 ug). FIG. 6 Panels D and B shows the percent survival of the mice treated as indicated in FIG. 6 Panels C and A.

FIG. 7 Panel A shows percent survival of mice that received MZ B transplant from PSA treated mice or MZB transplant from mock treated mice following induction of endotoxin shock by intraperitoneal administration of high doses of LPS (500 ug). FIG. 7 Panel B shows the IL-6 detected ELISA in serum of the$^-$ mice treated as indicated in FIG. 7 Panel A at 30 minutes, 1 hr and 4 hrs following induction of endotoxin shock (PBS treated donor, PSA treated donor).

FIG. 8 shows IgM production in mice treated as indicated in FIG. 7 Panel A at 1 hr and 4 hrs following induction of endotoxin shock.

DETAILED DESCRIPTION

Figure 1:
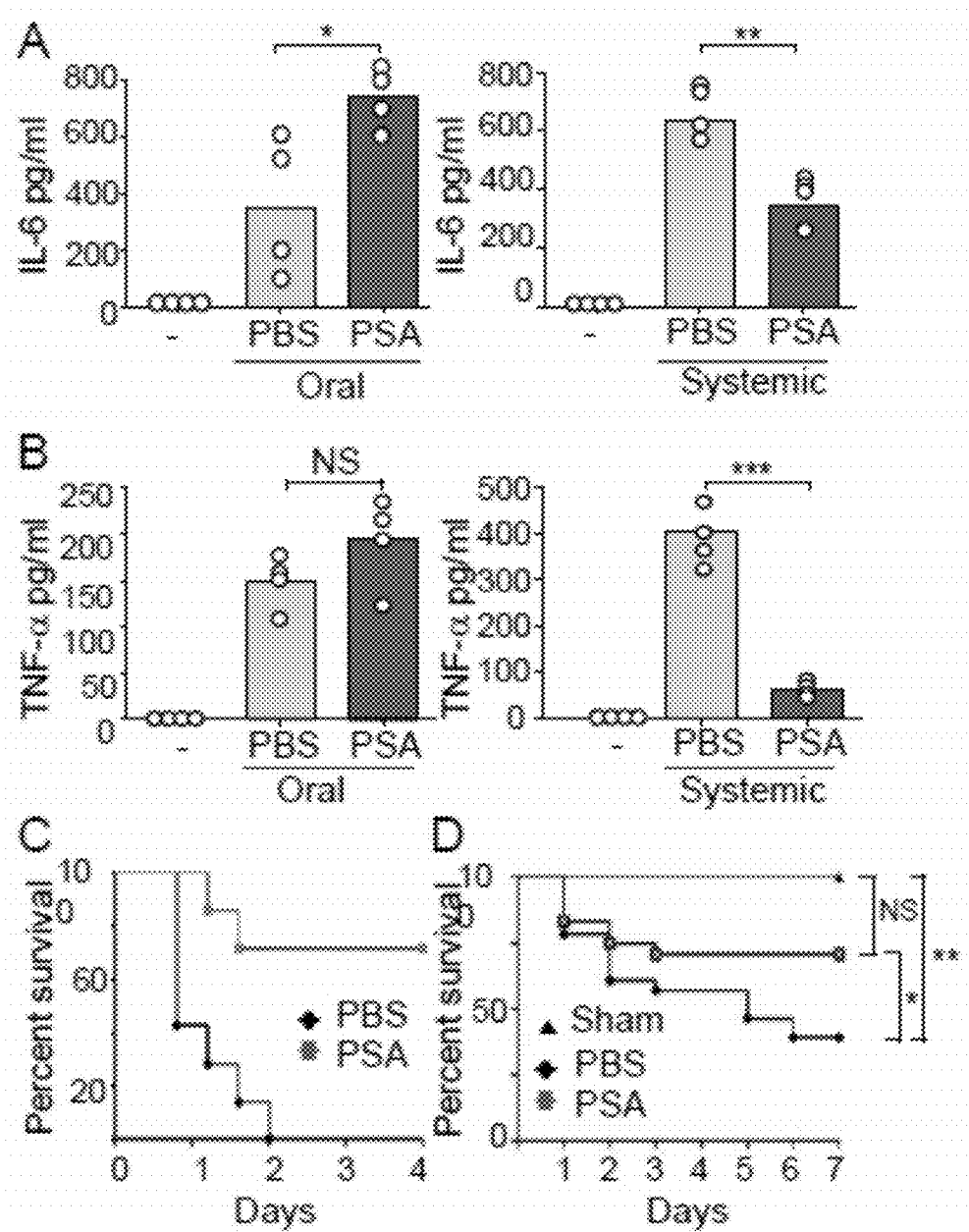
FIG. 1 illustrates data showing that PSA has anti-inflammatory effects outside of the intestine of an individual. In particular, FIG. 1 Panel (A) and Panel (B) are diagrams showing IL-6 (Panel A) and TNF-a (Panel B) detection by q-RT-PCR performed in CD4+ Tcells isolated from spleen of Balb/c animals following oral or systemic (intravenous) treatment with PSA or PBS control, and subsequent colitis induction using TNBS.

Methods and compositions and related system are herein described to treat and/or prevent sepsis in an individual.

The wording "sepsis" as used herein indicates an acute overwhelming inflammatory response to an infection in an individual.

The term "inflammatory response "and "inflammation" as used herein indicate the complex biological response of vascular tissues of an individual to harmful stimuli, such as pathogens, damaged cells, or irritants, and includes secretion of cytokines and more particularly of pro-inflammatory cytokine, i.e. cytokines which are produced predominantly by activated immune cells such as microglia and are involved in the amplification of inflammatory reactions. Exemplary pro-inflammatory cytokines include but are not limited to IL-1, IL-6, TNF-a, IL-17, IL21, IL23, and TGF-β. Exemplary inflammations include acute inflammation and chronic inflammation. The wording "acute inflammation" as used herein indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). The wording "chronic inflammation" as used herein indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis.

Sepsis is caused by an infection triggering an acute and uncontrolled systemic inflammation, which often leads to multiple organ failure and death. The infection is most commonly bacterial, but it can also be from fungi, viruses, or parasites. Common locations for the primary infection include: lungs, brain, urinary tract, skin, and abdominal organs. Systemic inflammations include but are not limited to an inflammatory response in the circulatory system, an inflammatory response which is not confined in a specific organ, and an inflammatory response that extends to a plurality (up to all) tissues and organs in an individual. In particular, sepsis inflammatory response involves a rigorous cytokine response to infection with a surge of inflammatory cytokines, in an effort to promote clearance of infection, that causes host damage including widespread vascular coagulation and 'immune paralysis' due to apoptosis of immune cells and leads to hypotension, multiple organ failure and systemic coagulation. Sepsis results from systemic hyper-immune activation, In methods here described sepsis or a condition associated thereot can be treated or prevented by parenteral administration of PSA or another zwitterionic polysaccharide to an individual.

The term "zwitterionic polysaccharide" as used herein indicates synthetic or natural polymers comprising one or more monosaccharides joined together by glicosidic bonds, and including at least one positively charged moiety and at least one negatively charged moiety. Zwitterionic polysaccharides ("ZPs") include but are not limited to polymers of any length, from a mono- or di-saccharide polymer to polymers including hundreds or thousands of monosaccharides. In some embodiments, a zwitterionic polysaccharide can include repeating units wherein each repeating unit includes from two to ten monosaccharides, a positively charged moiety (e.g. an free positively charged amino moiety) and a negatively charged moiety (such as sulfonate, sulfate, phosphate and phosphonate). In some embodiments, the zwitterionic polysaccharide includes one positive charge and one negative charge on each repeating unit. In some embodiments, a ZP can include 7-12, 12-17, or 15-22 repeating units. In some embodiment ZPs can have a molecular weight comprised between 500 Da and 2,000,000 Da. In some embodiments, the ZPs can have a molecular weight comprised between 200 and 2500. Exemplary ZPS include but are not limited to Polysaccharide A or PSA and Polysaccharide B or PSB from *Bacteroides Fragilis*, CP5/CD8 from *Staphylococcus aureus*, and Sp1/CP1 from *Streptococcus pneumonia*. Zwitterionic polysaccharides can be isolated from natural sources, and in particular from bacterial sources, e.g. by purification. Zwitterionic polysaccharides can also be produced by chemical or biochemical methods, as well as by recombinant microorganism technologies all identifiable by a skilled person. Thus, those methods and technologies will not be further described herein in detail.

The wording "polysaccharide A" as used herein indicates a molecule produced by the PSA locus of *Bacteroides Fragilis* and derivatives thereof which include but are not limited to a polysaccharide of the repeating unit {→3) α-d-AAT Galp(1→4)-[β-d-Galf(1→3)] α-d-GalpNAc (1→3)-[4,6-pyruvate]-β-d-Galp(1→}, where AATGal is acetamido-amino-2,4,6-trideoxygalactose, and the galactopyranosyl residue is modified by a pyruvate substituent spanning 0-4 and 0-6. PSA comprises PSA1 and PSA 2 produced by *B. fragilis* [1, 2]. In particular, PSA naturally produced by B. *Fragilis* comprise a tetrasaccharide repeating unit repeated hundreds of times (U.S. Pat. No. 5,679, 654). PSA2 is a polysaccharide having a pentasaccharide repeating unit containing manoheptose, N-acetylmannosamine, 3-acetoamido-3,6-dideoxyglucose, 2-amino-4-acetomido-2,4,6-trideoxygalactose, fucose, and 3-hydroxybutanoic acid, with a free amine (positively charged moiety) and anionic carboxylate (negatively charged moiety) in each repeating unit. The wording "polysaccharide B" as used herein indicates a molecule produced by the PSA locus of *Bacteroides Fragilis* and derivatives thereof which include but are not limited to polymers of the repeating unit->3-beta-D-QulpNAc-{(1->4)-alpha-D-Galp-[(alpha-L-Fucp-(1->2)-beta-D-GalA-(1->3)-(4-(2-AEP))-beta-D-GlcNac-(1->3)]}-(1->4)-alpha-L-QulpNAc-1->.

The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with PSA in association with the antiseptic activity of PSA. Derivatives of a PSA or another ZPs in the sense of the disclosure can be a fragment of PSA or any other structurally related polysaccharide that comprise the requisite charged groups, and sufficient numbers of repeating units to provide the effects recited in the present disclosure.

Zwitterionic polysaccharide, and in particular PSA and PSB or derivatives thereof that can be used in the methods and systems of the disclosure and related compositions can be naturally occurring or synthetically produced polysaccharides. In some embodiments, the zwitterionic polysaccharide can be PSA1, PSA2 and/or PSB.

In embodiments herein described, one or more ZPs and in particular PSA systemically administered to the individual protects an individual from sepsis and conditions associated thereto, as shown for example by the data in the examples showing PSA ability to protect an individual from inflammation and death in two independent models of sepsis.

The wording "systemic administration" as used herein indicates a route of administration by which an active agent is brought in contact with the body of the individual, so that the desired effect is systemic (i.e. non limited to the specific tissue where the infection and/or inflammation occurs). In particular, in embodiments herein described the administration of PSA or other ZPS can be performed by parenteral administration, a systemic route of administration where a substance is given by a route other than the digestive tract and includes but is not limited to intravenous administration, intra-arterial administration, intramuscular administration, subcutaneous administration, intradermal, administration, intraperitoneal administration, and intravesical infusion.

In some embodiments, administration is performed intravenously by introducing a liquid formulation including one or more ZPs in a vein of an individual using intravenous access methods identifiable by a skilled person, including access through the skin into a peripheral vein. In some embodiments, administration of a ZP is performed intraperitoneally, by injecting a ZP in the peritoneum of an individual, and in particular of animals or humans. Intraperitoneal administration is generally preferred when large amounts of blood replacement fluids are needed, or when low blood pressure or other problems prevent the use of a suitable blood vessel for intravenous injection.

The term "individual" as used herein includes a single biological organism wherein inflammation and in particular sepsis can occur including but not limited to animals and in particular higher animals more particularly vertebrates such as mammals and in particular human beings.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with sepsis are severe sepsis, septic shock, multiple organ dysfunction syndrome (MODS) and systemic inflammatory response syndrome (SIRS) when caused by infection. In particular, severe sepsis septic shock MODS and SIRS are typically associated to sepsis in process that usually begins with infection, and sepsis and results in organ dysfunction. A distinction between those conditions can be made by treating physicians based on different signs and symptoms.

In particular, with reference to sepsis, in addition to symptoms related to the provoking infection, sepsis is frequently associated with fever and/or low body temperature, rapid breathing, elevated heart rate, confusion, and edema. Early signs of sepsis are a fast heart rate, decreased urination, and high blood sugar as will be understood by a skilled person.

Symptoms of severe sepsis comprise confusion, metabolic acidosis (which may be accompanied by faster breathing leading to a respiratory alkalosis), low blood pressure due to decreased systemic vascular resistance, higher cardiac output, and dysfunctions of blood coagulation (where clotting can lead to organ failure).

Septic shock indicates a subclass of distributive shock, a condition in which abnormal distribution of blood flow in the smallest blood vessels results in inadequate blood supply to the body's tissues, resulting in ischemia and organ dysfunction. Septic shock can be defined as sepsis-induced hypotension that persists despite treatment with intravenous fluids Low blood pressure reduces tissue perfusion pressure, causing the tissue hypoxia that is characteristic of shock. Cytokines released in a large scale inflammatory response result in massive vasodilation, increased capillary permeability, decreased systemic vascular resistance, and hypotension and in an attempt to offset decreased blood pressure, ventricular dilatation and myocardial dysfunction occur. The drop in blood pressure seen in sepsis can lead to shock. This may result in light-headedness. Bruising or intense bleeding may also occur.

Multiple organ dysfunction syndrome (MODS) indicates a condition in which the presence of altered organ function in acutely ill patients such that homeostasis cannot be maintained without intervention. MODS usually involves two or more organ systems and is a continuum, with incremental degrees of physiologic derangements in individual organs, in particular is typically in a continuum of severity from sepsis to septic shock to MODS. Accordingly MODS is a process rather than a single event. Alteration in organ function can vary widely from a mild degree of organ dysfunction to completely irreversible organ failure. The degree of organ dysfunction has a major clinical impact as will be understood by a skilled person.

SIRS indicates a serious condition related to systemic inflammation, organ dysfunction, and organ failure. It is a subset of cytokine storm, in which there is abnormal regulation of various cytokines SIRS caused by infection also closely related to sepsis, in which patients satisfy criteria for SIRS and have a suspected or proven infection. Symptoms of SIRS in adults and pediatric identifiable by a skilled person.

One or more of the above conditions can be treated or prevented by administering to an individual with the conditions or at risk of the conditions PSA or another ZPS in an effective amount. The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention reduces the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

Treatment or prevention of sepsis or condition associated thereto encompasses activities directed to achieve in an individual stabilization or improvement of the symptoms, reduction of the extent of the condition, delay or slowing of the progression of the condition, recovery (from the condition, and prolonging survival compared to expected survival in absence of the activities.

In embodiments herein described PSA is provided in effective amount to activate marginal zone (MZ) B cell activity, through a series of events resulting in PSA mediated protection from sepsis independent of T cell response, through IgM production from MZ B cells. The wording "effective amount" indicate an amount sufficient to obtain a desired biological effect such as activation of (MZ) B cell and/or IgM production from (MZ) B cells.

The term "activate" as used herein with reference to a cell indicates a chemical or biological reaction resulting in a modification of the status of the cell that renders the cell active in one or more biological process. Accordingly, activation of cells of the immunitary system results in a modification of the cell status rendering the cell active in immunitary reactions. Activation of a cell of the immunitary system typically but not necessarily involves a capacity to produce antibody and/or the capacity to participate in cell-mediated immunity.

The wording "marginal zone B cells" or "MZ B cells" indicates noncirculating mature B cells that segregate anatomically into the marginal zone (MZ) of the spleen. The marginal zone of the spleen contains multiple subtypes of macrophages, dendritic cells, and B cells. MZ B cells are positioned between the lymphoid tissue of the white pulp and the circulation within the spleen, thereby readily interacting with circulating antigens. Similar to B1 B cells, MZ B cells can be rapidly recruited into the early adaptive immune responses in a T cell independent manner The MZ B cells are especially well positioned as a first line of defense against systemic blood-borne antigens that enter the circulation and become trapped in the spleen. The marginal zone (MZ) B cells are considered to possess "innate like" qualities as they express semi-variant or low diversity B cell receptors (BCRs) that recognize multiple conserved microbial factors. It is believed MZ B cells are especially reactive to bacterial cell wall components and self-antigens which are the products of aging. MZ B cells also display a lower activation threshold than their FO B cell counterparts with heightened propensity for plasma cell differentiation that contributes further to the accelerated primary antibody response. In particular, MZ B cells are involved in the clearance of encapsulated bacteria as upon their activation MZ B cells produce copious amounts of IgM against bacterial polysaccharides. IgM secretion has been implicated in protection from preclinical sepsis. In particular, this rapid antibody response can either neutralize LPS or promote bacterial killing [3]. In rodents, the MZ B-cells and B1 B-cells exhibit an activated phenotype that allows their rapid proliferation and differentiation into Ab-secreting cells upon stimulation with thymus independent (TI) antigens (Ags). MZ B-cells seem to preferentially secrete antibodies of the IgM and IgG3 isotypes. Activated MZ B-cells are potent protein Ag presenters to CD4+ T-cells, and have the ability to induce Ag-specific T-cell clonal expansion both in vitro and in vivo [4].

Accordingly, in some embodiments herein described, PSA and/or other ZPs administration is performed in effective amounts to induce IgM production from MZ-B cells to inhibit inflammation and promote bacterial killing.

The terms "inhibiting" and "inhibit", as used herein indicate the activity of decreasing the biological reaction or process. Accordingly, a substance "inhibits" a certain biological reaction or process if it is capable of decreasing that biological reaction or process by interfering with said reaction or process. For example, a substance can inhibit a certain biological reaction or process by reducing or suppressing the activity of another substance (e.g. an enzyme) associated to the biological reaction or process, e.g. by binding, (in some cases specifically), said other substance. Inhibition of the biological reaction or process can be detected by detection of an analyte associated with the biological reaction or process. The term "detect" or "detection" as used herein indicates the determination of the existence, presence or fact of an analyte or related signal in a limited portion of space, including but not limited to a sample, a reaction mixture, a molecular complex and a substrate. A detection is "quantitative" when it refers, relates to, or involves the measurement of quantity or amount of the analyte or related signal (also referred as quantitation), which includes but is not limited to any analysis designed to determine the amounts or proportions of the analyte or related signal. A detection is "qualitative" when it refers, relates to, or involves identification of a quality or kind of the analyte or related signal in terms of relative abundance to another analyte or related signal, which is not quantified. Inhibition of inflammation can be detected by cytokine detection as it will be understood by a skilled person.

The term "cytokine" as used herein indicates a category of signaling proteins and glycoproteins extensively used in cellular communication that are produced by a wide variety of hematopoietic and non-hematopoietic cell types and can have autocrine, paracrine and endocrine effects, sometimes strongly dependent on the presence of other chemicals. The cytokine family consists mainly of smaller, water-soluble proteins and glycoproteins with a mass between 8 and 30 kDa. Cytokines are critical to the development and functioning of both the innate and adaptive immune response. They are often secreted by immune cells that have encountered a pathogen, thereby activating and recruiting further immune cells to increase the system's response to the pathogen.

Detection of inhibition of cytokine production can be performed by methods known to a skilled person including but not limited to ELISA, Q-PCR and intracellular cytokine staining detected by FACs and any other methods identifiable by a skilled person upon reading of the present disclosure.

As with other pharmaceuticals, it will be understood that the total daily usage of one or more pharmaceutical compositions of the present disclosure will be decided by a patient's attending physician within the scope of sound medical judgment. The specific therapeutically effective or prophylactically effective dose level for any particular patient will depend upon a variety of factors including the disorder being treated and the severity of the disorder; activity of the specific compound employed; the specific composition employed; the age, body weight, general health, sex and diet of the patient; the time administration, route of administration, and rate of excretion of the specific compound employed; the duration of the treatment; drugs used in combination or coincidental with the specific compound employed; and other factors known to those of ordinary skill in the medical arts.

For example, the amount of ZPs can be titrated to determine the effective amount for administering to an individual in need of treatment. A skilled person will appreciate that the attending physician would know how to and when to terminate, interrupt or adjust administration of ZPs in view of the clinical response In some embodiments, the effective amount of ZP and in particular PSA and/or PSB can be from about 1-100 micrograms to about 25 grams of body weight.

An effective amount and in particular a therapeutically effective amount of PSA can be for example in the range of between about 1 µg to about 100 µg of PSA per 0.025 kilograms of body weight. In some embodiments, the effective amount is in a range from about 10 µg to 100 µg per 25 grams of body weight. In some embodiments, the effective amount is in a range from about 25 µg to about 100 µg. In some embodiments, the effective amount is in a range from about 0.001 to about 1,000 µg per 25 grams of body weight. In some embodiments, the effective amount is in a range from about 0.1 to about 1,000 µg per 25 grams of body weight.

The term "about" as used herein indicates a variation that does not impact effects and functionality of a referenced item. In particular when referred to a concentration of an active agent the term "about" indicate a modification that maintains effectiveness of the concentration in the sense of the disclosure.

In some embodiments, one or more ZPs is comprised in a composition together with a suitable vehicle. The term "vehicle" as used herein indicates any of various media acting usually as solvents, carriers, binders or diluents for PSA and/or another ZPS comprised in the composition as an active ingredient.

In some embodiments, where the composition is to be administered to an individual the composition can be a pharmaceutical antiseptic composition, and comprises PSA and a pharmaceutically acceptable vehicle. In particular, the pharmaceutical compositions of the present disclosure are formulated for systemic administration and in particular for parenteral administration.

In some embodiments, pharmaceutical composition herein described can comprise a zwitterionic polysaccharide in an amount of from about 0.01 µg to about 1,000 µg. In some embodiments, pharmaceutical composition herein described can comprise a zwitterionic polysaccharide in an amount of from about 0.01 µg to about 1,000 µg.

In some embodiments, PSA can be included in pharmaceutical compositions together with an excipient or diluent. In particular, in some embodiments, pharmaceutical compositions are disclosed which contain PSA, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb a ZP and in particular PSA. Suitable excipients also include any substance that can be used to bulk up formulations with a ZP and in particular PSA to allow for convenient and accurate dosage. In addition to their use in the single-dosage quantity, excipients can be used in the manufacturing process to aid in the handling of PSA. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In embodiments herein described, compositions and, in particular, pharmaceutical compositions can be formulated for systemic administration, which includes enteral and parenteral administration.

Exemplary compositions for parenteral administration include but are not limited to sterile aqueous solutions, injectable solutions or suspensions including PSA and/or another ZP. In some embodiments, a composition for parenteral administration can be prepared at the time of use by dissolving a powdered composition, previously prepared in lyophilized form, in a biologically compatible aqueous liquid (distilled water, physiological solution or other aqueous solution).

In some embodiments, methods systems and compositions to treat sepsis or a condition associated thereto comprise administering PSA or a ZPS in combination with one or more antibiotics.

The term "antibiotic" or "antibacterials" indicates a type of antimicrobial compounds used as drug used in the treatment and prevention of bacterial infection Antibiotics can either kill or inhibit the growth of bacteria. A limited number of antibiotics also possess antiprotozoal activity.

In some embodiments herein described, one or more antibiotics, typically combinations of two or three antibiotics, can be administered together with PSA and/or other ZPS. In some embodiments the one or more antibiotics can be administered simultaneously, or sequentially, one with respect to the other and with respect to the ZPS. In some embodiments, antibiotics combinations usually comprise vancomycin to treat many MRSA infections. Some of the commonly used antibiotics used are ceftriaxone (Rocephin™), ceftazidime (Fortaz™), cefepime (Maxipime™), cefotaxime (Claforan™), clindamycin (Cleocin™), imipenem/cilastatin (Primaxin™), levofloxacin (Levaquin™), meropenem (Merrem™), ampicillin and sulbactam (Unasyn), piperacillin and tazobactam (Zosyn™), and additional antibiotics identifiable by a skilled person.

In some embodiments, once the infecting organism is isolated, the antibiotics can be selected following determination of the antibiotics most effective against the infecting organisms. In some additional or alternative embodiments, administration of PSA and/or other ZPS can be performed in combination with other therapeutic interventions, such as organ-system support and surgery, intubation [mechanical ventilation] to support lung function or dialysis to support kidney function) or a central venous catheter and fluid replacement with intravenous fluids and/or antihypotensive medication to raise blood pressure (e.g. norepinephrine [Levophed] or phenylephrine [Neo-Synephrine] administered by IV).

In some embodiments, methods and compositions to treat sepsis or a condition associated thereto comprise administering PSA or a ZPS in combination with one or more antiviral agent.

The term "antiviral agent" as used herein indicates any compound that can be used to treat a viral infection as will be understood by a skilled person. Antiviral in the sense of the disclosure comprise various antiviral drugs that can be used to treat viral infection such as HIV, herpes viruses, the hepatitis B and C viruses, and influenza A and B viruses and additional viral infection identifiable by a skilled person.

In some embodiments herein described, one or more antiviral agents, typically combinations of two or three, can be administered together with PSA and/or other ZPS. and an effective amount of an anti-viral agent, which may be, without limitation, abacavir, aciclovir, adefovir, amantadine, amprenavir, atazanavir, brincidovir, cidofovir, didanosin, efavirenz, emtricitabin, enfuvirtide, enviroxime, famciclovir, foscarnet, ganciclovir, indinavir, interferon alpha, lamivudin, lamivudine, lopinavir, nelfinavir, nevirapin, oseltamivir, pegylated interferon-alpha, penciclovir, ribavirin, ritonavir, saquinavir, stavudin, tenofovir, valaciclovir, valganciclovir zanamivir, zidovudine.

In embodiments herein described, one or more ZPs and in particular PSA herein described can be provided as a part of systems where they are provided in a combination to treat and/or prevent sepsis or a condition associated thereto as described herein.

In particular, in some embodiments, a system to treat and/or prevent sepsis or a condition associated thereto in an individual, comprises at least two of at least one zwitterionic polysaccharide and at least one antibiotic In some embodiments, a system to treat and/or prevent sepsis or a condition associated thereto in an individual, comprises at least two of at least one zwitterionic polysaccharide and at least one antiviral agent.

In particular, in some embodiments, a system to treat and/or prevent sepsis or a condition associated thereto in an individual, comprises at least two of at least one zwitterionic polysaccharide, at least one antibiotic and at least one antiviral agent.

In embodiments herein described the ZP, antibiotic and antiviral agents are comprised in formulations for simultaneous combined or sequential systemic and in particular parenteral administration to the individual in an effective amount to treat and/or prevent sepsis or the condition associated thereto in the individual The systems can be provided in the form of kits of parts. In a kit of parts, one or ore ZPs and in particular PSA, one or more antibiotics and/or other agents for treatment or prevention of sepsis or of a condition associated thereto can be comprised in the kit independently. The one or ore ZPs and in particular PSA, and one or more antibiotics can be included in one or more compositions, and each ZPs and each antibiotics can be in a composition together with a suitable vehicle.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. saline solution and the like).

Further effects and characteristics of the present disclosure will become more apparent hereinafter from the following detailed disclosure in the Examples section illustrating examples of the compositions and methods herein described as well as the experiments showing functional and physical interactions of PSA which are given by way or illustration only.

EXAMPLES

The methods and system herein disclosed are further illustrated in the following examples, which are provided by way of illustration and are not intended to be limiting.

In particular, in the following examples, the following materials and methods were used.

Bacterial Strains and Animals.

B. fragilis NCTC9343 and H. hepaticus ATCC51149 were obtained from the American Type Culture Collection. Conventionally reared SPF mice of strains C57BL/6NTac, C57BL/6NTac IL-10$^{-/-}$, and B6.129S6-Rag2$^{tm1Fwa}$ N12 (Rag2$^{-/-}$) were purchased from Taconic Farms (Germantown, N.Y.) and screened negative for B. fragilis and H. hepaticus. Swiss-Webster germ-free (SWGF) mice were purchased from Taconic Farms. Upon delivery in sterile shipping containers, the mice were transferred to sterile isolators (Class Biologically Clean, Madison, Wis.) in our animal facility. Animals were screened weekly for bacterial, viral, and fungal contamination as previously described. All animals were cared for under established protocols and the IACUC guidelines of Harvard Medical School and the California Institute of Technology.

Model of Inflammation:

Three models of intestinal inflammation were used: 1) CD4$^+$CD45Rb$^{high}$ T cells were purified from the spleens of wild-type or IL-10$^{-/-}$ donor mice by flow cytometry and transferred into Rag (C57Bl/6) recipients as described. 2) TNBS colitis was induced by pre-sensitization of wild-type (C57Bl/6) mice on the skin with a TNBS/acetone mix. Seven days after sensitization, 2.5% TNBS in ethanol was administered rectally; mice were sacrificed 3-6 days later.

Assays and Scoring Systems:

Cytokines from the spleen, colons, or mesenteric lymphonodes (MLNs) were assayed by ELISA, Q-PCR, or flow cytometry. Colitis was assessed with tissue sections (fixed, paraffin embedded, sectioned onto a slide, and stained with hematoxylin and eosin) and was scored by a blinded pathologist (Dr. R. T. Bronson, Harvard Medical School) according to a standard scoring system: 0, no thickening of colonic tissues and no inflammation (infiltration of lymphocytes); 1, mild thickening of tissues but no inflammation; 2, mild thickening of tissues and mild inflammation; 3, severe thickening and severe inflammation. BMDCs were purified from femurs of mice after extraction and washing in PBS. Cells were cultured for 8 days in C-RPMI-10 in the presence of GM-CSF (20 ng/mL; Biosource, Camarillo, Calif.). CD4$^+$ T cells were purified by negative selection over a magnetic column (Miltenyi or R&D Systems).

Flow Cytometry, Fluorescence-Activated Cell Sorting (FACS), and Staining.

Lymphocytes were isolated from mouse spleens that were mechanically disrupted into single-cell preparations. Red blood cells were lysed, and splenocytes (1×10$^6$) were incubated with various combinations of antibodies (BD Pharmingen, San Diego, Calif.) at 2 mg/mL for 30 min at 4° C. Cells were then washed and either fixed or used directly. For intracellular cytokine flow cytometry, samples were analyzed on a model FC500 cytometer (Beckman Coulter, Fullerton, Calif.) or a FacsCalibur (Becton Dickson), and data were analyzed with RXP Analysis Software (Beckman Coulter) or FlowJO. FACS was performed on a BD FACSAria, and cell purity was always >99%.

In Vitro Cytokine Assays.

For colon organ cultures, procedures were followed as previously reported. For co-culture, CD4$^+$ T cells were purified from splenic lymphocytes (prepared as described above) with a CD4$^+$ T Cell Subset Kit (R&D Systems, Minneapolis, Minn.) used as instructed by the manufacturer. Cell purity was always >95%. BMDCs were purified from femurs of mice after extraction and washing in PBS. Cells were cultured for 8 days in C-RPMI-10 in the presence of GM-CSF (20 ng/mL; Biosource, Camarillo, Calif.). Medium was replaced after 4 days, and adherent cells were cultured for an additional 4 days, at which point nonadherent cells were recovered, washed, and used directly. Cells were >95% CD11c$^+$ at the time of use. Purified CD4$^+$ T cells (1×10$^6$) were mixed with purified CD11c$^+$ BMDCs (1×10$^6$) in a 48-well plate and were incubated at 37° C. in an atmosphere containing 5% CO$_2$. Various stimuli were used, as described in Results. ELISA was performed with pre-coated plate kits (BD Pharmingen) according to the manufacturer's guidelines. In some assays, H. hepaticus, with or without wild-type B. fragilis or B. fragilis ΔPSA, was added at various concentrations.

Induction of experimental colitis. As assessed by PCR, Rag2$^{-/-}$ and control C57Bl/6 mice were negative for H. hepaticus colonization at the time of delivery. Splenic lymphocytes were harvested from wild-type donor mice, and CD4$^+$CD45Rb$^{high}$ cells were purified from lymphocyte populations by FACS as described above. Cells were washed with PBS, and 3×10$^5$ cells were injected intraperitoneally in a volume of 0.2 mL into recipient H. hepaticus-colonized Rag2$^{-/-}$ animals. For colonization experiments, both H. hepaticus (1×10$^8$ organisms) and B. fragilis (1×10$^8$ organisms) were introduced at the time of cell transfer. Throughout PSA treatment studies, animals received 50 μg of PSA by gavage 3 times per week. Animals were weighed throughout the experiment until sacrifice at 8 weeks.

Induction of Intestinal Inflammation-TNBS Colitis.

The backs of wild-type (C57BL/6) male mice were shaved, and pre-sensitization solution (150 μL; acetone with olive oil in a 4:1 ratio mixed with 5% TNBS in a 4:1 ratio) was slowly applied. Seven days after sensitization, mice were anesthetized with isofluorene and TNBS solution (100 μL; 1:1 5% TNBS with absolute ethanol) administered rectally through a 3.5 F catheter (Instech Solomon; SIL-C35). Mice were analyzed 4-6 days after TNBS administration.

Histologic Tissue Analysis.

Mouse tissues in Bouin's fixative (VWR, West Chester, Pa.) were embedded in paraffin, sectioned (6-μm slices), mounted onto slides, and stained with hematoxylin and eosin. Sections were evaluated in blinded fashion by a single pathologist (Dr. R. T. Bronson, Harvard Medical School).

Quantitative Real-Time PCR.

RNA was extracted with Trizol per the manufacturer's instructions (Invitrogen). RNA (1 μg) was reverse transcribed into cDNA with an iScript cDNA synthesis kit (Bio-Rad). cDNA was diluted by addition of 60 μL of water, and a 2-4, volume of this solution was used for Q-PCR. Q-PCR was performed using IQ SYBR Green supermix (Bio-Rad) and primers were used at 0.2 μm. Q-PCR was performed on a Bio-Rad iCycler IQ5. Sequences of Q-PCR primers were as follows 5'-3': IL-23 (p19) F: AGC TAT GAA TCT ACT AAG AGA GGG ACA (SEQ ID NO: 1) R:

GTC CTA GTA GGG AGG TGT GAA GTT G (SEQ ID NO: 2). IL-17A F: TTA AGG TTC TCT CCT CTG AA (SEQ ID NO: 3) R: TAG GGA GCT AAA TTA TCC AA. (SEQ ID NO: 4) TNFα F: ACG GCA TGG ATC TCA AAG AC (SEQ ID NO: 5) R: GTG GGT GAG GAG CAC GTA GT (SEQ ID NO: 6). IL-10 F: CTG GAC AAC ATA CTG CTA ACC G (SEQ ID NO: 7) R: GGG CAT CAC TTC TAC CAG GTA A (SEQ ID NO:8) RORyT F: CCG CTG AGA GGG CTT CAC (SEQ ID NO: 9) R: TGC AGG AGT AGG CCA CAT TAC A (SEQ ID NO: 10) IL-21 F: ATC CTG AAC TTC TAT CAG CTC CAC (SEQ ID NO: 11) R: GCA TTT AGC TAT GTG CTT CTG TTT C (SEQ ID NO: 12) IL-27 F: CTG TTG CTG CTA CCC TTG CTT (SEQ ID NO: 13) R: CAC TCC TGG CAA TCG AGA TTC (SEQ ID NO: 14).

PSA dosages: The results illustrated in the Examples section refer to a dosage of 5 µg/25 gram mouse. Ranges from 25 µg to 100 µg for a 25 gram mouse and lower than 10 µg/mouse to above 200 µg for a 25 gr/mouse are also expected to provide protection from sepsis.

Example 1

Oral Administration of PSA Suppresses Systemic Inflammation Associated with Intestinal Disease Experiments were performed to show that inflammation that occurs at mucosal sites, such as the intestine, can also impact extra-intestinal sites such as the spleen.

Animals were orally gavaged with vehicle or PSA twenty-four hours prior to being induced with colitis. Five days post-induction CD4+ T cells were isolated from the spleens of indicated animals and analyzed for the inflammatory cytokines TNF-α, IL-17a and IL-6 to determine how systemic inflammation is influenced during intestinal disease.

Figure 5:
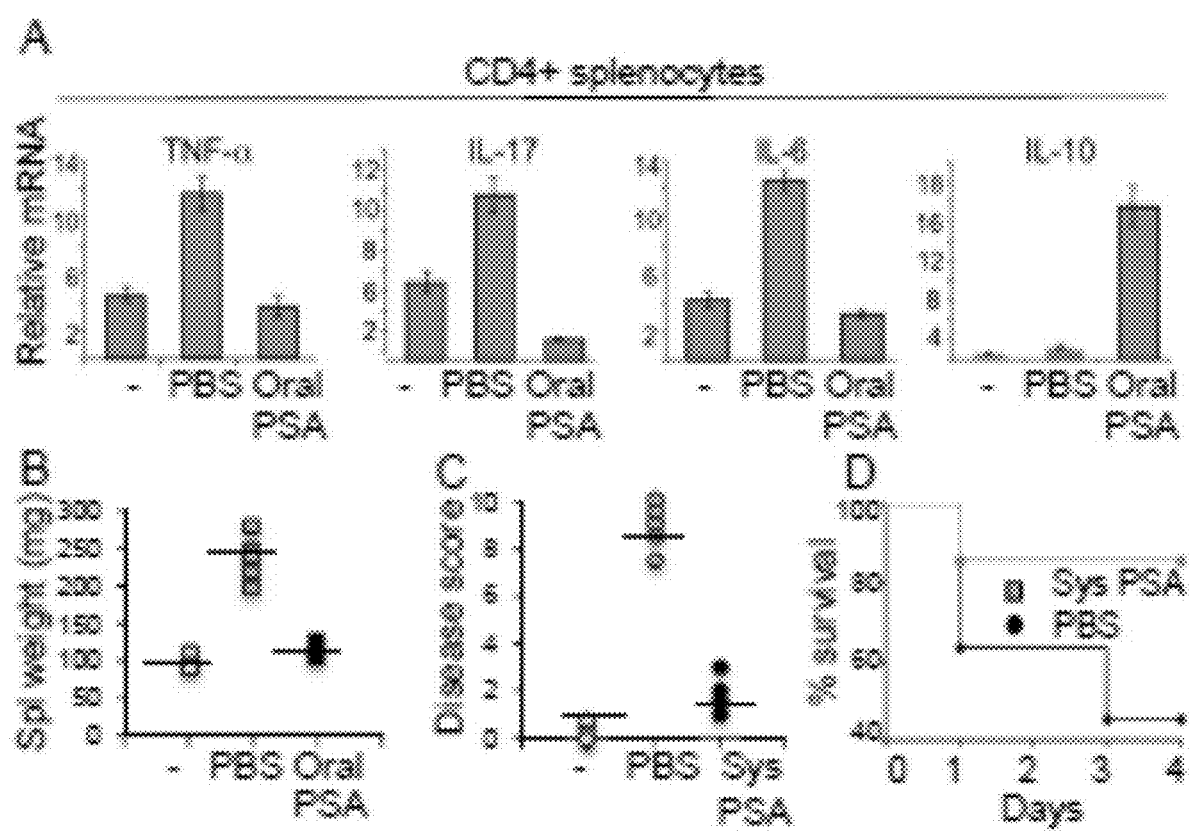
FIG. 5 Panel B shows the spleen weight removed from animals of FIG. 5 Panel A.

The results of these experiments did show that animals suffering from intestinal disease have elevated levels of pro-inflammatory cytokines within cells of the spleen and splenomegaly (FIG. 5, panels A and B).

However, it was also found that while colitogenic animals had significant increases in inflammatory T cells responses within the spleen, PSA treated animals had reduced cytokine expression at this systemic site (FIG. 5, panel A).

Additionally, the results show that splenomegaly occurs in colitic animals that orally gavaged PSA is also able to prevent (FIG. 5, panel C). Based on these findings, it was investigated also if PSA could also influence inflammation within the systemic compartment. Data obtained in animals following intravenous administration of PSA supported this conclusion (FIG. 5, panels C and D).

Example 2

Intravenous Administration of PSA Suppresses Colitis and Extra Intestinal Inflammation in a Model of Endotoxic Shock In order to verify whether PSA has anti-inflammatory effects outside of the intestine, experiments were performed in a model of endotoxic shock.

In this model, animals are treated intravenously with high doses of endotoxin (lipopolysaccharide; LPS). Administration of LPS leads to the production of massive amounts of inflammatory cytokines such as tumor necrosis factor α (TNF-α) and IL-6 and animals rapidly succumb to death. This model closely resembles the cytokine storm seen in patients suffering from septic shock.

In particular, Balb/c animals were orally gavaged with PSA or PBS control and subsequently induced for colitis using TNBS. Five days post-induction CD4+ T cells were isolated from the spleens of the indicated animals. Equal amounts of RNA were used to perform q-RT-PCR on IL6 or TNFa cytokines at 1 and 4 hours post-LPS. (FIG. 1 panel A diagram on the left, and FIG. 1 panel B diagram on the left)

In another set of experiments, Balb/c animals were treated intravenously with PSA 24 hours prior to be induced with TNBS colitis. Five days post-induction CD4+ T cells were isolated from the spleens of the indicated animals. Equal amounts of RNA were used to perform q-RT-PCR on IL6 or TNFa cytokines at 1 and 4 hours post-LPS. (FIG. 1 panel A diagram on the right, and FIG. 1 panel B diagram on the right)

The above two sets of experiments tested whether the mode of delivery of PSA influenced the outcome of disease. Consistent with this model, mock treated animals had significantly more serum TNF-α and IL6 (FIG. 1 panels A and B). Interestingly, PSA significantly blocked induction of serum inflammatory cytokines, but only when provided to the animal directly within the blood (FIG. 1 panels A and B).

Animals fed PSA had similar levels of both IL-6 and even slightly elevated TNF-α in the serum, indicating that PSA present in the gut cannot protect from this systemic acute inflammatory response (FIG. 1 panels A and B).

Example 3

Intravenous PSA Administration Protects Animals from Death in Two Distinct Models of Sepsis Detection of percent survival of in animals treated intravenously with high doses of endotoxin (lipopolysaccharide; LPS) was performed. Accordingly, Balb/C animals were orally or intravenously treated with PSA or PBS as described in Example 2 and the number of surviving mice counted. As a result of these experiments it was found that, intravenous administration of PSA potently protected animals from death associated with this model of endotoxin induced sepsis (FIG. 1 panel C).

To validate a role for PSA during protection from sepsis, a second, well-established mouse model of sepsis called the cecal-ligation puncture (CLP) model was used. CLP induces colonic spillage of bacteria into the peritoneal cavity, which then enter the bloodstream. Although there are limitations, this model is thought to best mimic a primary cause of human sepsis (polymicrobial infection from the gut). While about fifty percent of the animals that were mock treated with PBS succumbed to death by CLP, animals treated with PSA lived longer and had a significantly increased survival rate (FIG. 1 panel D).

Thus, PSA has a same protective effect in two distinct models of sepsis, demonstrating that PSA is able to protect from acute systemic inflammatory disease. These effects are only seen in the experiments reported in this Example when PSA is directly provided within the blood, suggesting that perhaps PSA may act through alternative mechanisms than those established within the gut. Thus, while production of PSA by *B. fragilis* within the intestine would not confer these benefits to the host, we have identified a natural product that can block the influx of inflammatory cytokines and prevent death during sepsis. Identifying PSA as a potential therapeutic candidate for the treatment of sepsis.

Example 4

Intravenous PSA Administration Protects an Individual from Sepsis

To mimic a clinically significant treatment situation, PSA was administered after inducing endotoxin induced sepsis. Balb/c animals were treated with high doses of LPS (500 ug) i.p. and subsequently treated i.v. with PBS, PSA or PSA was administered 30 minutes post-LPS (see FIG. 2).

Since this is an acute model, where overt inflammation occurs within one hour after induction two timepoints for PSA treatment were tested. In particular, serum was collected 1 and 4 hours post-LPS injection and cytokines TNF-α (FIG. 2 Panel A) and IL-6 (FIG. 2 Panel B) were detected by ELISA.

Figure 2:
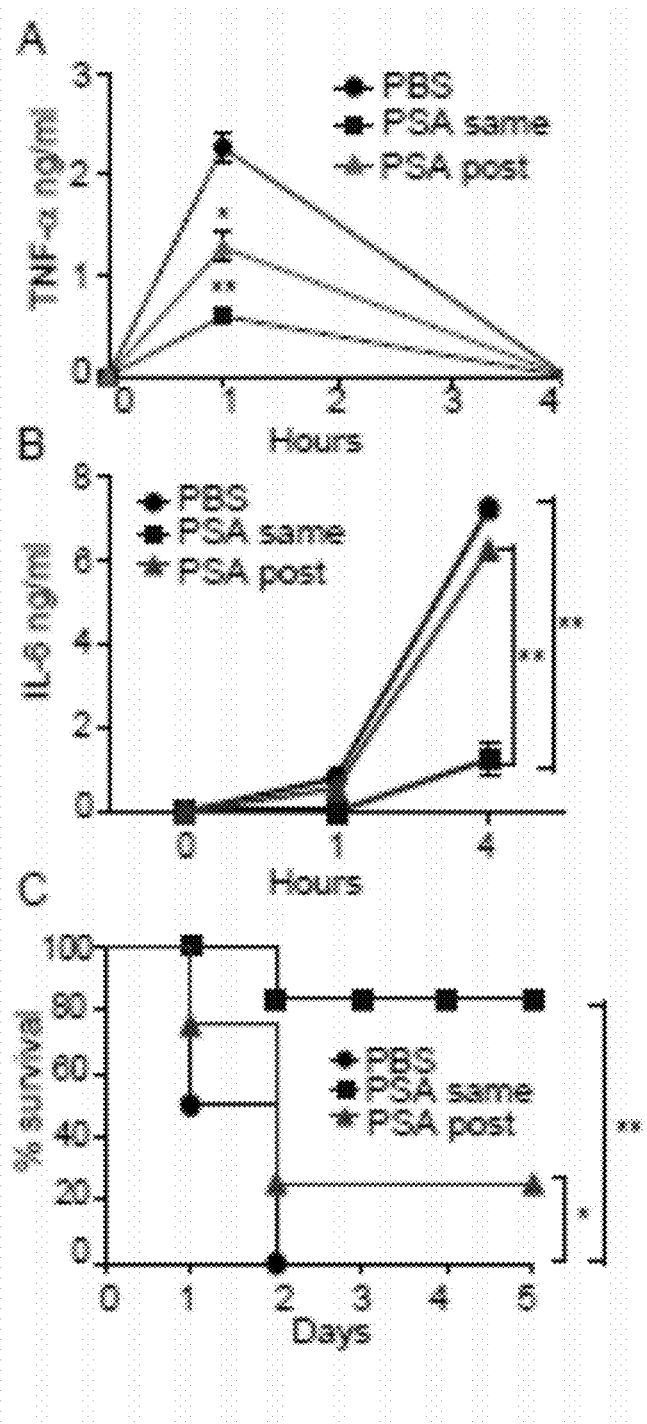
FIG. 2 illustrates data showing that PSA can treat endotoxin induced sepsis.

Each experiment consisted of at least 4 animals in each groups and was repeated twice. * $p<0.05$ **$p<0.005$ as measured by a students t test One group received i.v. administration of PSA directly after LPS injection (PSA same) while the second group received PSA thirty minutes post-LPS injection (PSA-post) (FIG. 2).

Animals treated with PSA directly following the induction of endotoxin shock had reduced levels of TNF-α and IL-6 similar to that of prophylactic treatment of PSA (compare FIG. 1 to FIG. 2 panels A and B). Moreover, these animals had a high survival rate and were protected from death (FIG. 2C). Remarkably, animals treated up to thirty minutes after induction of disease had lower serum levels of TNF-α and these animals also lived longer and had a higher survival rate (FIG. 2).

While IL-6 levels in this group of animals were similar to the control group, animals were still protected from death, suggesting that IL-6 might be dispensable for disease induction (FIG. 2 Panel B). PSA administered i.v. does not on its own induce TNF-α or IL-6 production (data not shown), suggesting that use of this molecule will not cause more damage during acute stress. Thus, these result show that PSA is able to rapidly prevent inflammation associated with sepsis and prolong survival. As most sepsis patients succumb to massive inflammation and organ damage before they are able to clear the live infection in the blood, our data support a role for PSA as part of a combinatorial therapy with antibiotics.

Example 5

PSA Protection from Endotoxin Induced Sepsis is Independent from TLR2 and IL-10 Signaling Pathways Previous reports have demonstrated that PSA is required and sufficient to suppress intestinal inflammation [5]. Additionally, numerous reports have demonstrated that PSA's ability to protect from chronic inflammatory diseases such as IBD and MS is dependent on signaling through TLR2 and production of IL-10 from T cells.

Therefore, to determine whether PSA protection from endotoxin induced sepsis also required these pathways the following experiments were performed.

Figure 3:
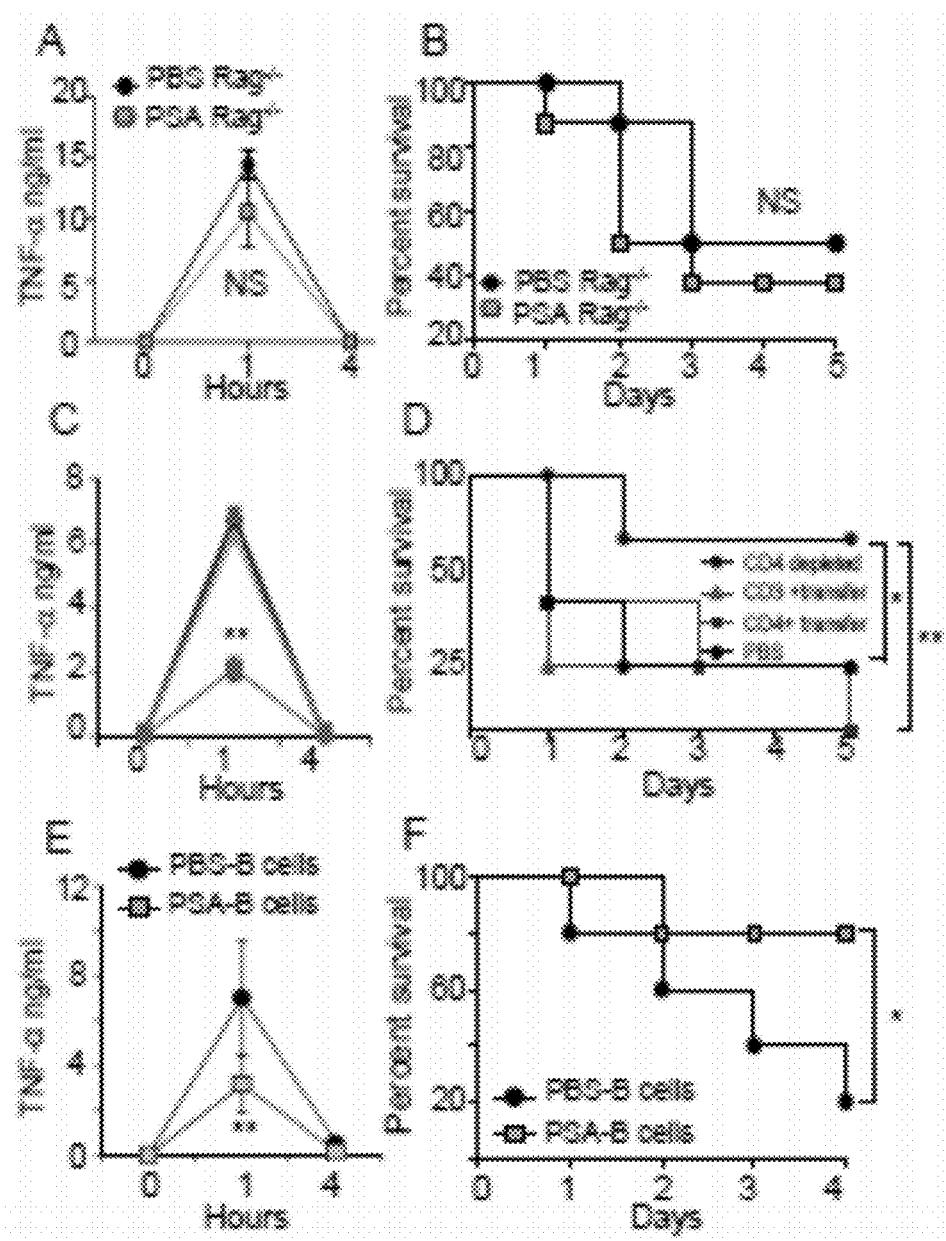
FIG. 3 illustrates data showing that a commensal molecule protects from sepsis through B cells.
Figure 6:
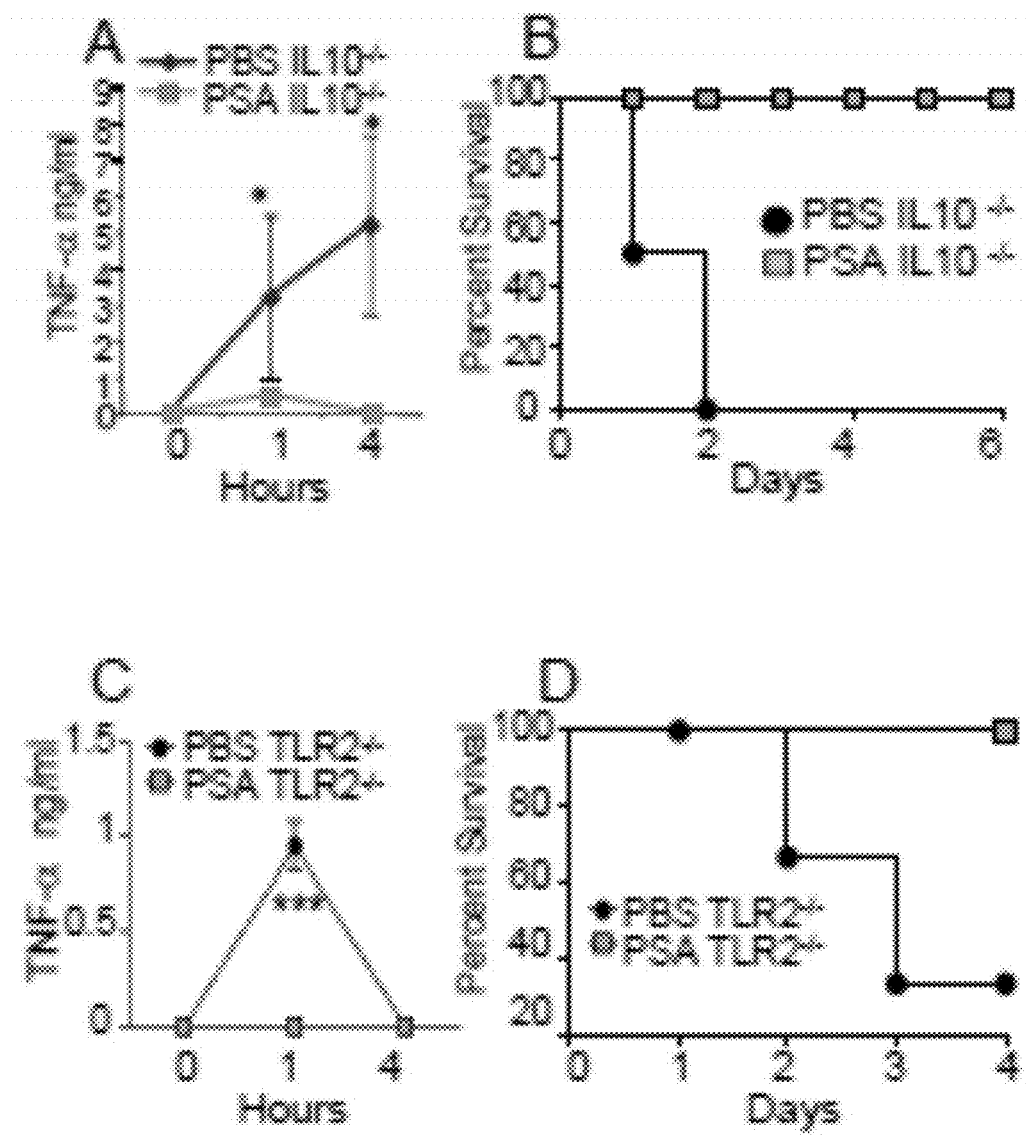
FIG. 6 shows PSA activity is independent on signaling through TLR2 and production of IL-10 from T cells.

Surprisingly, TLR2−/− or IL-10−/− mice treated with PSA were still completely protected from death and had suppressed TNFα and IL-6 levels during septic shock (FIGS. 6,3).

These data suggest that while TLR2 or IL-10 signaling pathways are required for PSA to promote anti-inflammatory responses when present within the gut, however these are not the mechanisms used when PSA is in the blood.

Example 6

PSA Protection from Endotoxin Induced Sepsis is Dependent on B Cells

PSA is known to influence T cell responses during steady state development as well as during protection from disease. Therefore, experiments were performed which did show that PSA protects from sepsis through B cells.

In particular, the requirement for T and B cells during PSA mediated protection from sepsis was tested. To this end, we treated RAG$^{-/-}$ mice with PSA and subsequently induced disease according to three sets of experiments.

In a first set of experiments, RAG$^{-/-}$ animals were treated i.v. with either PBS or PSA 24 hours prior to receiving high dose LPS i.p. Serum was collected from animals at 1 and 4 hours, TNF-α and IL-6 were measured by ELISA (FIG. 3 Panel A) and survival monitored (FIG. 3 Panel B). Two experiments were combined. *$p<0.05$ **$p<0.005$ using a logrank and Gehan-Wilcoxon test.

In a second set of experiments, RAG$^{-/-}$ recipients received either CD4+CD3+ (square) or total T cells (CD3+) (triangle) or CD4 depleted splenocytes (includes CD8+ T cells and CD19+ B cells) (sphere). Twenty-four hours later animals were given LPS. Serum was collected 1 and 4 hours post-LPS to measure cytokines (FIG. 3 Panel C) and survival was monitored (FIG. 3 Panel D).

In a third set of experiments sort purified CD19+ total B cells were purified from the spleen of donor animals and transferred into RAG$^{-/-}$ recipients and inflammatory cytokines were monitored at 1 and 4 hours (FIG. 3 Panel E) as well as survival (FIG. 3 Panel F). * $p<0.05$ **$p<0.005$ by a student's t test for all ELISA data and *$p<0.05$ **$p<0.005$ using a logrank and Gehan-Wilcoxon test for survival data. ELISA data is representative from one experiment repeated twice with an n of 4 in each group. Survival data combines multiple experiments.

In outcome of the above three sets of experiments it was shown that consistent with previously published literature, RAG$^{-/-}$ animals mount robust inflammatory responses and succumb to endotoxin induced death.

PSA no longer protected animals from sepsis in the absence of T and B cells, indicating a requirement for one of these cells types (FIG. 3 Panels A and B). Reconstitution of RAG$^{-/-}$ animals with sort purified cell populations thus represents a nice model to identify the relevant cell type. Remarkably, transfer of CD3+ total T cells nor CD4+ sort purified T cells into RAG$^{-/-}$ mice was unable to restore PSA mediated protection from death (FIG. 3 Panels C and D). In contrast, the transfer of CD4+ T cell depleted splenocytes restored the ability of PSA to prevent death and suppress systemic inflammation (FIG. 3 Panels C and D). Thus, PSA treatment of systemic inflammation is T cell-independent. These unexpected results compelled us to test a role for B cells, the major lymphocyte present within the spleen. Sort purified CD19+ B cells were transferred into RAG$^{-/-}$ mice that were induced for LPS sepsis, and treated groups with either i.v. PSA or PBS. Mice reconstituted with total B cells and given PSA survived and had significantly reduced serum levels of TNFα (FIG. 3 Panels E and F). This fascinating finding is consistent with very recent reports implicating B cells is mouse models of sepsis. Most importantly, no studies

Example 7

Marginal Zone B Cells are Required for PSA Mediated Sepsis Protection

Multiple subsets of B cells exist within the spleen including B1, follicular, and MZ B cell populations. Since PSA is able to protect from sepsis in the absence of T cells experiments were focused on B cell subset that do not require T cell help to secrete antibody. Both B1 and MZ B cells can secrete IgM in a T cell independent manner, therefore experiments were performed to determine whether either of these subsets conferred protection from sepsis by PSA. B1 cells and MZ B cells were sort purified and transferred into RAG$^{-/-}$ animals. Animals were subsequently treated with PSA and induced for disease.

In particular in a first set of experiments, marginal zone B cells (CD19+B220+IgM$^{hi}$CD21$^{hi}$CD23) were sort purified and transferred into RAG$^{-/-}$ recipients. Twenty-four hours later these animals were given high dose LPS and serum collected at 1 and 4 hours to assay for TNF-α (FIG. 4 Panel A) and survival was monitored (FIG. 4 Panel B).

Figure 4:
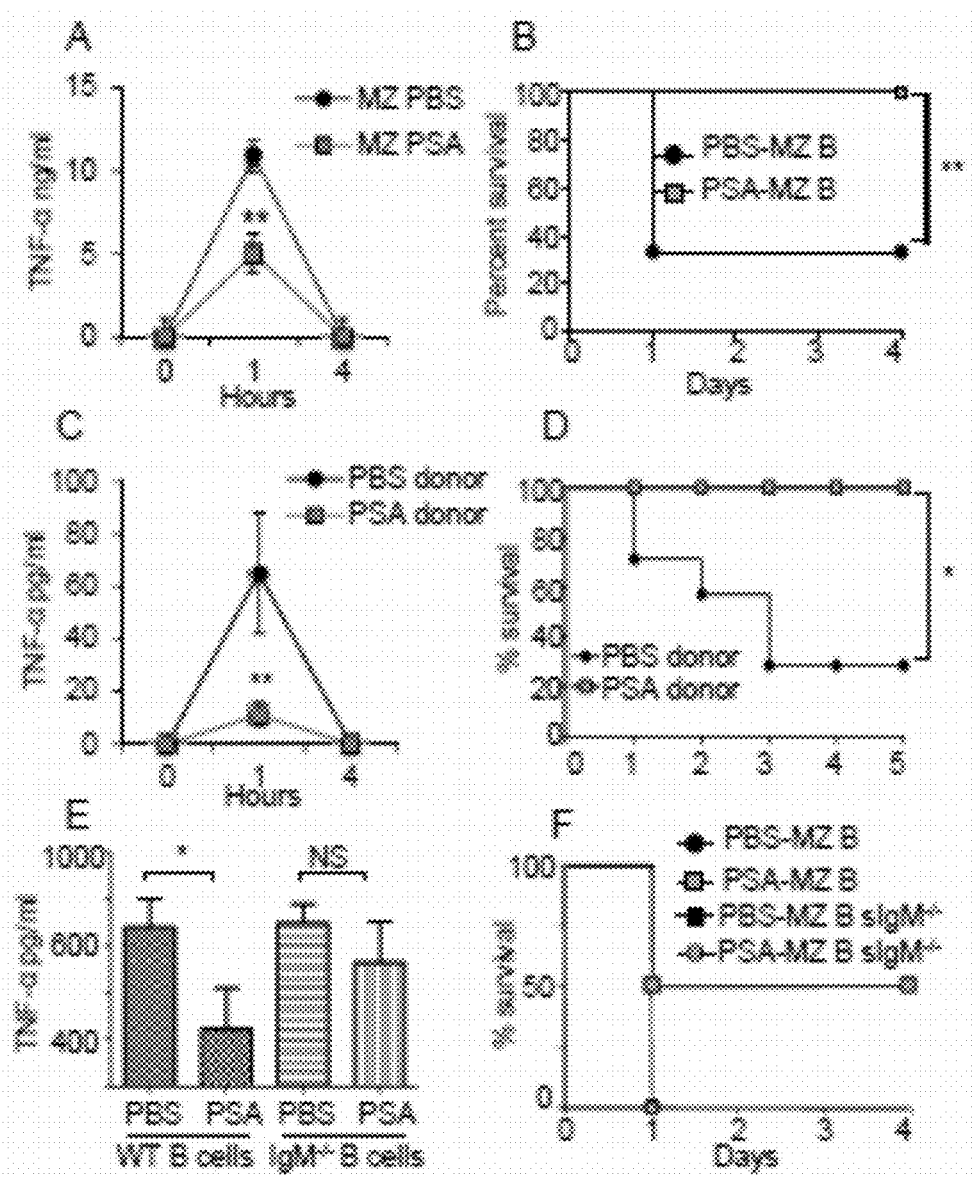
FIG. 4 illustrates data showing that PSA induces marginal zone B cell activity.

The results show interestingly, that while B1b cells did not restore PSA mediated protection in RAG$^{-/-}$ animals (data not shown), the transfer of a purified population of MZ B cells was able to elicit suppression of serum levels of TNF-α and protect animals from sepsis induced death (FIG. 4 Panels A and B). This does not rule out a role for B1a cells during PSA mediated protection from sepsis, however it does demonstrate that MZ B cells play an instrumental function during this process To further validate this conclusion, experiments were performed to determine whether the function of PSA on MZ B cells could be transplanted into mice that have never been treated with PSA. WT animals were treated i.v. with two doses of PSA and splenic MZ B cells were isolated and subsequently transferred into a RAG$^{-/-}$ recipients. LPS induced sepsis was then induced in the MZ B cell recipients without any treatment with PSA.

In particular a second set of experiments, WT C57Bl/6 animals were treated i.v. with either PBS or PSA (100 ug) every other day for a total of three days (FIG. 4 Panels C and D). MZ B cells were subsequently sort purified as in in the first set of experiments and 8×10$^5$ MZ B cells were transferred into RAG$^{-/-}$ recipients. Twenty-four hours later animals received high dose LPS (500 ug). Serum was collected at indicated time points to analyze TNF-α (FIG. 4 Panel E) and survival monitored (FIG. 4 Panel F). * p<0.05 **p<0.005 by a student's t test for all ELISA data and *p<0.05 **p<0.005 using a logrank and Gehan-Wilcoxon test for survival data.

The results show remarkably, that while animals receiving control MZ B cells had high levels of serum TNF-α and had a high mortality rate consistent with previous experiments, animals receiving PSA primed MZ B cells were completely protected from endotoxin induced sepsis (FIG. 4 Panels C and D). The protection conferred by the MZ B cell transfer was as good as treating the animals directly with PSA. These data demonstrate that PSA is able to protect from sepsis by acting through a marginal zone B cell population.

Additionally, while germfree mice possess nearly normal levels of MZ B cells within the spleen, changes in the composition of the microbiota can lead to defective MZ B cell maintenance. This suggests that specific members of the microbiota can influence MZ B cell function

Example 8

Figure 7:
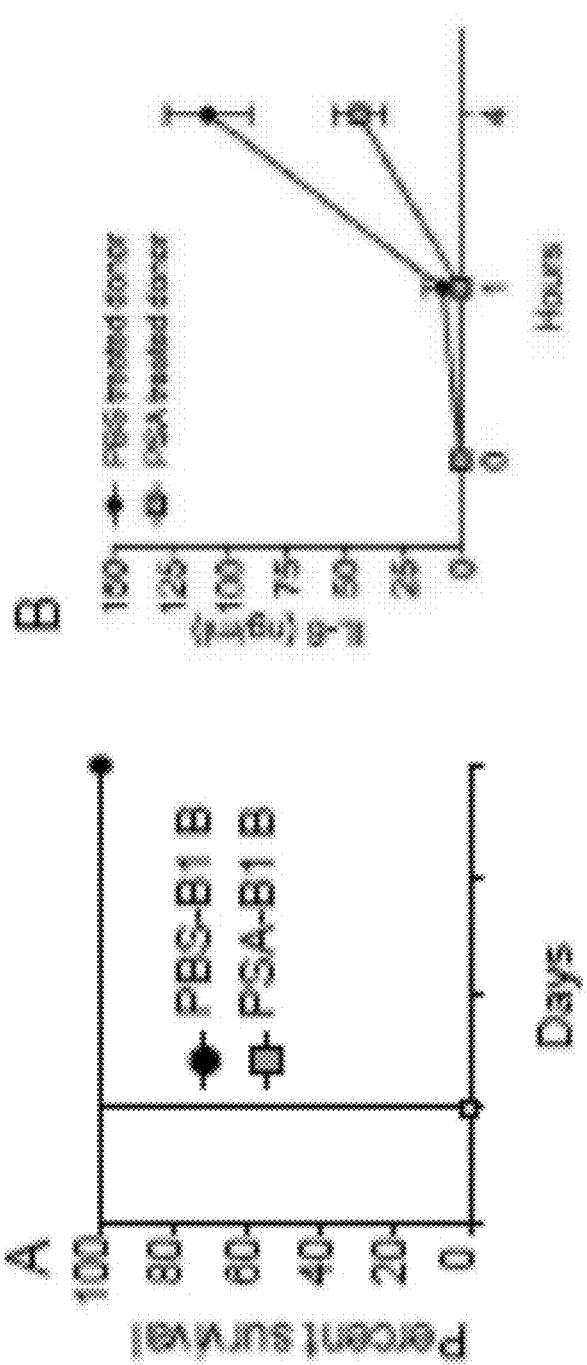
FIG. 7 shows that PSA activity is dependent on Marginal zone B cells.
Figure 8:
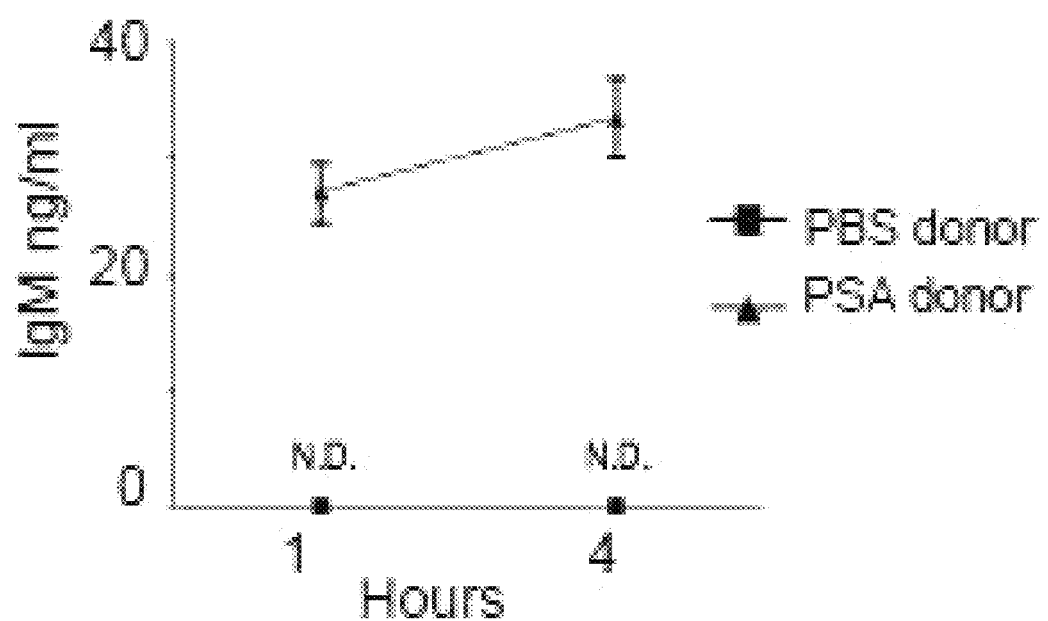
FIG. 8 shows that PSA activity is dependent on IgM production from Marginal zone B cells. In particular.

IgM Production by Marginal Zone B Cells is Required for PSA Mediated Sepsis Protection Marginal zone B cells secrete copious amounts of polyreactive IgM. IgM recognizes conserved bacterial structures and is able to rapidly control bacterial infections and accordingly, has a protective role in CLP. Based on this, serum was isolated from RAG$^{-/-}$ animals that received a MZ B transplant from PSA treated mice and quantitated IgM serum levels. While animals that received MZ B cells from mock treated mice have very low levels of IgM in the serum during LPS induced sepsis, mice receiving MZ B cells from PSA treated animals had high levels of circulating IgM (FIG. 7)

These data suggest that PSA is able to induce the secretion of IgM from MZ B cells and aid in protection from sepsis. Indeed, polyreactive IgM aids in clearance of endotoxin from the blood and reduces inflammation.

To test whether IgM is the mechanism by which PSA is able to protect from endotoxin induced sepsis total B cells were isolated from the spleen of animals that are unable to make secreted IgM (sIgM$^{-/-}$) and transferred these cells into RAG$^{-/-}$ recipients according to procedure of Example 7. Animals were either mock treated or treated with i.v. PSA and subsequently induced for sepsis.

PBS treated animals had high serum concentrations of inflammatory cytokines and rapidly succumbed to death, while animals that were PSA treated were protected (FIG. 4 Panels E and F). However, animals that received MZ B cells from sIgM$^{-/-}$ mice were no longer protected by administration of PSA (FIG. 4 Panels E and F). Taken together, these data demonstrate that PSA can coordinate the protection of animals from sepsis through the influence of marginal zone B cell IgM secretion. These are the first studies to identify a therapeutic inducer of IgM for sepsis treatment.

Example 10

PSA as a Therapeutic Agent for Sepsis Through Activation of B Cells

Previous studies have highlighted an important role for B cells during sepsis. μMT$^{-/-}$ animals that lack B cells, succumb to worsened LPS induced and polymicrobial sepsis. Interestingly, mortality during sepsis in T cell deficient mice is similar to WT animals, indicating that B cells are instrumental to the survival of the host during septic shock.

Antibodies or cytokines secreted from B cells are thought to be important for conferring protection as transfer of serum from WT animals into a B cell deficient host is sufficient to enhance survival during sepsis.

Supporting a role for IgM, sIgM$^{-/-}$ animals suffer a much higher mortality rate when compared to WT animals during polymicrobial sepsis. Taken together these findings indicate that B cell secretion of IgM is an important mechanism to protect the host from sepsis and suggest that harnessing the protective capacity of B cells during this disease could be a novel therapy.

The above results show that PSA can control the protective activity of B cells during sepsis. A possible mechanism herein provided with no intent of being limiting is that as polysaccharides from other bacteria are known to serve as BCR agonist, it is possible that PSA could directly activate an MZ B cell through ligation of surface bound IgM. Alternatively, although with is also possible that PSA acts through other innate immune receptors to activate MZ B cells directly.

Additionally, PSA does not elicit overt inflammation when administered i.v into animals (data not shown), and therefore would not exacerbate the cytokine storm known to occur during sepsis.

Septic patients often succumb to death very rapidly from organ failure in response to a overzealous immune response In view of the above, PSA is expected to be used in therapy in combination with antibiotics to prolong life and allow treatment and recovery from sepsis Here it is demonstrated that administration of PSA to animals induced for experimental sepsis potently prevents disease. PSA rapidly suppresses numerous inflammatory cytokines, and significantly rescues animals from death in the endotoxin shock and CLP models. Applicants have previously identified that mucosally produced PSA can protect from IBD in a TLR2 and IL-10 depend manner. However, when PSA is provided into the extra-intestinal compartment, it instead influences natural antibody production from marginal zone B cells independent of TLR2 or IL-10.

The examples set forth above are provided to give those of ordinary skill in the art a complete disclosure and description of how to make and use the embodiments of the compounds compositions and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

Further, the sequence listing submitted herewith is incorporated herein by reference in its entirety.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Ying Wang, W. M. K.-M., Michael H. Roehrl, and Dennis L. Kasper, *Structural basis of the abscess-modulating polysaccharide A2 from Bacteroides fragilis.* Proc. Natl. Acad. Sci. U.S.A., 2000. 97: p. 6.
2. Wiltrud M. Kalka-Moll, Y. W., L. E. Comstock, Sylvia E. Gonzalez, Arthur O. Tzianabos and Dennis L. Kasper, *Immunochemical and Biological Characterization of Three Capsular Polysaccharides from a Single Bacteroides fragilis Strain.* Infect. Immun., 2001. 69(4): p. 6.
3. Reid, R. R., et al., *Endotoxin shock in antibody-deficient mice: unraveling the role of natural antibody and complement in the clearance of lipopolysaccharide.* Journal of immunology, 1997. 159(2): p. 970-5.
4. Richard, M. Z. a. Y., *Marginal zone B-cells, a gatekeeper of innate immunity.* Frountiers in immunology, 2011. 2: p. 10.
5. Mazmanian, S. K., et al., *An immunomodulatory molecule of symbiotic bacteria directs maturation of the host immune system.* Cell, 2005. 122(1): p. 107-18.

What is claimed is:

1. A method to treat sepsis, severe sepsis, septic shock, multiple organ dysfunction syndrome (MODS), or systemic inflammatory response syndrome (SIRS) in an individual, the method comprising:
   identifying an individual in need, wherein the individual in need is an individual having a condition selected from the group consisting of sepsis, severe sepsis, septic shock, MODS, and SIRS, and wherein the condition is caused by polymicrobial infection from the gut of the individual;
   systemically administering to the individual in need an effective amount of a zwitterionic polysaccharide; and
   systemically administering to the individual in need an effective amount of marginal zone B cells.
   wherein the effective amount of the zwitterionic polysaccharide induces IgM production from the marginal zone B cells,
   thereby treating sepsis, severe sepsis, septic shock, MODS, or SIRS in the individual.

2. The method of claim 1, wherein the systemically administering is performed by intravenously administering the zwitterionic polysaccharide.

3. The method of claim 1, wherein the systemically administering is performed by administering the zwitterionic polysaccharide in combination with an effective amount of one or more antibiotics.

4. The method of claim 1, wherein the effective amount of zwitterionic polysaccharide is in a range from about 0.001 µg to about 1,000 µg per 0.25 kilograms of body weight.

5. The method of claim 1, wherein the zwitterionic polysaccharide is polysaccharide A (PSA).

6. A method to prevent sepsis, severe sepsis, septic shock, multiple organ dysfunction syndrome (MODS), or systemic inflammatory response syndrome (SIRS) in an individual, the method comprising:
   identifying an individual in need, wherein the individual in need is an individual at a risk of having a condition selected from the group consisting of sepsis, severe sepsis, septic shock, and SIRS, and wherein the condition is caused by polymicrobial infection from the gut of the individual;
   systemically administering to the individual in need an effective amount of a zwitterionic polysaccharide; and
   systemically administering to the individual in need an effective amount of marginal zone B cells,
   wherein the effective amount of the zwitterionic polysaccharide induces IgM production from the marginal zone B cells,
   thereby preventing sepsis, severe sepsis, septic shock, MODS, or SIRS in the individual.

7. The method of claim 6, wherein the systemically administering is performed by intravenously administering the zwitterionic polysaccharide.

8. The method of claim 6, wherein the systemically administering is performed by administering the zwitterionic polysaccharide in combination with an dfective amount of one or more antibiotics.

9. The method of claim 6, wherein the effective amount of zwitterionic polysaccharide is in a range from about 0.001 µg to about 1,000 µg per 0.25 kilograms of body weight.

10. The method of claim 6, wherein the zwitterionic polysaccharide is polysaccharide A (PSA).

11. The method of claim 1, wherein the effective amount of zwitterionic polysaccharide is in a range from about 25 µg to about 1000 µg per 25 gram of body weight.

12. The method of claim 6, wherein the effective amount of zwitterionic polysaccharide is in a range from about 25 µg to about 1000 µg per 25 gram of body weight.

13. A method to prevent sepsis, severe sepsis, septic shock, multiple organ dysfunction syndrome (MODS), or systemic inflammatory response syndrome (SIRS) in an individual, the method comprising:
   systematically administering to an individual in need an effective amount of zwitterionic polysaccharide primed marginal zone B cells, thereby preventing sepsis, severe sepsis, septic shock, MODS, or SIRS in the individual.

14. The method of claim 13, wherein the zwitterionic polysaccharide primed marginal zone B cells are capable of producing IgM.

15. The method of claim 13, wherein the zwitterionic polysaccharide primed marginal zone B cells are obtained from a subject treated with a zwitterionic polysaccharide.

16. The method of claim 13, wherein the individual in need is not administered with ny zwitterionic polysaccharide.

17. A method to treat sepsis, severe sepsis, septic shock, multiple organ dysfunction syndrome (MODS), or systemic inflammatory response syndrome (SIRS) in an individual, the method comprising:
   systematically administering to an individual in need an effective amount of zwitterionic polysaccharide primed marginal zone B cells, thereby treating sepsis, severe sepsis, septic shock, MODS, or SIRS in the individual.

18. The method of claim 17, wherein the zwitterionic polysaccharide primed marginal zone B cells are capable of producing IgM.

19. The method of claim 17, wherein the zwitterionic polysaccharide primed marginal zone B cells are obtained from a subject treated with a zwitterionic polysaccharide.

20. The method of claim 17, wherein the individual in need is not administered with any zwitterionic polysaccharide.

* * * * *